United States Patent [19]
Yaksh

[11] Patent Number: 6,166,039
[45] Date of Patent: *Dec. 26, 2000

[54] PERIPHERALLY ACTIVE ANTI-HYPERALGESIC OPIATES

[75] Inventor: Tony L. Yaksh, San Diego, Calif.

[73] Assignee: Regents of the Univ. of California, Oakland, Calif.

[*] Notice: This patent is subject to a terminal disclaimer.

[21] Appl. No.: 09/199,873

[22] Filed: Nov. 24, 1998

Related U.S. Application Data

[63] Continuation of application No. 08/528,510, Sep. 12, 1995, Pat. No. 5,849,761.

[51] Int. Cl.$^7$ ................................................. A61K 31/445
[52] U.S. Cl. .......................... 514/327; 514/326; 514/316; 514/237.2
[58] Field of Search .................. 514/327, 237.2, 514/316, 326

[56] References Cited

U.S. PATENT DOCUMENTS

| | | | |
|---|---|---|---|
| 3,275,510 | 9/1966 | Magid et al. | 167/58 |
| 3,714,159 | 1/1973 | Janssen et al. | 260/247.1 |
| 3,789,072 | 1/1974 | Bernstein | 260/557 B |
| 3,884,916 | 5/1975 | Janssen et al. | 260/247.7 |
| 3,914,238 | 10/1975 | Soudijn et al. | 260/293.58 |
| 3,950,537 | 4/1976 | DeBenneville et al. | 424/322 |
| 3,996,214 | 12/1976 | Dajani et al. | 260/240 |
| 3,998,832 | 12/1976 | Adelstein et al. | 260/293.54 |
| 4,012,374 | 3/1977 | Wade et al. | 260/239.3 |
| 4,012,393 | 3/1977 | Markos et al. | 260/293.54 |
| 4,013,668 | 3/1977 | Adelstein et al. | 260/293.54 |
| 4,025,652 | 5/1977 | Diamond et al. | 424/322 |
| 4,057,549 | 11/1977 | Adelstein et al. | 260/293.54 |
| 4,060,635 | 11/1977 | Diamond et al. | 424/322 |
| 4,066,654 | 1/1978 | Adelstein et al. | 260/293.69 |
| 4,069,223 | 1/1978 | Adelstein et al. | 260/293.76 |
| 4,072,686 | 2/1978 | Adelstein et al. | 260/293.69 |
| 4,115,564 | 9/1978 | Diamond et al. | 424/244 |
| 4,116,963 | 9/1978 | Adelstein et al. | 260/293.69 |
| 4,125,531 | 11/1978 | Yen | 546/133 |
| 4,147,804 | 4/1979 | Diamond et al. | 424/322 |
| 4,160,099 | 7/1979 | Bodor | 560/110 |
| 4,194,045 | 3/1980 | Adelstein | 546/209 |
| 4,203,920 | 5/1980 | Diamond et al. | 260/553 A |
| 4,218,454 | 8/1980 | DeGraw et al. | 424/260 |
| 4,238,390 | 12/1980 | Meienhofer et al. | 260/112.5 |
| 4,269,843 | 5/1981 | DeGraw et al. | 424/260 |
| 4,277,605 | 7/1981 | Buyniski et al. | 546/74 |
| 4,326,074 | 4/1982 | Diamond et al. | 564/47 |
| 4,326,075 | 4/1982 | Diamond et al. | 564/48 |
| 4,328,803 | 5/1982 | Pape | 128/276 |
| 4,371,463 | 2/1983 | Pert et al. | 260/112.5 E |
| 4,384,000 | 5/1983 | Lanier | 424/267 |
| 4,407,794 | 10/1983 | Roques et al. | 424/177 |
| 4,416,886 | 11/1983 | Bernstein | 424/260 |
| 4,430,327 | 2/1984 | Frederickson | 424/177 |
| 4,493,848 | 1/1985 | LaHann et al. | 424/324 |
| 4,517,295 | 5/1985 | Bracke et al. | 435/101 |
| 4,533,739 | 8/1985 | Pitzele et al. | 548/559 |

(List continued on next page.)

FOREIGN PATENT DOCUMENTS

| | | |
|---|---|---|
| 0127154 | 5/1984 | European Pat. Off. . |
| 171742A2 | 8/1985 | European Pat. Off. . |
| 325406A2 | 1/1989 | European Pat. Off. . |
| 325406A3 | 1/1989 | European Pat. Off. . |
| 325406B1 | 1/1989 | European Pat. Off. . |
| 351897A2 | 6/1989 | European Pat. Off. . |
| 351897A3 | 6/1989 | European Pat. Off. . |
| 0350221 | 1/1990 | European Pat. Off. . |
| 0383635 | 8/1990 | European Pat. Off. . |
| 512902A1 | 4/1992 | European Pat. Off. . |
| 0544391 | 8/1992 | European Pat. Off. . |
| 0582727 | 2/1994 | European Pat. Off. . |
| 0640596 | 3/1995 | European Pat. Off. . |
| 2100711 | 3/1972 | France . |
| 2169292 | 7/1986 | United Kingdom . |
| 2287404 | 9/1995 | United Kingdom . |
| 9102497 | 3/1991 | WIPO . |
| 9202223 | 8/1991 | WIPO . |
| 9213540 | 8/1992 | WIPO . |
| 9316707 | 9/1993 | WIPO . |
| 9709973 | 3/1997 | WIPO . |
| 9732857 | 9/1997 | WIPO . |
| 9733634 | 9/1997 | WIPO . |
| 9827985 | 7/1998 | WIPO . |
| 9842275 | 10/1998 | WIPO . |

OTHER PUBLICATIONS

Abbott, "Peripheral and central antinociceptive actions of ethylketocyclazocine in the formalin test." *Eur. J. Pharmacol.* 142:93–100 (1988).

Acne in Teens: Ways to Control it, AAFP patient education brochure series, Health Notes from Your Family Doctor, (1994).

Adelstein, Gilbert W., et al., "3,3–Diphenyl–3–(2–alkyl–1, 3,4–oxadiazol–5–yl)propylcycloalkylamines, a Novel Series of Antidiarrheal Agents," *J. Med. Chem.* 19:1221–1225, (1976).

Alreja, et al., The formalin test: A tonic pain model in the primate, *Pain*, 20:97–105 (1984).

Andreev et al., "Opioids suppress spontaneous activity of polymodal nociceptors in rat paw skin induced by ultraviolet radiation." *Neuroscience* 58(4):793–798 (1994).

Ansel et al., "Cytokine modulation of keratinocyte cytokines", *J. of Inv. Derm.* 94(6):101–107 (1990).

(List continued on next page.)

*Primary Examiner*—Phyllis G. Spivack
*Attorney, Agent, or Firm*—Stephanie L. Seidman; Heller Ehrman White and McAuliffe LLP

[57] ABSTRACT

Methods for treatment of peripheral hyperalgesia are provided, comprising administering compositions containing an anti-hyperalgesia effective amount of one or more compounds that directly or indirectly interact with peripheral opiate receptors, but that do not, upon topical or local administration, elicit central nervous system side effects. The anti-diarrheal compound 4-(p-chlorophenyl)-4-hydroxy-N-N-dimethyl-α,α-diphenyl-1-piperidinebutyramide hydrochloride is preferred for use in the methods.

22 Claims, No Drawings

U.S. PATENT DOCUMENTS

| | | | |
|---|---|---|---|
| 4,626,539 | 12/1986 | Aungst et al. | 514/282 |
| 4,749,706 | 6/1988 | Lawson et al. | 514/282 |
| 4,824,853 | 4/1989 | Wals et al. | 514/327 |
| 4,870,084 | 9/1989 | Eggler et al. | 514/320 |
| 4,871,750 | 10/1989 | Roberts | 514/328 |
| 4,892,735 | 1/1990 | Harrap | 424/435 |
| 4,897,260 | 1/1990 | Ross et al. | 424/59 |
| 4,898,873 | 2/1990 | Wals et al. | 514/327 |
| 4,917,896 | 4/1990 | Peck et al. | 424/449 |
| 4,939,142 | 7/1990 | Budai et al. | 514/238 |
| 4,990,521 | 2/1991 | Van Daele et al. | 514/327 |
| 5,039,642 | 8/1991 | Chrobaczek | 502/155 |
| 5,069,909 | 12/1991 | Sharma et al. | 424/449 |
| 5,100,903 | 3/1992 | Lalinde et al. | 514/327 |
| 5,109,135 | 4/1992 | D'Ambra et al. | 544/73 |
| 5,112,596 | 5/1992 | Malfroy-Camine | 424/2 |
| 5,116,847 | 5/1992 | Gilbert et al. | 514/327 |
| 5,116,868 | 5/1992 | Chen et al. | 514/546 |
| 5,143,938 | 9/1992 | Calvet et al. | 514/653 |
| 5,149,538 | 9/1992 | Granger et al. | 424/449 |
| 5,202,130 | 4/1993 | Grant et al. | 424/617 |
| 5,214,080 | 5/1993 | Iwamura et al. | 523/336 |
| 5,229,127 | 7/1993 | McKinzie | 424/427 |
| 5,236,947 | 8/1993 | Calvet et al. | 514/433 |
| 5,240,932 | 8/1993 | Morimoto et al. | 514/282 |
| 5,242,944 | 9/1993 | Park et al. | 514/466 |
| 5,248,505 | 9/1993 | Garwin | 424/472 |
| 5,266,465 | 11/1993 | Rubin et al. | 435/69.2 |
| 5,273,056 | 12/1993 | McLaughlin et al. | 128/898 |
| 5,273,751 | 12/1993 | Dubroff | 424/427 |
| 5,278,126 | 1/1994 | Katano et al. | 503/201 |
| 5,282,851 | 2/1994 | Jacob-LaBarre | 623/6 |
| 5,286,751 | 2/1994 | Sunshine et al. | 514/570 |
| 5,292,362 | 3/1994 | Bass et al. | 106/124 |
| 5,300,648 | 4/1994 | Emonds-Alt et al. | 546/193 |
| 5,312,899 | 5/1994 | Schiller | 530/331 |
| 5,345,943 | 9/1994 | Hargreaves et al. | 128/742 |
| 5,354,863 | 10/1994 | Dappen et al. | 546/35 |
| 5,366,979 | 11/1994 | Lawson | 514/282 |
| 5,369,131 | 11/1994 | Poli et al. | 514/772.4 |
| 5,384,124 | 1/1995 | Courteille et al. | 424/430 |
| 5,387,688 | 2/1995 | Feldman et al. | 546/223 |
| 5,403,867 | 4/1995 | Okumura et al. | 514/573 |
| 5,432,176 | 7/1995 | Walser | 514/252 |
| 5,434,292 | 7/1995 | Saita et al. | 560/51 |
| 5,436,009 | 7/1995 | Jauw et al. | 424/436 |
| 5,437,994 | 8/1995 | Emerson et al. | 435/240.2 |
| 5,446,052 | 8/1995 | Emonds-Alt et al. | 514/318 |
| 5,446,070 | 8/1995 | Mantelle | 514/772.6 |
| 5,460,821 | 10/1995 | Masiz | 424/449 |
| 5,478,814 | 12/1995 | Packman | 514/53 |
| 5,589,480 | 12/1996 | Elkhoury et al. | 514/282 |
| 5,618,557 | 4/1997 | Wille et al. | 424/449 |
| 5,645,854 | 7/1997 | Masiz | 424/449 |
| 5,646,151 | 7/1997 | Kruse et al. | 514/255 |
| 5,667,773 | 9/1997 | Farrar et al. | 424/78.05 |
| 5,686,106 | 11/1997 | Kelm et al. | 424/463 |
| 5,688,955 | 11/1997 | Kruse et al. | 546/276.4 |
| 5,744,458 | 4/1998 | Kruse et al. | 514/91 |
| 5,760,023 | 6/1998 | Farrar et al. | 514/150 |
| 5,763,445 | 6/1998 | Kruse et al. | 514/255 |
| 5,798,093 | 8/1998 | Farrar et al. | 424/45 |
| 5,811,078 | 9/1998 | Maycock et al. | 424/45 |
| 5,834,480 | 11/1998 | Elkhoury | 514/289 |
| 5,849,761 | 12/1998 | Yaksh | 514/327 |
| 5,849,762 | 12/1998 | Farrar et al. | 514/327 |
| 5,855,907 | 1/1999 | Peyman | 424/434 |
| 5,866,143 | 2/1999 | Elkhoury | 424/401 |
| 5,869,521 | 2/1999 | Farrar et al. | 514/422 |
| 5,888,494 | 3/1999 | Farrar et al. | 424/78.05 |
| 5,919,473 | 7/1999 | Elkhoury | 424/422 |
| 5,945,443 | 8/1999 | Kruse et al. | 514/429 |
| 5,962,477 | 10/1999 | Mak | 514/327 |
| 5,981,513 | 11/1999 | Kruse et al. | 514/91 |
| 5,994,372 | 11/1999 | Yaksh | 514/327 |

OTHER PUBLICATIONS

Antonijevic, et al., Perineurial defect and peripheral opioid analgesia in inflammation, *J. Neurosci.*, 15(1):165–172 (1995).

Atwouters, et al., "Loperamide: Survey of studies on mechanism of its antidiarrheal activity," *Dig. Dis. and Sci.* 38(6):977–995, (1993).

Atwouters et al., "Pharmacology of antidiarrheal drugs." *Ann. Rev. Pharmacol. Toxicol.* 23:279–301 (1983).

Bergfeld, et al., The evaluation and management of acne: Economic considerations, *J. Am. Acad. Dermatol.* 32(5)S52–56 (1995).

Berrebi et al., "Verapamil inhibits B–cell proliferation and tumor necrosis factor release and induces a clinical response in B–cell chronic lymphocytic leukemia", *Leukemia* 8(12):2214–2216 (1994).

Berson, et al., The treatment of acne: The role of combinantion therapies, *J. Am. Acad. Dermatol.* 32:S31–41 (1995).

Bianchi and Goi, "On the antidiarrheal and analgesic properties of diphenoxylate, difenoxine and loperamide in mice and rats." *Arzeneimittel–Forschung/Drug Research* 27(1),5, 1040–1043 (1977).

Buerkle et al., "Comparison of the spinal actions of the $\mu$–opioid remifentanil with alfentanil and morphine in the rat", *Anesthesiology* 84(1):94–102 (1996).

Burkhardt et al., "Metkephamid (Tyr–D–Ala–Gly–Phe–N–(Me)Met–NH$_2$), a potent opoid peptide: Receptor binding and analgesic properties." *Peptides* 3:869–871 (1982).

Chemical Abstr. 100:17470j (1984), citing lizuka et al., "Pharmacodynamics of a new antidiarrheic nufenoxole", *Jitchuken Zenrinsho Kenkyho* 9(1): 19–41 (1983).

Chemical Abstr. 105:208764w (1986), citing DE 3,545,981 (Jul. 10, 1986).

Chemical Abstr. 111:17521d (1989), citing Shaw et al., "ICI 204448: A κ–opoid agonist with limited access to the CNS", *Br. J. Pharmacol.* 96(4): 986–992 (1989).

Chemical Abstr. 118:124404j (1993), citing EP 512,902 (May 3, 1991).

Chemical Abstr. 120:116860f (1994), citing Japanese patent JP 05,286,851 (Nov. 2, 1993).

Chemical Abstr. 120:289632 (1994), citing Park et al., "Pain reducing effects of 4–amino and 4–(1–piperazinyl)phenacetamide derivatives", *Korean J. Med. Chem.* 3(2): 116–123 (1993).

Chemical Abstr. 121:57079d (1994), citing Park et al., "Synthesis of caspicinoids: 3–nitrogen–substituted phenylacetamides", *Korean J. Med. Chem.* 3(2): 142–147 (1993).

Chemical Abstr. 123:22673g, citing Park et al., KR–25003, "a potent analgesic capsaicinoid", *Acta Crystallogr. Sect. C: Cryst. Struct. Comm.* C51(5): 927–929 (1995).

Chemical Abstr. 123:256289p, citing Lee et al., "Synthesis of phenylacetamides and their analgeisc activities", *Korean J. Med. Chem.* 5(1): 6–12 (1995).

Chemical Abstr. 80:82443k (1974), citing U.S. 3,789,072.

Chemical Abstr. 82:156117x (1975), citing Ger. Offen. DE 2,440,541 (Mar. 6, 1975).

Chemical Abstr. 84: 44072p (1976), citing Ger. Offen. DE 2,514,229 (Oct. 9, 1975).

Chemical Abstr. 84:44071n (1976), citing Ger. Offen. DE 2,514,183 (Oct. 9, 1975).

Chemical Abstr. 84:44072p (1976), citing Ger. Offen. DE 2,514,229 (Oct. 9, 1975).

Chemical Abstr. 85:116541m, citing Adelstein et al., "3,3–Diphenyl–3–(2–alkyl–1,3, 4–oxadiazol–5–yl)propylcycloalkylamines, a novel series of antidiarrheal agents", *J. Med. Chem* 19(10): 1221–1225 (1976).

Chemical Abstr. 96:20297n (1982), citing Belgian Patent BE 886,579 (Jun. 10, 1981).

Cortes, et al., Tape stripping–induced hyperalgesia as a model for the evaluation of analgesic agents, *Soc. Neurosci. Abstr.*, 22:1315 (1996).

Craft, R.M., et al., "Opioid Antiociception in a Rat Model of Visceral Pain: Systemic Versus Local Drug Administration," 275:1535–1542, (1995).

D'Amour et al., "A method for determining loss of pain sensation." *J. Pharmacol. Exp. Ther.* 72:74 (1941).

Dajani et al., "Effects of E prostaglandins, diphenoxylate and morphine on intestinal motility in vivo." *Eur. J. Pharmacol.* 34:105–113 (1975).

Dajani et al., "The pharmacology of SC–27166: A novel antidiarrheal agent." *J. Pharmacol. Exp. Ther.* 203:512–526 (1977).

Dashwood et al., "Autoradiographic demonstration of [$^3$H] loperamide binding to opoid receptors in rat and human small intestine." *The International Narcotics Research Conference (INRC) '89*, Alan R. Liss, Inc., pp. 165–169 (1990).

DeHaven–Hydkins et al., ADL 2–1294, a peripherally selective opiate analgesic, *Society for Neuroscience Abstracts 22 (1–3)*: 1362 (1996).

Dickenson, Neurophysiology of opioid poorly responsive pain, *Cancer Surveys* 21:5–16 (1994).

Dixon, The up–and–down method for small samples, *Am. Stat. Assoc. J.* 60:967–978 (1965).

Dubner et al., "Spinal dorsal horn plasticity following tissue or nerve injury." In, *Textbook of Pain*, Melzack et al., eds., Churchill–Livingstone, London, pp. 225–242 (1994).

Dubuisson, et al., The formalin test: A quantitative study of the analgesic effects of morphine, meperidine, and brain stem stimulation in rats and cats, *Pain*, 4:161–174 (1977).

Enk et al., "Early molecular events in the induction phase of contact sensitivity", *Proc. Natl. Acad. Sci USA* 89:1398–1402 (1992).

Ercoli et al., "I. The Time–Action Curves of Morphine, Codeine, Dilaudid and Demerol by Various Methods of Administration. II. Analgesic Activity of Acetylsalicylic Acid and Aminopyrine." *J. Pharmacol. Exptl. Therap.* 84:301 (1945).

Ferreira et al., "Prostaglandin hyperalgesia: The peripheral analgesic activity of morphine, enkephalins and opioid antagonists." *Prostaglandins* 73:191–200 (1979).

Frederickson, "Animal and human analgesic studies of metkephamid." *Advances in Pain Research and Therapy, vol. 8*, Foley and Inturrsi, Eds., Raven Press, New York pp. 293–301 (1986).

Frederickson et al., "Metkephamid, a systemically active analogue of methionine enkephalin with potent opioid δ–receptor activity." *Science* 211:603–605 (1981).

Gamse, "Capsaicin and nociception in the rat and mouse." *Naunyn–Schmiedeberg's Arch. Pharmacol.* 320:205–216 (1982).

Gasbarrini, G., et al., "Multicenter Double–blinded Controlled Trial Comparing idamidine HCl and Loperamide in the Symptomatic Treatment Acute Diarrhoea," *Drug Res.* 36:1843–1845.

Gesellchen et al., "Structure–activity relationships of enkephalin analogs." *Peptides: Synthesis, structure, function and processing. American Peptide Symposium, 7th*, Rich and Gross, Eds., Pierce Chemical Co., Rockford, Ill. pp. 621–624 (1981).

Giagnoni et al., "Loperamide: Evidence of interaction with μ and δ opid receptors." *Life Sci.* 33(*Suppl. 1*):315–318 (1983).

Giardina, et al., Central and peripheral analgesic agents: chemical strategies for limiting brain penetration in kappa–opioid agonists belonging to different chemical classes, *II Farmaco* 50(6):405–18 (1995).

Goodman et al., *The pharmacological basis for therapeutics*, McMillian, New York, NY, pp. 505–517 (1985).

Gottschlich et al., "The peripherally acting κ–opiate agonist EMD 61753 and analogues: opioid activity versus peripheral selectivity", *Drugs Exptl. Clin. Res.* XXI(5):171–174 (1995).

Handwerker et al., "Pain and Inflammation." *Proceedings of the VIth World Congress on Pain, Chapter 7*, Bond, et al., Eds., Elsevier Science Publishers BV, Amsterdam, pp. 59–70 (1991).

Hertz, Role of Immune Processes in Peripheral Opioid Analgesia, *The Brain Immune Axis and Substance Abuse*, Plenum Press, New York (1995).

Heykants, et al., Loperamide (R 18 553), a novel type of antidiarrheal agent, *Arzneim.–Forsch. Drug Res.*, 24:1649–1653 (1974).

Hurwitz, A., et al., "Lopermide effects on hepatobiliary function, intestinal transit and analgesia in mice," *Life Sciences*, 54:1687–1698, (1994).

Jaffe et al., "Abuse potential of loperamide." *Clin. Pharmacol. Ther.* 28(6):812–819 (1980).

James et al., "Naloxazone Treatment in the Guinea Pig Ileum in Vivo Reveals Second Functional Opioid Receptor Site." *J. Pharmacol Exp. Ther.* 240:138–144 (1987).

Kaminer, et al., The many faces of acne, *J. Am. Acad. Dermatol.* 32(5):S6–14 (1995).

Keita, Hawa, et al., "Antinociceptive effect of a κ–opioid receptor agonist that minim?. Crosses the blood–brain barrier (ICI 204448) in a rat model of mononeuropathy," *Eur. J. of Pharmacol.* 277:275–280, (1995).

Kinnman, et al., Peripherally administered morphine attenuates capsaicin–induced mechanical hypersensitivity in humans, *Anesth. Analg.* 84:595–9 (1997).

Koo, The psychosocial impact of acne: Patients' perceptions, *J. Am. Acad. Dermatol.* 32(5):S26–30 (1995).

Kosterlitz et al., *Br. J. Pharmacol.* 33:266–276 (1968).

Lee, Buyean, et al., "RK–25018: A Novel, Orally Active Analgesic with Non–narotic Properties," *Arch. Pharm. Res.*, 17:5:304–308, (1994).

Levine et al., "Involvement of the mu–opiate receptor in peripheral analgesia." *Neurosci.* 32(3):571–575 (1989).

Mackerer et al., "Antidiarrheal and central nervous system activities of SC–277166 (2–[3–5–methyl–1,3, 4–oxadiazol–2–yl–3,3–diphenylpropyl]–2–azabicyclo [2.2.2]octane), a newantidiarrheal agent, resulting from binding to opiate receptor sites of brain and myenteric plexus." *J. Pharmacol. Exper. Ther.* 203(1):527–538 (1977).

Mackerer et al., Loperamide binding to opiate receptor sites of brain and myenteric plexus. *J. Pharmacol. Exp. Ther.* 199:131–140 (1976).

Mackerer et al., Review of the involvement of opiate receptors in producing the central and peripheral effects caused by two new antidiarrheal drugs, loperamide and SC–27166. *J. Am. Coll. Toxicol.* 3:81–91 (1984).

Makman, Morphine receptors in imunocytes and neurons, *Advances in Neuroimmunology* 4:69–82 (1994).

Mather, Opioids: A pharmacologist's delight!, *Clinical and Experimental Pharmacology and Physiology* 22:833–36 (1995).

Megens et al., Is in vivo association between the antipropulsive and antidiarrheal properties of opioids in rats related to gut selectivity? *Arch. Int. Pharmacodyn. Ther.* 298:220–229 (1989).

Megens et al., Normalization of small intestinal propulsion with loperamide–like antidiarrheals in rats. *Eur. J. Pharmacol.* 178:357–364 (1990).

Mir, G.N., et al., "In vivo anitmotility and antidiarheal activity of lidamidine hydrochloride (WHR–1142A), a novel antidiarrheal agent," *Drug Res.,* 28:(II), 1448–1480).

Moiniche, et al., Peripheral antinociceptive effects of morphine after burn injury, *Acta Anaesth. Scand.*, 37:710–712, 1993.

Molina et al., The peripheral analgesic effect of morphine, codeine, pentazocine and D–propoxyphene, *Brazilian J. Med. Biol. Res.* 16: 345–352 (1983).

Nagasaka et al., Peripheral and spinal actions of opioids in the blockade of the autonomic response evoked by compression of the inflamed knee joint. *Anesthesiol.* 85:808–816 (1996).

Needham, Painless lumbar surgery: morphine nerve paste, *Connecticut Medicine* 60(3):141–43 (1996).

Neugebauer et al., "N–Methyl–D–Aspartate (NMDA) and Non–NMDA Receptor Antagonists Block the Hyperexcitability of Dorsal Horn Neurons During Development of Acute Arthritis in Rat's Knee Joint." *J. Neurophysiol.* 70(4):1365–1377 (1993).

Nguyen, et al., Management of acne vulgaris, *American Family Physician* 50(1):89–96 (1994).

Niemegeers et al., Dissociation between opiate–like and antidiarrheal activities of antidiarrheal drugs. *J. Pharmacol. Exp. Ther.* 203:527–538 (1979).

Niemegeers et al., Loperamide (R 18 533), a novel type of antidiarrheal agent, *Arzneim.–Forsch.(Drug Res.)* 24(10): 1633–1641 (1974).

Nogrady, *Medicinal Chemistry: A Biochemical Approach*, Oxford Univ. Press, New York, pp 388–392 (1985).

Oluyomi, et al., Differential antinociceptive effects of morphine and methylmorphine in the formalin test, *Pain*, 49:415–418 (1992).

Osborne, Richard, et al., "Analgesic Activity of Morphine–6–Glucuronide," *The Lancet*, :828, (1988).

Park, No–Sang, et al., "KR–25003, a Potent Analgesic Capsaicinoid," *Acta Crystallographica* C51:927–929 (1995).

Paul, Dennis, et al., Pharmacological Characterization of Morphine–66–Glucuronide, a Very Potent Morphine Metabolite[1], *The Journal of Pharmacology and Experimental Therapeutics*, 251:477–483, (1989).

Peyman, et al., Effects of morphine on corneal sensitivity and epithelial wound healing: Implications for topical ophthalmic analgesia, *British Journal of Ophthalmology* 78:138–41 (1994).

Peyman et al., Effects of morphine on corneal sensitivity and epithelial wound healing: implications for topical ophthalmic analgesia, *Brit. J. Ophthalmol.* 78: 138–141 (1994).

Porreca et al., "Roles of Mu, Delta and Kappa Opioid Receptors in Spinal and Supraspinal Mediation of Gastrointestinal Transit Effects and Hot–Plate Analgesia in the Mouse." *J. Pharmacol. Exp. Ther.* 230(2):341–348 (1984).

Randall et al., "A method for measurement of analgesic activity on inflamed tissue." *Arch. Int. Pharmacodyn.* 111(4):409–419 (1957).

Reinstein et al., "Suppression of lipopolysaccharide–stimulated release of tumor necrosis factor by adenosine: Evidence of $A_2$ receptors on kat kupffer cells", *Hepatology* 19(6):1445–1452 (1994).

Rogers, et al., GR94839, a κ–opioid agonist with limited access to the central nervous system, has antinociceptive activity, *J. Pharmacol.*, 106:783–789 (1992).

Russell et al., "Opiates inhibit the discharges of fine afferent units from inflamed knee joint of the cat." *Neurosci. Lttrs.* 76:107–112 (1987).

Sasaki, Yusuke, et al., "Synthesis and Biological Properties of Quaternized N–Methylation Analogs of D–Arg–2–Dermorphin Tetrapeptide," *Bioorganic & Medicinal Chemistry Letters*, 4:2049–2054, (1994).

Sato et al., "Changes in blood pressure and heart rate induced by movements of normal and inflamed knee joints." *Neurosci. Lett.* 52:55–60 (1984).

Sato et al., Catecholamine secretion and adrenal nerve activity in response to movements of normal and inflamed knee joints in cats, *J. Physiol.* 375: 611–624 (1986).

Schafer, et al., Inflammation enhances peripheral $\mu$–opioid receptor–mediated analgesia, but not $\mu$–opioid receptor transcription in dorsal root ganglia, *Eur. J. Pharmacol.*, 279:165–169 (1995).

Schaible et al., "Afferent and spinal mechanisms of joint pain." *Pain* 55:5–54 (1993).

Schaible et al., "Effects of an experimental arthritis on the sensory properties of fine articular afferent units." *J. Neurophysiol.* 54(5):1109–1122 (1985).

Schinkel, et al., P–Glycogprotein in the blood–brain barrier of mice influences the brain penetration and pharmacological activity of many drugs, *Br. J. Clin. Invest.*, 97:2517–2524 (1996).

Shaw, John S., "ICI 204448: aκ–opioid agonist with limited access to the CNS," *Br. J. Pharmacol.* 96:986–992, (1989).

Shriver et al., "Loperamide." *Pharmacological and Biochemical Properties of Drug Substances*, vol. 3, Goldberg, Ed., American Pharmaceutical Ass'n Press pp. 461–476 (1981).

Smith et al., "Peripheral antinociceptive effects of N–methyl morphine", *Life Sciences* 31(12 & 13):1205–1208 (1982).

Solomon, et al., Effects of detergents on acne, *Clinics in Dermatology* 14:95–99 (1996).

Stahl et al., "Receptor affinity and pharmacological potency of a series of narcotic analgesic, anti–diarrheal and neuroleptic drugs." *Eur. J. Pharmacol.* 46:199–205 (1977).

Stein, "Peripheral analgesic actions of opioids", *J. Pain and Sympt Mgmt.* 6(3):119124 (1991).

Stein, "Peripheral mechanisms of opoid analgesia." *Anesth. Analg.* 76:182–191 (1993).

Stein, "Peripheral opioid receptors", *Ann Med* 27:219–221 (1995).

Stein et al., "Analgesic effect of intraarticular morphine after arthroscopic knee surgery." *New Eng. J. Med.* 325(16):1123–1126 (1991).

Stein et al., "Peripheral opoid receptors mediating antinociception in inflammation. Evidence for involvement of Mu, Delta and Kappa receptors." *J. Pharmacol. Exp. Ther.* 248(3):1269–1275 (1989).

Stein, et al., Antinociceptive effects of $\mu$– and $\kappa$–agonists in inflammation are enhanced by a peripheral opioid receptor--specific mechanism, *European Journal of Pharmacolog* 3:255–64 (1988).

Stein, et al., No tolerance to peripheral morphine analgesia in presence of opioid expression in inflamed synovia, *J. Clin. Invest.* 98(3):793–99 (1996).

Stein, et al., Opioids as novel intra–articular agents in arthritis, *Progress in Pain Research and Management* 1:289–96 (1994).

Stein, et al., Peripheral effect of fentanyl upon nociception in inflamed tissue of the rat, *Neurosci. Lett.*, 84:225–228 (1988).

Stein, et al., Unilateral inflammation of the hindpaw in rats as a model of prolonged noxious stimulation: Alterations in behavior and nociceptive thresholds, *Pharmacol. Biochem. Behav.*, 31:445–451 (1988).

Stokbroekx et al., Synthetic antidiarrheal agents: 2,2–diphenyl–4–(4'–aryl–4'–hydroxypiperidino)butyramides, *J. Medicinal Chem.* 16(7): 782–786 (1973).

Sykes, et al., Acne: A review of optimum treatment, *Drugs* 48(1):59–70 (1994).

Takasuna et al., "Opoid pharmacology of the antinociceptive effects of loperamide in mice." *Behav. Pharmacol.* 5:189–195 (1994).

Tallarida et al., *Manual of Pharmacologic Calculations with Computer Programs*, 2nd Ed., New York, Springer–Verlag, pp. 7–18, (1986).

Thompson, D., et al., "Local Analgesia with Opiod Drugs", *The Annals of Pharmacotherapy*, 29:189–190, (1995).

Tjolsen, et al., The formalin test: an evaluation of the method, *Pain*, 51:5–17 (1992).

Traynor, Critique: Opioid receptors and their subtypes: focus on peripheral isolated tissue preparations, *Neurochem. Int.* 24(5):427–32 (1994).

van Joost et al., "Cyclosporine in atopic dermatitis", *J. Amer Acad of Derm.* 27(6):922–928 (1992).

Van der Kooy, Hyperalgesic functions of peripheral opiate receptors. *Ann. N.Y. Acad. Sci.* 467:154–168 (1986).

Wheeler–Aceto et al., Characterization of nociception and edema after formalin–induced tissue injury in the rat: Pharmacological analysis of opioid activity, *UMI Dissertaion Services* pp. 321–336; 398–406, (1995).

Williams et al., "CD28–stimulated IL–2 gene expression in Jurkat T cells occurs in part transcriptionally and is cyclosporine–A sensitive[1]", *J. of Immun.* 148:2609–2616 (1992).

Williamson et al.. "Reflex increase in blood pressure induced by leg compression in man." *J. Physiol.* 475(2):351–357 (1994).

Winter et al., "Nociceptive thresholds as affected by parenteral administration of irritants and of various antinociceptive drugs." *J. Pharm. Exp. Ther.* 148(3):373 (1965).

Woolf et al., "Preemptive Analgesia—Treating Postoperative Pain by Preventing the Establishment of Central Sensitization." *Anesth. Analg.* 77:362–79 (1993).

Woolf et al., "The induction and maintenance of central sensitization is dependent on N–methyl–D–aspartic acid receptor activation; implications for the treatment of post–injury pain hypersensitivity states." *Pain* 44:293–299 (1991).

Wuster, Michael, et al., "Opiate Agonist Action of Antidiarrheal Agents in vitro and in vivo—Findings in Support for Selective Action," *Archives of Pharmacology*, 301:187–194, (1987).

Yaksh, "Multiple opioid receptor systems in brain and spinal cord: Part I." *Eur. J. Anaesthesiol.* 1:171–199 (1984).

Yaksh, "The spinal actions of opoids." *Handbook of Experimental Pharmacology, vol. 104/II Opoids II, Chapter 33*, Herz, Ed., Springer–Verlag, Berlin and Heidelberg, pp. 53–90 (1993).

Yaksh, "The spinal pharmacology of facilitation of afferent processing evoked by high–threshold afferent input of the postinjury pain state." Current Opinion in Neurology and Neurosurgery, *Current Science* 6:250–256 (1993).

Yaksh et al., "Brief Communication. Chronic Catherization of the Spinal Subarachnoid Space." *Physiol. Behav.* 17:1031–1036 (1976).

Yaksh et al., "Sites of action of opiates in production of analgesia." In, *Progress in Brain Research*, vol. 77, Chap. 28, Elsevier Science Pub., B.V., pp. 371–394 (1988).

Zerbe et al., "A new Met–enkalphin analogue suppresses plasma vasopressin in man." *Peptides* 1:199–201 (1982).

PERIPHERALLY ACTIVE ANTI-HYPERALGESIC OPIATES

RELATED APPLICATIONS

This application is continuation of allowed U.S. application Ser. No. 08/528,510, filed Sep. 12, 1995 to Yaksh, entitled PERIPHERALLY ACTIVE ANTI-HYPERALGESIC OPIATES, now U.S. Pat. No. 5,849,761.

The subject matter of U.S. application Ser. No. 08/528,510 is incorporated by reference in its entirety. All patents and publications referred to herein are, unless noted otherwise, incorporated by reference in their entirety.

FIELD OF THE INVENTION

The present invention relates to compositions and methods for treatment of hyperalgesic states. The compositions, which are formulated for topical and local administration, contain anti-hyper-algesics that have substantially no central nervous system side effects, and, thus, no potential for abuse.

BACKGROUND OF THE INVENTION

Pain and analgesia

Pain has been defined in a variety of ways. For example, pain can be defined as the perception by a subject of noxious stimuli that produces a withdrawal reaction by the subject. The most commonly experienced form of pain may be defined as the effect of a stimulus on nerve endings, which results in the transmission of impulses to the cerebrum. This somatic sensation and normal function of pain, referred to as nociception or nociceptive pain, informs the organism of impending tissue damage. Somatic and visceral free nerve endings, termed nociceptors, initially process such pain signals.

Despite numerous definitions, the brain pathways governing the perception of pain are not completely understood. Sensory afferent synaptic connections to the spinal cord, so-called "nociceptive pathways", however, have been documented in some detail. The nociceptive pathway, which exists for protection of the organism (such as the pain experienced in response to a burn), is inactive. Activity is initiated by the application of a high intensity, potentially damaging stimulus. This stimulus serves to depolarize certain classes of afferent (sensory) axons of the small unmyelinated category, designed C fibers.

The signal carried by the C fibers travels up the peripheral nerve and into the spinal cord where synapses are made on second order and higher order neurons, which then transmit the pain signal up the spinal cord in the spinothalamic tract ending in the thalamus. Polysynaptic junctions in the dorsal horn of the spinal cord are involved in the relay and modulation of sensations of pain to various regions of the brain, including the periaqueductal grey region. The ventrolateral and ventromedial thalamic nuclei project to the cortex where the pain is then processed with regard to localization and other integrative characteristics.

Opioid Analgesia

Analgesia, or the reduction of pain perception, can be effected directly by decreasing transmission along such nociceptive pathways.

Analgesic opiates are thought to act by mimicking the effects of endorphin or enkephalin peptide-containing neurons, which synapse presynaptically at the C-fiber terminal and which, when they fire, inhibit release of substance P from the C-fiber. Descending pathways from the brain are also inhibitory to C-fiber firing. Thus, CNS-mediated analgesia leads to an overall inhibition of the pain transmission.

Agents that selectively block an animal's response to a strong stimulus without obtunding general behavior or motor function is referred to as an analgesic. Opiates, via interaction with specific receptors in the brain and spinal cord, are able to block the release of transmitters from central terminals (Yaksh et al. (1988) In: *Progress in Brain Research*, Vol. 77, Chapter 28, Elsevier Science Pub., B.V. pp. 371–94)). They are thus able to increase the intensity of the peripheral stimulus necessary to produce a given pain state. Accordingly, these agents are referred to as analgesics.

Opiates receptors and opiate side effects

Central opiate receptors (in brain and spinal cord) appear to mediate the effects of systemically administered opiates. Three principal classes of opiate receptors have been identified: $\mu$, $\kappa$ and $\delta$ (Yaksh, T. L.: *Eur. J. Anaesthesiol.* 1:201–243, 1984). The use of selective agonists and antagonists have demonstrated that these receptors also appear to mediate peripheral opioid effects. The central and peripheral actions activities of opiates are an important component of their therapeutic utility. It appears that after systemic delivery of opiates such as morphine, the primary effect may be mediated by both sites of action.

On the other hand, many of the principal drawbacks of systemic opiates are the results of their actions within the brain. These actions include sedation, depression of respiration, constipation, nausea and emesis, abuse liability and the development of addiction (Yaksh, *Eur. J. Anaesthesiol.* 1:171–199, 1984). These side effects serve to limit the utility of opiates for controlling post injury pain. Addiction liability can occur secondary to medical uses of the drug where the central effects lead to an addicted and dependent state.

Because constipation is among the actions of opiates, many agents selected for anti-diarrheal activity, such as 2,2-diphenyl-4-[(4-carbethoxy-4-phenyl)piperidino) butyronitrile, generically known as diphenoxylate, act via one or more of these opioid receptors. Because of the diverse actions mediated by opioid receptors, such agents also have undesirable central nervous system effects and abuse potential. Because of these diverse activities and the potential for abuse, anti-diarrheal opioid drug development has been directed towards identifying compounds in which the potentially beneficial activities are separated from the activities that lead to abuse and dependence.

During the mid to late 1960's, several agents derived from classes of molecules known to have opioid activity were synthesized. These agents were shown to have naloxone reversible suppressant effects in smooth muscle bioassays and were able to readily displace opioid ligands in receptor binding assays. These results indicated that they act via direct or indirect action with opioid receptors. These compounds were designed to be selective anti-diarrheal opioid receptor (believed to be the $\mu$ receptor) agonists that are substantially free from analgesic and habit-forming activities (see, e.g., Shriver et al. (1987) "Loperamide" in *Pharmacological and Biochemical Properties of Drug Substances*, Vol. 3, Goldberg, M. E., ed. Am. Pharm. Assoc., Washington, D.C., p. 462).

Compounds, such as loperamide (4-(p-chlorophenyl)-4-hydroxy-N-N-dimethyl-$\alpha$,$\alpha$-diphenyl-1-piperidinebutyramide hydrochloride), and its analogs were among those synthesized. Loperamide was widely reported to be completely devoid of analgesic effects and CNS effects (see, e.g., Jaffe et al. (1980) *Clin. Pharmacol. Ther.* 80:812–819) even at relatively high dosages. Subsequent work has demonstrated certain analgesic effects of intraparenterally administered loperamide (see, e.g., Takasuna et al. (1994) *Behavioural Pharm.* 5:189–195), but none or questionable CNS effects have been demonstrated.

In contrast to conventional opiates, however, loperamide and analogs thereof and other such agents exhibit little or no analgesic effects as measured in acute pain models, such as the tail clip and hot plate tail withdrawal tests, when given systemically (see, e.g., Stahl et al. (1977) *Eur. J. Pharmacology* 46:199–205; Shriver et al. (1981) "Loperamide" in *Pharmacological & Biochemical Properties of Drug ubstances* Vol. 3, Goldenberg, Ed., American Pharmaceutical Assn. Press, pp. 461–476; see, also U.S. Pat. No. 3,714,159 and U.S. Pat. No. 3,884,916). This absence of CNS effects, including analgesic effects, is believed to be related to the failure of such compounds to cross the blood brain barrier. This failure is in part due to the extremely high lipid partition coefficient of the compounds. The high partition coefficient results in sequestration of the compound in the lipid membrane. This local absorption is thought to contribute to its failure to cross the blood brain barrier. In support of this conclusion, antinociceptive analgesic action has been observed after direct delivery into the brain (Stahl et al. (1977) *Eur. J. Pharmacology* 46:199–205).

Peripheral injury and hyperalgesia.

Changes in the milieu of the peripheral sensory terminal occur secondary to local tissue damage. Mild damage (such as abrasions or burns) and inflammation in the cutaneous receptive fields or joints will produce significant increases in the excitability of polymodal nociceptors (C fibers) and high threshold mechanoreceptors (Handwerker et al. (1991) *Proceeding of the VIth World Congress on Pain*, Bond et al., eds., Elsevier Science Publishers BV, pp. 59–70; Schaible et al. (1993) *Pain* 55:5–54). This increased excitability leads to increased spontaneous activity (in otherwise silent sensory afferents) and an exaggerated response to otherwise minimal stimuli.

These events have several consequences. First, the magnitude of the pain state in humans and animals is proportional to the discharge rate in such sensory afferent (Raja et al. (1988) *Anesthesiology* 68:571–590). The facilitated response secondary to the local peripheral injury may lead to an exaggerated pain state simply because of the increased afferent activity. Secondly, spontaneous activity in small sensory afferent causes central neurons in the spinal cord to develop an exaggerated response to subsequent input (Woolf et al. (1991) *Pain* 44:293–299; Neugebauer et al. (1993) *J. Neurosci.* 70:1365–1377). Both of these events, secondary to the increased spontaneous activity and reactivity in small sensory afferents generated by the peripheral injury leads to a behavioral state referred to as hyperalgesia (Yaksh, T. L., (1993) *Current Opinion in Neurology and Neurosurgery* 6:250–256).

Thus, in the instance where the pain response is the result of an exaggerated response to a given stimulus, the organism is hyperalgesic. The importance of the hyperalgesic state in the post injury pain state has been repeatedly demonstrated and this facilitated processing appears to account for a major proportion of the post-injury/inflammatory pain state (see, e.g., Woold et al. (1993) *Anesthesia and Analgesia* 77:362–79; Dubner et al. (1994) In, *Textbook of Pain*, Meizack et al., eds., Churchill-Livingstone, London, pp. 225–242).

Certain drug actions may serve to normalize the sensitivity of the organism. Experimental investigations have shown that opiates with an action in the vicinity of the peripheral terminal in injured or inflamed tissue will normalize the activity in afferent innervating inflamed skin (Russell et al. (1987) *Neurosci. Lett* 76:107–112; Andreev et al. (1994) *Neurosci.* 58:793–798) and normalize the hyperalgesic threshold (Stein (1988) *Eur. J. Pharmac.* 155:255–264 Stein (1993) *Anesth. Analg.* 76:182–191). Opiates, such as morphine, however, when peripherally applied, have a short duration of action and possibly can, if applied at sufficient levels, have effects upon consciousness and respiration. The possible systemic effects, CNS effects and abuse potential render conventional opioids unsuitable for local application and unsuitable as peripheral anti-hyperalgesics. Thus, there is a need for effective anti-hyperalgesics that directly block peripheral sensitization, but that do not have concomitant central nervous system (CNS) effects, including the potential for abuse.

Therefore, it is an object herein to provide anti-hyperalgesics for local and topical application minimal or no CNS effects.

SUMMARY OF THE INVENTION

Methods for treatment of peripheral local inflammatory states, including, but not limited to, inflammation following local infection, blister, boils, or acute skin injuries, such as abrasions, burns, superficial cuts, surgical incisions, contusions, irritations, inflammatory skin conditions, including but not limited to poison ivy, and allergic rashes and dermatitis, insect stings and bites, joint inflammation, and any condition that yields a hyperalgesic pain state are provided. These methods involve topical or local administration of compositions that contain one or more compounds that exert anti-hyperalgesic activity via peripheral opiate receptors, but that do not exhibit CNS, CNS-mediated analgesic or systemic effects (particularly CNS effects) at dosages at which they are topically or locally applied. The intended locus of application includes, but is not limited to, any body surface or part that is amenable to local or topical treatment. Such body parts include, but are not limited to: the skin, joints, eyes, lips and mucosal membranes.

The methods use compositions containing opioid anti-diarrheal compounds or other opiate receptor agonist compounds that do not, upon topical or local administration, evoke CNS effects, as defined herein, particularly at the peripheral anti-hyperalgesic dosage. The compositions that contain the opioid anti-diarrheal compounds or other opiate receptor compounds are also provided.

Typically the compounds intended for use in the compositions and methods herein possess peripheral anti-hyperalgesic and substantially no CNS activities, as defined herein, because they do not cross the blood brain barrier. The failure to cross the blood brain barrier precludes the occurrence of the CNS systemic side effects, so that there is no potential for abuse. Other opioids, such as morphine, that readily cross the blood brain barrier could be effective as anti-hyperalgesics, but their permeability through the blood brain barrier results in abuse liability. Their scheduling by the Drug Enforcement Agency limits their applicability.

In contrast, the compositions provided herein, contain opioids that do not, upon topical or local administration, substantially cross the blood brain barrier as assessed by assays described herein. The compounds intended for use in the methods and compositions provided herein include any compound that by virtue of its interaction, either directly or indirectly, with peripheral opioid receptors ameliorates the peripheral hyperalgesic state, but does not exhibit systemic CNS-mediated analgesic activity (i.e., analgesic activity by virtue of interaction with CNS opioid receptors) or CNS side-effects, including heaviness of the limbs, flush or pale complexion, clogged nasal and sinus passages, dizziness, depression, respiratory depression, sedation and constipation. These compounds include anti-diarrheals that act as anti-diarrheals via interaction with μ, δ or κ receptors, and opiate agonists, such as metkephamide and related enkephalin analogs. Examples of such compounds include, but are not limited to:

(i) loperamide (4-(p-chlorophenyl)-4-hydroxy-N-N-dimethyl-α,α-diphenyl-1-piperidinebutyramide hydrochloride)), loperamide analogs and related compounds as defined herein (see, Formula (I); see, also, U.S. Pat. Nos. 3,884,916, 3,714,159; see, also U.S. Pat. Nos. 4,194,045, 4,116,963, 4,072,686, 4,069,223, 4,066,654,), N-oxides of loperamide and analogs, metabolites and prodrugs thereof and related compounds as defined herein (see, also, U.S. Pat. No. 4,824,853), and related compounds, such as (a), (b) and (c) as follows:

(a) 4(aroylamino)piperidine-butanamide derivatives and N-oxides thereof as defined herein (see, also U.S. Pat. No. 4,990,521);

(b) 5-(1,1-diphenyl-3-(5- or 6-hydroxy-2-azabicyclo-(2.2.2)oct-2-yl)propyl)-2-alkyl-1,3,4-oxadiazoles, 5-(1,1-diphenyl-4-(cyclic amino)but-2-trans-en-1-yl)-2-alkyl-1,3,4-oxadiazoles, 2-[5-(cyclic amino)-ethyl-10,11-dihydro-5H-dibenzo[a,d]-cyclohepten-5-yl]-5-alkyl-1,3,4-oxadiazoles) and related compounds (see, U.S. Pat. Nos. 4,013,668, 3,996,214 and 4,012,393);

(c) 2-substituted-1-azabicyclo[2,2,2]octanes (see, U.S. Pat. No. 4,125,531);

(ii) certain phenylacetamide derivatives (see, U.S. Pat. No. 5,242,944), including, but not limited to N-{(3,4-dimethylphenyl)propyl}-4-(2-aminoethoxy)-3-methoxy-phenylacetamide, N-{(3,4-dimethylphenyl)propyl)-4-(2-aminoethoxy)-3-hydroxy-phenylacetamide, N-{(3,4-dimethylphenyl)propyl}-4-(2-aminoethoxy)-3-aminophenylacetamide, N-{(3-methylphenyl)propyl}-4-(2-aminoethoxy)-3-methoxy-phenylacetamide, N-{(3-methylphenyl)propyl}-4-(2-aminoethoxy)-3-hydroxy-phenylacetamide and N-{(3-dimethylphenyl)propyl}-4-(2-aminoethoxy)-3-amino phenylacetamide;

(iii) 3-hydroxy-7-oxomorphinans and 3-hydroxy-7-oxoisomorphinans (see, U.S. Pat. No. 4,277,605) including, but not limited to: 3-hydroxy-7-oxomorphinan and 3-hydroxy-7-oxoisomorphinans including d,l-3-hydroxy-7-oxo-N-methylmorphinan, l-3-hydroxy-7-oxo-N-methylmorphinan, d,l-3-hydroxy-7-oxomorphinan, l-3-hydroxy-7-oxomorphinan, d,l-3-hydroxy-7-oxo-N-methylisomorphinan, l-3-hydroxy-7-oxo-N-methylisomorphinan, d,l-3-hydroxy-7-oxoisomorphinan and l-3-hydroxy-7-oxoisomorphinan;

(iv) amidinoureas as provided herein (see, also U.S. Pat. Nos. 4,326,075, 4,326,074, 4,203,920, 4,060,635, 4,115,564, 4,025,652) and 2-[(aminophenyl and amidophenyl)amino]-1-azacycloalkanes (see, U.S. Pat. No. 4,533,739);

(v) metkephamid (Tyr-D-Ala-Gly-Phe-N(ME)Met-NH$_2$; see, e.g., U.S. Pat. No. 4,430,327; Burkhart et al. (1982) *Peptides* 3:869–871; Fredrickson et al. (1991) *Science* 211:603–605) and other synthetic opioid peptides, such as H-Tyr-D-Nva-Phe-Orn-NH$_2$, H-Tyr-D-Nle-Phe-Orn-NH$_2$, H-Tyr-D-Arg-Phe-A$_2$bu-NH$_2$, H-Tyr-D-Arg-Phe-Lys-NH$_2$, and H-Lys-Tyr-D-Arg-Phe-Lys-NH$_2$ (see, U.S. Pat. No. 5,312,899; see, also Gesellchen et al. (1981) *Pept.: Synth., Struct., Funct., Proc. Am. Pept. Symp., 7th,*; Rich et al. (Eds), Pierce Chem. Co., Rockford, III, pp. 621–62) that do not cross the blood brain barrier;

(vi) propanamines as defined in U.S. Pat. No. 5,236,947; and (vii) other opioid compounds that agonize peripheral μ or κ receptors, but that, upon topical or local administration, do not cross the blood brain barrier and do not exhibit CNS effects as defined herein.

Preferred compounds for use in the compositions and methods herein are the loperamide analogs and N-oxides, preferably an N-oxide of a piperidine-nitrogen, thereof or other pharmaceutically acceptable derivatives thereof and related compounds (see (i), above). These preferred compounds include compounds of formula (I):

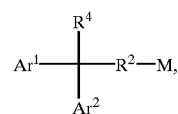

where M is

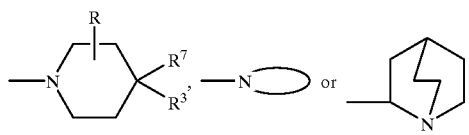

in which:

is an azabicycloalkyl containing from 6 to 9 carbon atoms with at least 5 atoms in each ring, is preferably:

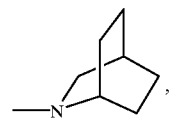

and is unsubstituted or substituted with $OR^{18}$ in which $R^{18}$ is hydrogen or lower alkanoyl containing 2 to 7, preferably 2 or 3, carbon atoms, and $OR^{18}$ is preferably attached at the 5 position in 5-membered rings or the 5 or 6 position in 6-membered rings and is attached in the endo or exo configuration;

$Ar^1$ and $Ar^2$ are either (i) or (ii) as follows:

(i) each is independently selected from aryl and heteroaryl groups containing from 5 to 7 members in the ring, preferably phenyl and pyridyl, and each is unsubstituted or substituted with one or more, preferably up to three substituents, preferably selected from halo, hydroxy, haloalkyl, alkyl, alkyloxy, aminosulfonyl, alkylcarbonyl, nitro, haloalkyl, particularly trifluoromethyl, amino, aminocarbonyl, phenylcarbonyl that are unsubstituted or substituted with one or more, preferably up to three substituents selected from among halo, halo lower alkyl, alkyl, and thienyl that is unsubstituted or substituted with halo or alkyl, where the alkyl groups are straight or branched chains and preferably are lower alkyl containing from 1–6 carbons, more preferably 1–3 carbons; or (ii) $Ar^1$ and $Ar^2$ are each independently phenyl or pyridyl groups, preferably phenyl, and with the carbon to which they are commonly linked form a fused ring so that the compounds of formula (I) have the structure:

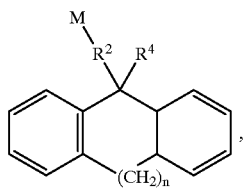

where n is 0 to 3, preferably 1 to 3, more preferably 2 or 3;

$R^2$ is either alkylene in which the alkyl group is a straight or branched chain, preferably is lower alkyl containing from 1 to 6, more preferably 1 to 3 carbons and most preferably is —$(CH_2)_2$— or —$CH_2CH(CH_3)$—, or is alkylene having 1 to 6 carbon atoms, preferably 1 to 3 carbons atoms and one or two, preferably one, double bond;

$R^3$ is $Ar^3$, —Y—$Ar^3$, where Y is alkylene or alkyl having 1 to 3 carbon atoms, or is

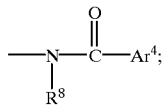

$R^8$ hydrogen or alkyl that is a straight or branched chain, preferably containing from 1 to 6, more preferably 1 to 3, carbon atoms;

$Ar^3$ is aryl or heteroaryl containing from 5 to 7 members in the ring, preferably phenyl or pyridyl, which is unsubstituted or substituted with one or more preferably, up to three substituents, preferably selected from halo, halo lower alkyl and lower alkyl;

$Ar^4$ is either:
(i) heterocycle containing one or more fused rings, preferably 1 to 3 fused rings, each of which is unsubstituted or substituted with one or more substituents selected from halo, halo lower alkyl, or lower alkyl, preferably halo, and is preferably selected from hetrocycles that include, but are not limited to, indolyl, benzofuranyl, benzothienyl, isoquinolinyl, quinolinyl, benzimidazolyl, naphthyl, thienyl, furanyl, pyridinyl, thiazolyl, imidazolyl, is more preferably thienyl, furanyl, pyridinyl, thiazolyl, imidazolyl each of which is unsubstituted or substituted with halo, halo lower alkyl, or
(ii) a radical of formula:

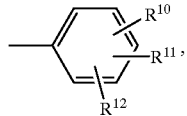

in which:
$R^{10}$, $R^{11}$ and $R^{12}$ are each independently selected from hydrogen, alkyl, alkyloxy, alkoxyalkyl, halo, hydroxy, cyano, nitro, amino, alkylamino, di(alkyl)amino, aminocarbonyl, arylcarbonylamino, alkylcarbonylamino, alkylcarbonyl, alkylcarbonyloxy, aminosulfonyl, alkylsulfinyl, alkylsulfonyl, alkylthio, mercapto, $C_{3-6}$alkenyloxy, arlyalkyloxy, aryloxy, alkyl, in which each group is unsubstituted or substituted with one or more, preferably 1 to 4 halo atoms, and the alkyl groups are straight or branched chains that are preferably lower alkyl ($C_{1-6}$) and more preferably $C_{1-3}$;

R is hydrogen, alkyl, preferably lower alkyl, or halo, OH, and is preferably at the 3-position (relative to the N), more preferably a 3-halo or 3-lower alkyl, or R is $OR^9$, which is preferably at the 3-position so that the piperidinyl ring has the formula:

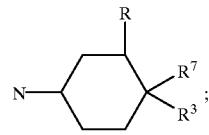

$R^9$ is selected from alkyl, arylalkyl, alkylcarbonyl, aminoalkyl, alkylaminoalkyl, dialkylaminoalkyl, in which the alkyl groups are straight or branched chains and preferably contain 1 to 12, more preferably 1 to 6 carbons, more preferably 1–3 carbons in the chain;

$R^4$ is selected from among:
(i) a 5- to 7-membered aryl group, preferably phenyl, which is unsubstituted or substituted with lower alkyl or halo or halo lower alkyl, or
(ii) a heterocyclic ring containing one to three heteroatoms, that is unsubstituted or substituted with halo, halo lower alkyl or lower alkyl, and is preferably a pyrrolidinyl, oxadiazolyl or triazolyl radical, more preferably oxadiazolyl, most preferably 1,3,4-oxadiazolyl, particularly a 5-substituted 1,3,4-oxadiazolyl in which the substituent is halo, halo lower alkyl or lower alkyl, or
(iii) alkyl containing from 1 to 8 carbons, preferably 1 to 6, more preferably 1 to 3, alkenyl containing 3 to 6 carbon atoms, cycloalkyl containing from 3 to 6 carbons, cycloalkyl alkyl in which the first alkyl contains 3 to 6 carbons and the second contains 1 to 3 carbons, or cycloalkenyl containing 4 to 7 carbons, or (iv)

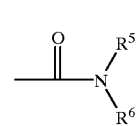

where
$R^5$ and $R^6$ are either:
(i) independently selected from hydrogen, alkyl, which is a straight or branched chain containing 1 to 12, preferably 1 to 6 carbons, more preferably 1–3 carbons, alkenyl, which is a straight or branched chain, containing 1 to 12, preferably containing 1–6 carbons and one or two double bonds, or aryl, which contains 5 to 7 carbon atoms, and each is preferably 2-propenyl, ethyl, methyl or aryl, preferably phenyl or phenylmethyl, or
(ii) $R^5$ and $R^6$ are selected from carbon chains, heteroatoms, and carbon chains containing one or more heteroatoms, so that with the nitrogen atom to which each is attached, they form a 3- to 7-, preferably 5- or 6-, membered heterocyclic ring containing one to three heteroatoms, that is preferably a piperidinyl, alkylpiperidinyl, morpholinyl or pyrrolidinyl radical that is unsubstituted or substituted with halo, halo lower alkyl or lower alkyl, and is more preferably a 4-morpholinyl, or di($C_1$–$C_6$ alkyl)-morpholinyl, preferably 2,6-di($C_1$–$C_6$ alkyl)-4-morpholinyl, radical; and $R^7$ is selected from among:

H;

OH;

—$R^{14}OR^{13}$ in which $R^{13}$ is hydrogen or lower alkyl, preferably containing 1 to 4 carbons, alkanoyl containing 2 to 5, preferably 2 or 3, carbon atoms, and $R^{14}$ is lower alkenyl or lower alkyl, preferably containing 1 to 4 carbon atoms, more preferably methyl, ethyl, methylene or ethylene;

—$CH_2NR^{15}R^{16}$ in which $R^{15}$ is hydrogen, lower alkyl or lower alkanoyl and $R^{16}$ is hydrogen or lower alkyl;

$OR^{15}$ in which $R^{15}$ is hydrogen, lower alkyl or lower alkanoyl;

$R^{20}OR^{13}$, in which $R^{20}$ is lower alkyl;

$C(O)OR^{17}$ in which $R^{17}$ is hydrogen, alkyl containing from 1 to 7 carbons or alkenyl having 3–7 carbon atoms, aryl or heteroaryl, particularly pyridyl, phenyl, tolyl, ethylphenyl, butylphenyl, halophenyl, alkenyl containing 3 to 7 carbons and having formula $C_nH_{(2n-1)}$; or an alkali metal or alkaline earth metal salt, such as sodium, potassium, calcium and ammonium.

Also intended for use herein are N-oxides of any of the compounds of formula (I), pharmaceutically acceptable acids and salts of the compounds of formula (I) and prodrugs thereof.

It is understood that compounds of the above formula (or any of the compounds described herein) may have one or more asymmetric carbon atoms. Pure sterochemically isomeric forms of the above compounds may be obtained, and diastereoisomers isolated by physical separation methods, including, but not limited to crystallization and chromatographic methods. Cis and trans diasteriomeric racemates may be further resolved into their isomers. If separated, active isomers may be identified by their activity as defined herein. Such purification is not, however, necessary for preparation of the compositions or practice of the methods herein.

Of the above classes of compounds and compounds of formula (I), the compounds for use in the methods and compositions herein are those that, upon topical or local administration, exhibit activity as peripheral anti-hyperalgesics but, upon local or topical administration, are substantially devoid of CNS activity as defined below. Such compounds are typically anti-diarrheal compounds, as assessed in standard assays, that exhibit low or no activity in assays that assess CNS activity. As defined below, for purposes herein, such anti-diarrheal and CNS activity is assessed in standard assays relative to 2,2-diphenyl-4-[(4-carbethoxy-4-phenyl)piperidino]butyronitrile, generically known as diphenoxylate.

Selected compounds for use in the methods and compositions herein have:

(1) activity as a peripheral anti-hyperalgesic activity as assessed in any recognized in vivo or in vitro model or assay; and substantially no CNS-mediated effects, which are preferably assessed by selecting compounds that have (2) either (a) a B/A ratio greater than diphenoxylate and a B value at least about 2-fold greater than diphenoxylate, or (b) a B/A ratio more than about 2-fold greater than diphenoxylate, where:

B is the $ED_{50}$ of the compound in an art-recognized assay (the hot plate tail withdrawal test or the tail clip test, described below, or assay that yields equivalent results) that measures CNS activity of the compound, and A is the $ED_{50}$ of the compound in an art-recognized assay (the Castor Oil test or Antagonism of $PGE_2$-induced diarrhea in mice, described below, or an assay that yields equivalent results) that measures anti-diarrheal activity of the compound. The ratio of these activities of the compound of interest is compared to the ratio of the activities of diphenoxylate in the same assays. Among preferred compounds are those that have a B/A ratio that is more than about 3-fold greater than diphenoxylate.

Preferred among the compounds of formula (I) are those of formula (II) or N-oxides thereof:

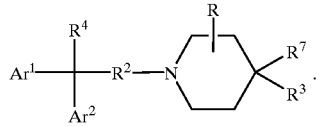

II preferably where $R^4$ is

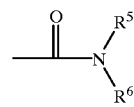

and more preferably where $R^7$ is OH, R is hydrogen or methyl, and $R^3$ is $Ar^3$, preferably phenyl, more preferably 4-halo-phenyl.

More preferred compounds are loperamide (4-(p-chlorophenyl)-4-hydroxy-N-N-dimethyl-α,α-diphenyl-1-piperidinebutyramide hydrochloride) and analogs (see formula III) thereof that exhibit B/A ratios greater than loperamide (see, e.g., U.S. Pat. Nos. 3,884,916 and 3,714,159). Such compounds include those in which:

(i) $Ar^1$ and $Ar^2$ are phenyl, R is hydrogen, $R^2$ is $(CH_2)_2$, $R^5$ and $R^6$, with the nitrogen to which each is linked form pyrrolidine and $R^3$ is 4-chlorophenyl or 3,4,-dichlorophenyl;

(ii) $Ar^1$ and $Ar^2$ are phenyl, R is hydrogen, $R^2$ is $(CH_2)_2$, $R^5$ and $R^6$, with the nitrogen to which each is linked form piperidinyl and $R^3$ is phenyl;

(iii) $Ar^1$ and $Ar^2$ are phenyl, $R^2$ is $(CH_2)_2$, R is hydrogen, $R^5$ and $R^6$ are each methyl and $R^3$ is 4-bromophenyl;

(iv) $Ar^1$ and $Ar^2$ are phenyl, $R^2$ is $(CH_2)_2$, R is hydrogen, $R^5$ and $R^6$ are methyl and ethyl, respectively, and $R^3$ is 4-chlorophenyl;

(v) $Ar^1$ and $Ar^2$ are phenyl, $R^2$ is $CH_2CHCH_3$, R is hydrogen, $R^5$ and $R^6$ are each methyl and $R^3$ is 4-fluorophenyl; and (vi) $Ar^1$ and $Ar^2$ are phenyl, $R^2$ is $CH_2CH_2$, R is 4-methyl, $R^5$ and $R^6$ are each methyl and $R^3$ is 3-trifluoromethylphenyl or phenyl.

Because of its ready availability and demonstrated safety, loperamide HCl is presently most preferred.

Compositions formulated for topical and local administration for treatment of hyperalgesia are also provided. The compositions provided herein, are preferably formulated for single dosage administration, and contain an anti-hyperalgesic effective amount of one or more of the selected compounds in a vehicle formulated for topical or local administration. Generally the compounds are provided in the form of a suspension or emulsion at concentrations of from about 0.1%, preferably from greater than about 1%, particularly when formulated in aqueous medium for application to the nasal passages or lungs, up to 50% or more.

The compositions are formulated as creams, aqueous or non-aqueous suspensions, lotions, emulsions, suspensions or emulsions containing micronized particles, gels, foams, aerosols, solids and other suitable vehicles for application to the skin, eyes, lips and mucosa, as suppositories or creams for vaginal administration, and as combinations with bandages, patches, bioadhesives and dressings. The compounds may be formulated in combination with other agents, such as local anesthetics and other therapeutic agents. The other agents may be mixed in the compositions are provided and administered prior to, simultaneously with or subsequent to administration of the compositions provided for the methods herein. Such agents include, but are not limited to: antibiotics, including cephalosporins, β-lactams, tetracyclines, vancomycins, sulfas and aminoglycosides; antivirals, including acylovir; and antifungals including clotrimazole.

Methods of treating hyperalgesia by applying an amount of the compositions provided herein effective to ameliorate or eliminate the hyperalgesic state are provided. Thus, methods of treating pain and irritation associated with inflammation following local infection, blisters, boils, or acute skin injuries, such as abrasions, burns, superficial cuts, surgical incisions, toothaches, contusions, irritations, inflammatory skin conditions, including but not limited to poison ivy, and allergic rashes and dermatitis and any condition that yields a hyperalgesic pain state and other such conditions are provided.

Articles of manufacture containing: packaging material, a compound (or compounds) provided herein, which is effective for ameliorating peripheral hyperalgesia within the packaging material, and a label that indicates that the compound, acid, salt or other derivative thereof is used for treating hyperalgesic conditions, are provided.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are, unless noted otherwise, incorporated by reference in their entirety.

As used herein, hyperalgesia or a hyperalgesic state refers to a condition in which a warm-blooded animal is extremely sensitive to mechanical, chemical or thermal stimulation that, absent the condition, would be painless. In recent years, it has been shown that after the induction of a local inflammatory state, peripheral afferent terminals, which are otherwise only activated by high intensity stimuli, may develop spontaneous activity (Handwerker et al. (1991) *Pain and inflammation, Proceeding of the VIth World Congress on Pain,* Bond et al. eds, Elsevier Science Publishers BV, pp. 59–70). Such spontaneous activity itself yields a central (spinal) facilitation that is believed to result in a state of hyperalgesia (Yaksh, 1993). Typical models for such a hyperalgesic state include the inflamed rat paw compression model (Stein, et al. (1989) *J. Pharmacol. Exp. Ther.* 248:1269–1275) and the compression of the inflamed knee joint (Sato, et al. (1986) *J. Physiol* 375:611–624). In these models, it has been shown that the local injection of mu opioids can induce a normalization of the hyperalgesic state. Agents that serve to normalize the sensitized thresholds are behaving as anti-hyperalgesics, rather than as analgesics.

Hyperalgesia is known to accompany certain physical injuries to the body, for example the injury inevitably caused by surgery. Hyperalgesia is also known to accompany certain inflammatory conditions in man such as arthritic and rheumatic disease. Prostaglandins, such as prostaglandin $E_1$ or prostaglandin $E_2$ (hereinafter $PGE_1$ and $PGE_2$ respectively), act to sensitize pain receptors to mechanical or chemical stimulation. Low doses of these prostaglandins can induce the hyperalgesic state. A long-lasting hyperalgesia occurs when PGE, is infused in man, and the co-administration of PGE, with a further chemical stimulant, such as bradykinin, causes marked pain that would not be present in the absence of PGE.

Hyperalgesia, thus refers to mild to moderate pain (and possibly severe pain) such as the pain associated with, but not limited to, inflammatory conditions (such as rheumatoid arthritis and osteoarthritis), postoperative pain, post-partum pain, the pain associated with dental conditions (such as dental caries and gingivitis), the pain associated with burns, including but not limited to sunburns, abrasions, contusions and the like, the pain associated with sports injuries and sprains, inflammatory skin conditions, including but no limited to poison ivy, and allergic rashes and dermatitis, and other such pain that increases sensitivity to mild stimuli. Locally or topically applied or administered anti-hyperalgesic agents do not necessarily abolish pain sensation, but need only restore (or reduce the threshold closer to) the pre-hyperalgesic pain threshold.

As used herein, an agent that acts, directly or indirectly via a receptor or receptors responsible for mediating or involved in peripheral hyperalgesia, by antagonizing the activity of hyperalgesia mediating agents, such as a prostaglandin, is an agent intended for use herein, if it also does not exhibit CNS effects as defined herein. As intended herein, the activity of anti-hyperalgesic agents is distinct from the activity of centrally-acting analgesic agents (agents that act by virtue of crossing the blood brain barrier). Anti-hyperalgesic agents act to block the hypersensitivity. The compositions and methods herein are intended for the amelioration of the symptoms (i.e., treatment) of hyperalgesia by decreasing or eliminating the hyperalgesia.

As used herein, an effective dose or amount of a compound for use herein refers to a concentration or amount that is effective upon topical administration to reduce or ameliorate the hyperalgesic condition and thereby reduce the pain threshold to levels closer to normal or to normal (i.e, the level in the absence of the hyperalgesic condition). Typically, compounds are provided in compositions that are formulated for single dosage administration.

As used herein, the compounds provided herein, including those of formula (I), also include pharmaceutically acceptable salts, acids and esters thereof, stereoisomers, and also metabolites or prodrugs thereof that possess activity as anti-hyperalgesics but do not cause substantial CNS effects (as defined herein) when topically or locally administered or applied. Metabolites include any compound that is produced upon administration of the compound and metabolism thereof. Thus, loperamide refers to 4-(ρ-chlorophenyl)-4-hydroxy-N-N-dimethyl-α,α-diphenyl-1-piperidinebutyramide hydrochloride and active metabolites thereof.

As used herein, loperamide and analogs thereof are compounds that have formula (I), below, and active N-oxides and pharmaceutically acceptable salts thereof.

As used herein, local application or administration refers to administration of an anti-hyperalgesic agent to the site, such as an inflamed joint, that exhibits the hyperalgesic condition and that does not exert central analgesic effects or CNS effects associated with systemic administration of opioids that cross the blood brain barrier. Such local application includes intrajoint, such as intra-articular application, via injection, application via catheter or delivery as part of a biocompatible device.

As used herein, topical application refers to application to the surface of the body, such as to the skin, eyes, mucosa and lips, which can be in or on any part of the body, including but not limited to the epidermis, any other dermis, or any other body tissue. Topical administration or application means the direct contact of the anti-hyperalgesic with tissue, such as skin or membrane, particularly the cornea, or oral, vaginal or buccal mucosa. Topical administration also includes application to hardened tissue such as teeth and appendages of the skin such as nails and hair. A composition formulated for topical administration is generally liquid or semi-liquid carriers such a gel, lotion, emulsion, cream, plaster, or ointment, a spray or aerosol, or a "finite" carrier, i.e., a non-spreading substance that retains its form, such as a patch, bioadhesive, dressing and bandage. It may be aqueous or non-aqueous; it may be formulated as a solution, emulsion or a suspension.

As used herein, a lack of CNS effects or systemic effects, including and particularly CNS effects and CNS-mediated effects, means that the agent exhibits at least about 2-fold less activity in an assay or animal model (particularly those as defined and described herein) for such effects than 2,2-diphenyl-4-[(4-carbethoxy-4-phenyl)piperidino]butyronitrile, generically known as diphenoxylate, which has the formula:

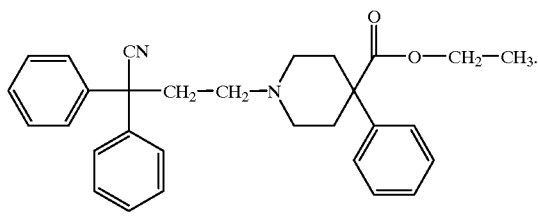

As used herein, the biological activity or bioactivity of a particular compound includes any activity induced, potentiated or influenced by the compound in vivo or in vitro. It also includes the abilities, such as the ability of certain molecules to bind to particular receptors and to induce a functional response. It may be assessed by in vivo assays or by in vitro assays, such as those exemplified herein.

As used herein, pharmaceutically acceptable salts, esters or other derivatives of the compounds include any salts, esters or derivatives that may be readily prepared by those of skill in this art using known methods for such derivatization and that produce compounds that may be administered to animals or humans without substantial toxic effects and that either are pharmaceutically active or are prodrugs. For example, hydroxy groups can be esterified or etherified.

As used herein, N-oxides refer to oxides of one or more nitrogens, preferably the nitrogen on the piperidine ring (see, eg., formula (I)).

As used herein, substantially pure means sufficiently homogeneous to appear free of readily detectable impurities as determined by standard methods of analysis, such as thin layer chromatography (TLC), mass spectrometry (MS), size exclusion chromatography, gel electrophoresis, particularly agarose and polyacrylamide gel electrophoresis (PAGE) and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, adequately pure or "pure" per se means sufficiently pure for the intended use of the adequately pure compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach,* Oxford University Press, New York, pages 388–392).

As used herein, the $IC_{50}$ refers to an amount, concentration or dosage of a particular test compound that achieves a 50% inhibition of a maximal response in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, "halogen" or "halide" or "halo" refers to F, Cl, Br or I, and also pseudohalides. In preferred embodiments halo refers to F, Cl, Br and I.

As used herein, pseudohalides are compounds that behave substantially similar to halides. Such compounds can be used in the same manner and treated in the same manner as halides ($X^-$, in which X is a halogen, such as Cl or Br). Pseudohalides include, but are not limited to cyanide, cyanate, thiocyanate, selenocyanate, azide and trifluoromethyl. As used herein, carbon chains and carbon chains with heteroatoms, may be straight or branched or, if they contain 3 or more members may be cyclic.

As used herein, alkyl, alkenyl and alkynyl carbon chains, if not specified contain from 1 to 20 carbons, preferably 1 to 12 carbons, and are straight or branched.

As used herein, lower alkyl, lower alkenyl, and lower alkynyl refer to carbon chains having one to about 6 carbons. In preferred embodiments of the compounds provided herein that include alkyl, alkenyl, or alkynyl portions include lower alkyl, lower alkenyl, and lower alkynyl portions. Preferred among lower carbon chains are those having 1–3 carbons.

As used herein, aryl refers to cyclic groups containing from 3 to 15 or 16 carbon atoms, preferably from 5 to 10, more preferably 5 to 7 carbons. Aryl groups include, but are not limited to groups, such as phenyl, substituted phenyl, naphthyl, substituted naphthyl, in which the substituent is lower alkyl, halo, halo lower alkyl, or lower alkoxy. Preferred aryl groups are lower aryl groups that contain less than 7 carbons in the ring structure.

As used herein, cycloalkyl refers to saturated cyclic carbon chains; cycloalkenyl and cycloalkynyl refer to cyclic carbon chains that include at least one unsaturated triple bond. The cyclic portions of the carbon chains may include one ring or two or more fused rings.

As used herein, a carbocyclic group is a ring containing at least three carbons; a heterocyclic group is a ring containing at least one carbon and one or more heteroatoms, preferably selected from among O, S, and N, more preferably N and O. A heteroaryl group is an unsaturated ring structure containing 1 or more, preferably 1 to 3 heteroatoms in the ring. The rings may be single rings or two or more fused rings. Heteroaryl is used interchangeably with heterocycle.

As used herein, heterocycle refers to ring structures that include at least one carbon atom and one or more atoms, such as N, S and O.

As used herein, the nomenclature alkyl, alkoxy, carbonyl, etc. are used as is generally understood by those of skill in this art. For example, as used herein alkyl refers to non-aromatic carbon chains that contain one or more carbons; the chains may be straight or branched or include cyclic portions or be cyclic. As used herein, alicyclic refers to aryl groups that are cyclic.

As used herein, "haloalkyl" refers to an alkyl radical, preferably lower alkyl, in which one or more of the hydrogen atoms are replaced by halogen including, but not limited to, chloromethyl, trifluoromethyl, 1-chloro-2-fluoroethyl and other such groups. Halo lower alkyl refers to lower alkyl substituted with one or more halo substituents, and is preferably trichloromethyl or trifluoromethyl.

As used herein, "haloalkoxy" refers to RO— in which R is a haloalkyl group.

As used herein, "aminocarbonyl" refers to —C(O)NH$_2$.

As used herein, "alkylaminocarbonyl" refers to —C(O)NHR in which R is hydrogen, alkyl, preferably lower alkyl or aryl, preferably lower aryl.

As used herein, "dialkylaminocarbonyl" refers to —C(O)NR'R in which R' and R are independently selected from alkyl or aryl, preferably lower alkyl or lower aryl; "carboxamide" refers to groups of formula NR'COR.

As used herein, "alkoxycarbonyl" as used herein refers to —C(O)OR in which R is alkyl, preferably lower alkyl or aryl, preferably lower aryl.

As used herein, "alkoxy" and "thioalkoxy" refer to RO— and RS—, in which R is alkyl, preferably lower alkyl or aryl, preferably lower aryl.

As used herein, when particular group, such as phenyl or pyridyl, is specified, this means that the group is unsubstituted or is substituted. Preferred substituents where not specified are halo, halo lower alkyl, and lower alkyl.

As used herein, the abbreviations for any protective groups, amino acids, including non-naturally occurring and amino acid analogs, and other compounds, are, unless indicated otherwise, in accord with their common usage, recognized abbreviations, or the IUPAC-IUB Commission on Biochemical Nomenclature (see, (1972) Biochem. 11:942–944). Each naturally or non-naturally occurring L-amino acid is identified by the standard three letter code or the standard three letter code with the prefix "L-"; the prefix "D-" indicates that the stereoisomeric form of the amino acid is D.

A. Compounds

In animal models, it is demonstrated herein that the local injection of compounds that directly or indirectly agonize at least one of the $\mu$ and/or $\kappa$ and/or $\delta$, preferably $\mu$ and/or $\kappa$, peripheral receptors induces a normalization of the hyperalgesic state. This peripheral action of opiates in reducing the hyperalgesic state is of value, but traditional opiates, such as morphine, meperidine and fentanyl cross the blood-brain barrier allowing for the appearance of systemically and CNS mediated undesirable side effects. To solve these problems, the compositions provided herein contain compounds that exhibit activity as peripheral anti-hyperalgesics, but do not exhibit substantial CNS effects as determined in suitable animal models as described herein. Intended for use in the methods and compositions herein are any compounds that, by virtue of indirect or direct $\mu$ or $\kappa$ or $\delta$, preferably $\mu$ or $\kappa$, agonist activity, act as peripheral anti-hyperalgesics but that, upon local or topical administration, are substantially devoid (as defined herein) of CNS-mediated analgesic and other activities. Such compounds are typically anti-diarrheal compounds, as assessed in standard assays, that exhibit low or no activity in assays that assess CNS activity. In particular, such a compound is one that:

(1) has activity as a peripheral anti-hyperalgesic as assessed in any recognized in vivo or in vitro model or assay; and, substantially no CNS-mediated effects, which are preferably assessed by selecting compounds that have (2) either:

(a) a B/A ratio greater than diphenoxylate and a B value at least about 2-fold greater than diphenoxylate, or (b) has a B/A ratio greater, at least about 2-fold, (among the preferred compounds ratios greater than about 3-fold may be observed) than diphenoxylate, where:

B is the $ED_{50}$ of the compound in an assay (the well known tail clip assay or hot plate assay, described below) that measures CNS activity of the compound, the A is the $ED_{50}$ of the compound in an assay that measures anti-diarrheal activity of the compound. The assay in which anti-diarrheal activity is measured is the Castor oil test or the assay that measures antagonism of $PGE_2$-induced diarrhea in mice, described below (see, also, Dajani et al. (1977) J. Pharmacol. Exp. Ther. 203:512–526, Dajani et al. (1975) European Jour. Pharmacol. 34:105–113; U.S. Pat. Nos. 4,870,084; 4,066,654, 4,057,549; 3,950,537; 3,998,832, 3,996,214). The relative activities of the compound of interest are compared to the activities of diphenoxylate in the same assays. It is understood that the assays are art-recognized assays such that diphenoxylate activity serves as an accurate standard.

Of particular interest herein are compositions that are formulated, at concentrations effective for reducing, alleviating or eliminating, hyperalgesic pain, for topical or local administration and contain one or more compounds of formula (I) or N-oxides, preferably an N-oxide of a piperidine-nitrogen, thereof or other pharmaceutically acceptable derivatives thereof:

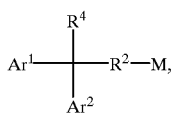

I where M is

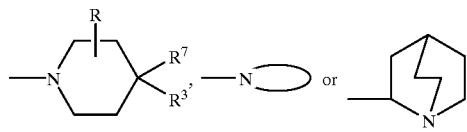

in which:

is an azabicycloalkyl containing from 6 to 9 carbon atoms with at least 5 atoms in each ring, is preferably:

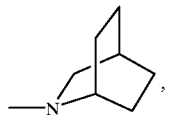

and is unsubstituted or substituted with $OR^{18}$ in which $R^{18}$ is hydrogen or lower alkanoyl containing 2 to 7, preferably 2 or 3, carbon atoms, and $OR^{18}$ is preferably attached at the 5 position in 5-membered rings or the 5 or 6 position in 6-membered rings and is attached in the endo or exo configuration;

$Ar^1$ and $Ar^2$ are either (i) or (ii) as follows:

(i) each is independently selected from aryl and heteroaryl groups containing from 5 to 7 members in the ring, preferably phenyl and pyridyl, and each is unsubstituted or substituted with one or more, preferably up to three substituents, preferably selected from halo, hydroxy, alkyl, haloalkyl, halo lower alkyl, particularly trifluoromethyl, alkyloxy, aminosulfonyl, alkylcarbonyl, nitro, amino, aminocarbonyl, phenylcarbonyl that are unsubstituted or substituted with one or more, preferably up to three substituents selected from among halo and alkyl, and thienyl that is unsubstituted or substituted with halo or alkyl, where the alkyl groups are straight or branched chains and preferably are lower alkyl containing from 1 to 6 carbon atoms, more preferably 1 to 3 carbon atoms; or (ii) $Ar^1$ and $Ar^2$ are each independently phenyl or pyridyl groups, preferably phenyl, and with the carbon to which they are commonly linked form a fused ring so that the compounds of formula (I) have the structure:

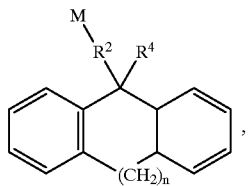

where n is 0 to 3, preferably 1 to 3, more preferably 2 or 3;

$R^2$ is either alkylene in which the alkyl group is a straight or branched chain, preferably is lower alkyl containing from 1 to 6, more preferably 1 to 3 carbons and most preferably is —$(CH_2)_2$— or —$CH_2CH(CH_3)$—, or is alkylene having 1 to 6 carbon atoms, preferably 1 to 3 carbons atoms and one or two, preferably one, double bond;

$R^3$ is $Ar^3$, —Y—$Ar^3$, where Y is alkylene or alkyl having 1 to 3 carbon atoms, or is

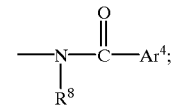

$R^8$ is hydrogen or alkyl that is a straight or branched chain, preferably containing from 1 to 6, more preferably 1 to 3, carbon atoms;

$Ar^3$ is aryl or heteroaryl containing from 5 to 7 members in the ring, preferably phenyl or pyridyl, which is unsubstituted or substituted with one or more preferably, up to three substituents, preferably selected from halo, halo lower alkyl and lower alkyl;

$Ar^4$ is either:

(i) is a heterocycle containing one or more fused rings, preferably 1 to 3 fused rings, each of which is unsubstituted or substituted with one or more substituents selected from halo, halo lower alkyl or lower alkyl, preferably halo, and is preferably selected from hetrocyles that include, but are not limited to, indolyl, benzofuranyl, benzothienyl, isoquinolinyl, quinolinyl, benzimidazolyl, naphthyl, thienyl, furanyl, pyridinyl, thiazolyl, imidazolyl, is more preferably thienyl, furanyl, pyridinyl, thiazolyl, imidazolyl each of which is unsubstituted or substituted with halo, or (ii) $Ar^4$ is a radical of formula:

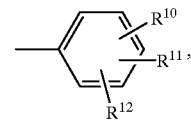

in which $R^{10}$, $R^{11}$ and $R^{12}$ are each independently selected from hydrogen, alkyl, alkyloxy, alkoxyalkyl, halo, haloalkyl, hydroxy, cyano, nitro, amino, alkylamino, di(alkyl)amino, aminocarbonyl, arylcarbonylamino, alkylcarbonylamino, alkylcarbonyl, alkylcarbonyloxy, aminosulfonyl, alkylsulfinyl, alkylsulfonyl, alkylthio, mercapto, $C_{3-6}$alkenyloxy, arlyalkyloxy, aryloxy, alkyl, in which each group is unsubstituted or substituted with one or more, preferably 1 to 4 halo atoms or halo lower alkyl, preferably methyl, groups, and the alkyl groups are straight or branched chains that are preferably lower alkyl ($C_{1-6}$) and more preferably $C_{1-3}$;

R is hydrogen, alkyl, preferably lower alkyl, or halo or halo lower alkyl, and is preferably at the 3-position (relative to the N), more preferably a 3-halo or 3-lower alkyl, or R is OR⁹, which is preferably at the 3-position so that the piperidinyl ring has the formula:

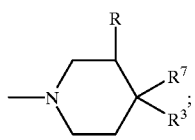

R⁹ is selected from alkyl, arylalkyl, alkylcarbonyl, aminoalkyl, alkylaminoalkyl, dialkylaminoalkyl, in which the alkyl groups are straight or branched chains and preferably contain 1 to 12, more preferably 1 to 6, most preferably 1 to 3 carbons in the chain;

R⁴ is selected from among:
(i) a 5- to 7-membered aryl group, preferably phenyl, which is unsubstituted or substituted with lower alkyl, halo or halo lower alkyl, or
(ii) a heterocyclic ring containing one to three heteroatoms, that is unsubstituted or substituted with halo, halo lower alkyl or lower alkyl, and is preferably a pyrrolidinyl, oxadiazolyl or triazolyl radical, more preferably oxadiazolyl, most preferably 1,3,4-oxadiazolyl, particularly a 5-substituted 1,3,4-oxadiazolyl in which the substituent is halo, halo lower alkyl or lower alkyl, or
(iii) alkyl containing from 1 to 8, preferably 1 to 6, more preferably 1 to 3 carbon atoms, alkenyl containing 3 to 6 carbon atoms, cycloalkyl containing from 3 to 6 carbons, cycloalkyl alkyl in which the first alkyl contains 3 to 6 carbons and the second contains 1 to 3 carbons, or cycloalkenyl containing 4 to 7 carbons, or (iv)

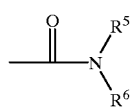

where
R⁵ and R⁶ are either:
(i) independently selected from hydrogen, alkyl, which is a straight or branched chain containing 1 to 12, preferably 1 to 6 carbons, more preferably 1–3 carbons, alkenyl, which is a straight or branched chain, containing 1 to 12, preferably containing 1–6 carbons and one or two double bonds, or aryl, which contains 5 to 7 carbon atoms, and each is preferably 2-propenyl, ethyl, methyl or aryl, preferably phenyl or phenylmethyl, or
(ii) R⁵ and R⁶ are selected from carbon chains, heteroatoms, and carbon chains containing one or more heteroatoms, so that with the nitrogen atom to which each is attached they form a 3- to 7-, preferably 5- or 6-, membered heterocyclic ring containing one to three heteroatoms, that is preferably a piperidinyl, alkylpiperidinyl, morpholinyl or pyrrolidinyl radical that is unsubstituted or substituted with halo, halo lower alkyl or lower alkyl, and is more preferably a 4-morpholinyl, or di(C₁–C₆ alkyl)-morpholinyl, preferably 2,6-di(C₁–C₆ alkyl)-4-morpholinyl, radical; and R⁷ is selected from among:
H;
OH;
—R¹⁴OR¹³ in which R¹³ is hydrogen or lower alkyl, preferably containing 1 to 4 carbons, alkanoyl containing 2 to 5, preferably 2 or 3, carbon atoms, and R¹⁴ is lower alkyl or lower alkenyl, preferably containing 1 to 4 carbon atoms, more preferably methyl or ethyl, most preferably —CH₂—CH₂—;
—CH₂NR¹⁵R¹⁶ in which R¹⁵ is hydrogen, lower alkyl or lower alkanoyl and R¹⁶ is hydrogen or lower alkyl;
OR¹⁵ in which R¹⁵ is hydrogen, lower alkyl or lower alkanoyl;
R²⁰OR¹³, in which R²⁰ is lower alkyl;
C(O)OR¹⁷ in which R¹⁷ is hydrogen, alkyl containing from 1 to 7 carbons or alkenyl having 3–7 carbon atoms, aryl or heteroaryl, particularly pyridyl, phenyl, tolyl, ethylphenyl, butylphenyl, halophenyl, alkenyl containing 3 to 7 carbons and having formula $C_nH_{(2n-1)}$; or
an alkali metal or alkaline earth metal salt, such as sodium, potassium, calcium and ammonium.

Preferred among the compounds of formula (I) are those of formula (II) or N-oxides thereof and other pharmaceutically acceptable derivatives:

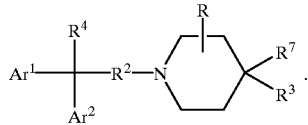

II where:
Ar¹ and Ar² are each independently selected from aryl and heteroaryl groups containing from 5 to 7 members in the ring, preferably phenyl and pyridyl, that are unsubstituted or substituted with one or more, preferably up to three substituents, selected from halo, haloalkyl, particularly trifluoromethyl, hydroxy, alkyl, alkyloxy, aminosulfonyl, alkylcarbonyl, nitro, haloalkyl, amino, aminocarbonyl, phenylcarbonyl that are unsubstituted or substituted with up to three substituents selected from among halo and alkyl, and thienyl that is unsubstituted or substituted with halo, haloalkyl or alkyl, in which the alkyl groups are straight or branched chains that contain 1 to 12 carbons, preferably are lower alkyl, more preferably containing 1 to 3 carbons;

R³ is Ar³ or is

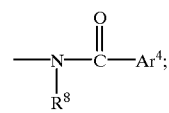

Ar³ is aryl containing from 5 to 7 members in the ring, preferably phenyl, which is unsubstituted or substituted with one or more, preferably one up to three substituents, preferably selected from halo, halo lower alkyl and lower alkyl;

Ar⁴ is thienyl, furanyl, pyridinyl, thiazolyl, imidazolyl, each of which is unsubstituted or substituted with halo or halo lower alkyl, or Ar⁴ is a radical of formula:

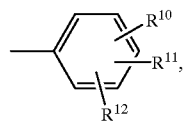

in which $R^{10}$, $R^{11}$ and $R^{12}$ are each independently selected from hydrogen, alkyl, alkyoxy, halo, haloalkyl, hydroxy, cyano, nitro, amino, alkylamino, di(alkyl)amino, aminocarbonyl, arylcarbonylamino, alkylcarbonylamino, alkylcarbonyl, alkylcarbonyloxy, aminosulfonyl, alkylsulfinyl, alkylsulfonyl, alkylthio, mercapto, $C_{3-6}$alkenyloxy, arlyalkyloxy, aryloxy, alkyl, in which each group is unsubstituted or substituted with up to 4 halo atoms or halo lower alkyl, and the alkyl groups are straight or branched chains that are preferably lower alkyl, and more preferably $C_{1-3}$;

$R^2$ is alkylene in which the alkyl group is a straight or branched chain containing 1 to 12 carbon atoms, preferably lower alkyl, more preferably containing 1 to 3 carbon atoms and most preferably is —$(CH_2)_2$— or —$CH_2CH(CH_3)$—;

R is hydrogen, alkyl, preferably lower alkyl, halo, and is preferably at the 3-position (relative to the N) is more preferably a 3-lower alkyl, or is $OR^9$, which is preferably in the 3-position;

$R^9$ is selected from alkyl, arylalkyl, alkylcarbonyl, aminoalkyl, alkylaminoalkyl, dialkylaminoalkyl, in which the alkyl groups are straight or branched chains, preferably containing 1 to 6 carbon atoms, more preferably 1 to 3 carbon atoms in the chain;

$R^4$ is phenyl or pyridyl or is:

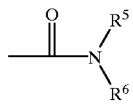

where
$R^5$ and $R^6$ are either:
  (i) independently selected from hydrogen, aryl, alkyl, that is a straight or branched chain containing 1 to 6, preferably 1 to 3 carbons, alkenyl that is a straight or branched chain, preferably containing 2 to 6 carbons and 1 or 2 double bonds, more preferably containing 1 to 4 carbons and 1 double bond, and is more preferably 2-propenyl, aryl, preferably phenyl or phenylmethyl, or
  (ii) $R^5$ and $R^6$, with the nitrogen atom to which each is attached form a form a 3- to 7-, preferably 5- or 6-, membered heterocyclic ring containing one to three heteroatoms, that is preferably selected from pyrrolidinyl, piperidinyl, alkylpiperidinyl, morpholinyl, oxadiazolyl or triazolyl radical, each of which is unsubstituted or substituted with one or more substituents selected from halo, halo lower alkyl or lower alkyl, and is more preferably 1,3,4-oxadiazolyl, particularly a 5-substituted 1,3,4-oxadiazolyl in which the substituent is halo, halo lower alkyl or lower alkyl, a 4-morpholinyl or di($C_1$–$C_6$ alkyl)-4-morpholinyl radical;

$R^7$ is H, OH, C(O)OH, C(O)H or —$R^{14}OR^{13}$ in which $R^{13}$ is hydrogen or lower alkyl, preferably containing 1–4 carbons, or is an alkanoyl containing 2 to 5, preferably 2 or 3 carbon atoms, and $R^{14}$ is lower alkyl or alkenyl, preferably methyl or ethyl; and $R^8$ is hydrogen or alkyl that is a straight or branched chain containing from 1 to 6, preferably 1 to 3, carbon atoms.

In more preferred embodiments all alkyl groups contain from 1 to 3 carbon atoms; R is hydrogen or methyl, $R^4$ is

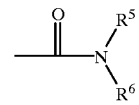

in which $R^5$ and $R^6$ are each independently methyl, ethyl or propyl, which is branched or straight, or phenyl, or $R^5$ and $R^6$ with the nitrogen to which each is attached form pyrollidinyl, piperidinyl, morpholinyl, which is preferably unsubstituted, and more preferably where $R^7$ is OH and $R^3$ is $Ar^3$, preferably phenyl.

Among preferred compounds of formula (I) are those of formula (III) or N-oxides thereof and other pharmaceutically acceptable derivatives:

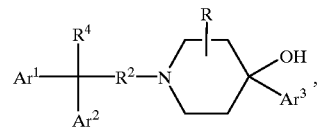

in which:
$Ar^1$ and $Ar^2$ are each independently selected aryl containing from 5 to 7 members in the ring, preferably phenyl groups, that is unsubstituted or substituted with up to three substituents, preferably selected from halo, haloalkyl or alkyl in which the alkyl groups are straight or branched chains and preferably are lower alkyl containing from 1–6 carbons, more preferably 1–3 carbons;

$R^2$ is alkylene or alkenyl containing one double bond, where the carbon chain in the alkyl or alkenyl group is a straight or branched chain, containing preferably from 1 to 6, more preferably 1 to 3, carbons, and is preferably lower alkyl;

R is hydrogen, alkyl, preferably lower alkyl, or halo, and is preferably a 3-lower alkyl or hydrogen;

$R^4$ is:

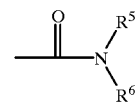

where
$R^5$ and $R^6$ are either:
  (i) independently selected from hydrogen or alkyl or alkenyl, which may be a straight or branched chain, and each is preferably lower alkyl, more preferably methyl or ethyl, or
  (ii) $R^5$ and $R^6$, with the nitrogen atom to which each is attached, form a 3 to 7, preferably 5 or 6, member carbon ring or heterocyclic ring containing one or two heteroatoms, that is preferably a pyrrolidinyl, piperidinyl, alkylpiperidinyl, morpholinyl, preferably 4-morpholinyl, or di($C_1$–$C_6$ alkyl)-morpholinyl, preferably 2,6-di($C_1$–$C_6$ alkyl)-4-morpholinyl, radical; and $Ar^3$ is aryl containing from 5 to 7 members in the ring, preferably phenyl, which is unsubstituted or substituted with up to three substituents, preferably selected from halo and lower alkyl.

Of the compounds of formula (II), the compounds of formula (IV) are particularly preferred:

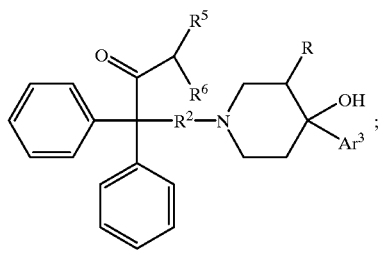

IV in which R³ is phenyl, which is unsubstituted or preferably substituted with halo or halo lower alkyl, preferably 4-halo. More preferred are those compounds in which R² is —(CH₂)₂—.

In other embodiments, the compounds of formula (I) are those having formula (V) (see, e.g., U.S. Pat. No. 4,990,521) or N-oxides thereof and other pharmaceutically acceptable derivatives:

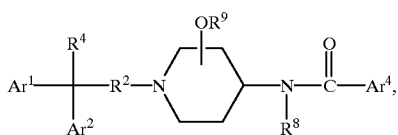

V in which:

Ar¹ and Ar² are each independently selected aryl containing from 5 to 7 members in the ring, preferably phenyl groups, that is unsubstituted or substituted with up to three substituents, preferably selected from halo, hydroxy, alkyl, alkyloxy, aminosulfonyl, alkylcarbonyl, nitro, haloalkyl, particularly trifluoromethyl, amino, aminocarbonyl, phenylcarbonyl that are unsubstituted or substituted with up to three substituents selected from among halo, haloalkyl, and alkyl, and thienyl that is unsubstituted or substituted with halo, haloalkyl or alkyl, in which the alkyl groups are straight or branched chains and preferably are lower alkyl containing from 1–6 carbons, more preferably 1–3 carbons;

Ar⁴ is thienyl, furanyl, pyridinyl, thiazolyl, imidazolyl, each of which are unsubstituted or substituted with halo or halo lower alkyl, or Ar⁴ is a radical of formula:

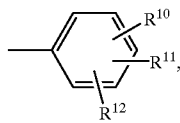

in which R¹⁰, R¹¹ and R¹² are each independently selected from hydrogen, alkyl, alkoxy halide, hydroxy, cyano, nitro, amino, alkylamino, di(alkyl)amino, aminocarbonyl, arylcarbonylamino, alkylcarbonylamino, alkylcarbonyl, alkylcarbonyloxy, aminosulfonyl, alkylsulfinyl, alkylsulfonyl, alkylthio, mercapto, $C_{3-6}$alkenyloxy, arlyalkyloxy, aryloxy, alkyl, in which each group is unsubstituted or substituted with up to 4 halo atoms, and the alkyl groups are straight or branched chains that are preferably lower alkyl ($C_{1-6}$) and more preferably $C_{1-3}$;

R² is alkylene, wherein the alkyl group is a straight or branched chain, preferably is lower alkyl containing from 1 to 6, preferably 1–3 carbons and more preferably is —(CH₂)₂— or —CH₂CH(CH₃)—;

R⁹ is selected from alkyl, arylalkyl, alkylcarbonyl, aminoalkyl, alkylaminoalkyl, dialkylaminoalkyl, in which the alkyl groups are straight or branched chains and preferably contain 1–6 carbons, more preferably 1–3 carbons in the chain:

R⁴ is:

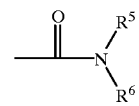

where

R⁵ and R⁶ are either:

(i) independently selected from hydrogen, aryl, alkyl, which is a straight or branched chain containing preferably 1–6 carbons, more preferably 1–3 carbons, alkenyl, which is a straight or branched chain, preferably containing 1–6 carbons and 1 double bond, and is more preferably 2-propenyl, aryl, preferably phenyl or phenylmethyl, or (ii) R⁵ and R⁶, with the nitrogen atom to which each is attached, form a 3- to 7-, preferably 5- or 6-, membered heterocyclic ring containing one or two heteroatoms selected from O, S and N, preferably O or N, that is preferably a pyrrolidinyl, piperidinyl, alkylpiperidinyl, morpholinyl, preferably 4-morpholinyl or di($C_1$–$C_6$ alkyl)-morpholinyl, more preferably 2,6-di($C_1$–$C_6$ alkyl)-4-morpholinyl, radical;

R⁸ is hydrogen or alkyl that is a straight or branched chain, preferably containing from 1 to 6, more preferably 1 to 3, carbons.

Preferred among these compounds are those in which the substituents in the 3- and 4-positions on the piperidine ring have the trans configuration. More preferred are those in which Ar⁴ is phenyl; R¹⁰ is aryl, loweralkyloxy, $C_{3-6}$alkenyloxy, $C_{3-6}$alkynyloxy, or $C_{1-5}$ alkyl substituted with 1 to 4 halo atoms, and R¹¹ and R¹² are each independently selected from hydrogen, lower alkyl, lower alkoxy, halo, halo alkyl, hydroxy, cyano, nitro, amino, mono and di(alkyl)amino, aminocarbonyl, arylcarbonylamino, alkylcarbonylamino, alkylcarbonyl, alkylcarbonyloxy, aminosulfonyl, alkylsulfinyl, alkylsulfonyl, alkylthio and mercapto in which each group is unsubstituted or substituted with up to 4 halo atoms, and the alkyl groups are straight or branched chains that are preferably lower alkyl ($C_{1-6}$) and more preferably $C_{1-3}$; R⁵ and R⁶ are independently selected from hydrogen, $C_{1-4}$alkyl, phenylmethyl and 2-propenyl.

In more preferred compounds R¹⁰ is trifluoromethyl substituted on the meta positions, and R¹¹ and R¹² are each independently hydrogen, methyl, methoxy, halo, hydroxy, nitro, amino trifluoromethyl, phenylmethyoxy, phenyloxy, and propenyloxy. Preferred compounds include trans-3-hydroxy-N,N,γ-trimethyl-α,α-diphenyl-4-[[3-(trifluoromethyl)-benzoyl]amino]-1-piperidinebutanamide.

In other embodiments, the compounds of formula (I) are those having formula (VI) (see, e.g., U.S. Pat. No. 4,194,045) or N-oxides thereof and other pharmaceutically acceptable derivatives:

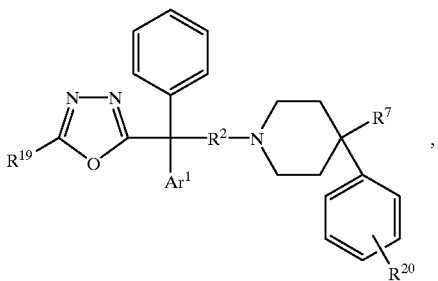

VI where:

Ar$^1$ is phenyl, alkyl substituted phenyl, halo-substituted phenyl, or pyridyl, in which the alkyl groups are straight or branched chains and preferably are lower alkyl containing from 1 to 6 carbons, more preferably 1 to 3 carbons;

R$^2$ is alkylene, in which the alkyl group is a straight or branched chain, preferably is lower alkyl containing from 1 to 6, preferably 1 to 3 carbons, or is alkylene containing 2–4 carbons, preferably ethylene, and more preferably is —(CH$_2$)$_2$— or —CH$_2$CH(CH$_3$)—, and most preferably —(CH$_2$)$_2$;

R$^7$ is —R$^{14}$OR$^{13}$ in which R$^{13}$ is hydrogen or lower alkyl, preferably containing 1–4 carbons, or is an alkanoyl containing 2 to 5, preferably 2 or 3, carbon atoms, and R$^{14}$ is lower alkyl or lower alkenyl, preferably methyl or ethyl; and R$^{19}$ is hydrogen or lower alkyl, preferably containing 1–4 carbons; and R$^{20}$ is hydrogen, halo or lower alkyl, preferably containing 1–4 carbons.

Preferred among the compounds of formula (VI) are those in which R$^{13}$ is hydrogen or lower alkyl or alkanoyl having 2–5 carbon atoms; R$^{14}$ is methyl or ethyl; R$^{19}$ is hydrogen or methyl; R$^{20}$ is hydrogen, halogen or methyl; R$^2$ is —(CH$_2$)$_2$—; and Ar$^1$ is phenyl. Such preferred compounds include 5-[1,1-diphenyl-3-(4-phenyl-4-methanolpiperidino) propyl]-2-methyl-1,3,4-oxadiazole.

In other embodiments, the compounds of formula (I) are those having formula (VII) (see, e.g., U.S. Pat. No. 3,996,214) or N-oxides thereof and other pharmaceutically acceptable derivatives:

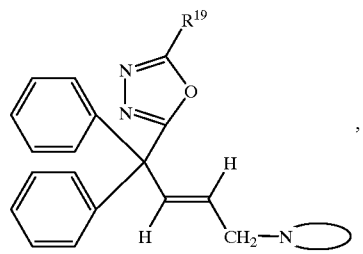

VII where:

R$^{19}$ is lower alkyl, preferably containing from 1–3 carbon atoms; the configuration of the double bond is trans; and

is a secondary amine selected from azabicycloalkyls containing from 6 to 9 carbon atoms with at least 5 atoms in each ring, is preferably, pyrrolidino, piperidino, hexamethyleneimino, is preferably 7-azabicyclo[2.2.1]hept-7-yl, 2-azabicyclo[2.2.2]oct-2-yl, 2-azabicyclo[3.2.1]oct-2-yl, 3-azabicyclo[3.2.1]oct-3-yl, 6-azabicyclo[3.2.1]oct-6-yl, 3-azabicyclo[3.2.2]non-3-yl, 8-azabicyclo[4.3.0]-non-8-yl, 2-azabicyclo[3.2.2]non-2-yl, 2-azabicyclo[3.3.1]non-2-yl, 3-azabicyclo[3.3.1]non-3-yl, 2-azabicyclo[4.3.0]non-3-yl, 7-azabicyclo[4.3.0]non-7-yl, 8-azabicyclo[4.3.1]dec-8-yl, 2-azabicyclo(4.4.0]-dec-2-yl, and 7-azabicyclo[4.2.2]dec-7-yl, and is more preferably:

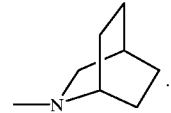

Preferred compounds include 5-[1,1-diphenyl-4-(2-azabicyclo[2.2.2]oct-2-yl)but-2-trans-en-1-yl]-2-methyl-1,3,4-oxadiazole.

In other embodiments, the compounds of formula (I) are those having formula (VIII) (see, e.g., U.S. Pat. No. 4,012,393) or N-oxides thereof and other pharmaceutically acceptable derivatives:

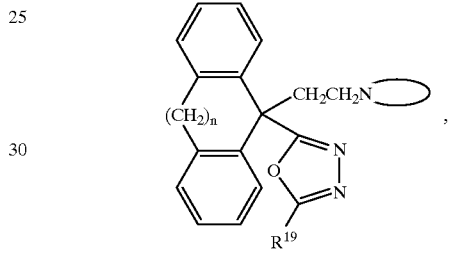

VIII where:

R$^{19}$ is lower alkyl, preferably containing from 1–3 carbon atoms, preferably methyl, n is an integer between 1 and 3, preferably 2 or 3; and

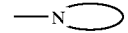

is a secondary amine selected from azabicycloalkyls containing from 6 to 9 carbon atoms with at least 5 atoms in each ring, is preferably, pyrrolidino, piperidino, hexamethyleneimino, is preferably 7-azabicyclo[2.2.1]hept-7-yl, 2-azabicyclo[2.2.2]oct-2-yl, 2-azabicyclo[3.2.1]oct-2-yl, 3-azabicyclo[3.2.1]oct-3-yl, 6-azabicyclo[3.2.1]oct-6-yl, 3-azabicyclo[3.2.2]non-3-yl, 8-azabicyclo[4.3.0]-non-8-yl, 2-azabicyclo[3.2.2]non-2-yl, 2-azabicyclo[3.3.1]non-2-yl, 3-azabicyclo[3.3.1]non-3-yl, 2-azabicyclo[4.3.0]non-3-yl, 7-azabicyclo[4.3.0]non-7-yl, 8-azabicyclo[4.3.1]dec-8-yl, 2-azabicyclo[4.4.0]-dec-2-yl, and 7-azabicyclo[4.2.2]dec-7-yl, and is more preferably:

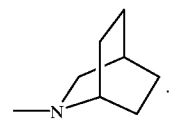

Preferred compounds include 2-{5-[2-(2-azabicyclo[2.2.2]oct-2-yl)ethyl]-10.11-dihydro-5H-dibenzo[a,d]cyclohepten-5-yl}-5-methyl-1,3,4 -oxadiazole; and 2-{[2-[2-(2-azabicyclo[2.2.2]oct-2-yl)ethyl}-5,6,7,12-tetrahydrodibenzo[a,d]cycloocten-12-yl}-5-methyl-1,3,4-oxadiazole.

In other embodiments, the compounds of formula (I) are those having formula (IX) (see, e.g., U.S. Pat. No. 4,013,668) or N-oxides thereof and other pharmaceutically acceptable derivatives:

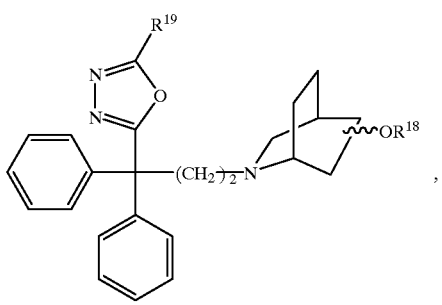

IX in which $R^{19}$ is lower alkyl; $R^{18}$ is hydrogen or lower alkanoyl containing 2 to 7, preferably 2 or 3, carbon atoms, more preferably hydrogen or acetyl, and is attached at the 5 or 6 position in either the endo or exo configuration.

Preferred among the compounds of formula (IX) are: 5-[1,1-diphenyl-3-(exo-5-hydroxy-2-azabicyclo[2,2.-2]oct-2-yl)-propyl]2-methyl-1,3,4-oxadiazole; 5-[1,1-diphenyl-3-(exo-5-acetoxy-2-azabicyclo[2.2.-2]oct-2-yl)-propyl]-2-methyl-1,3,4-oxadiazole; 5-[1,1-diphenyl-3-(endo-5-acetoxy-2-azabicyclo[2.2.-2]oct-2-yl)-propyl]-2-methyl-1,3,4-oxadiazole; 5-[1,1-diphenyl-3-(endo-5-hydroxy-2-azabicyclo[2.2.-2]oct-2-yl)-propyl]-2-methyl-1,3,4-oxadiazole; 5-[1,1-diphenyl-3-(endo-6-acetoxy-2-azabicyclo[2.2.-2]oct-2-yl)-propyl]-2-methyl-1,3,4-oxadiazole; 5-[1,1-diphenyl-3-(endo-6-hydroxy-2-azabicyclo[2.2.-2]oct-2-yl)-propyl]-2-methyl-1,3,4-oxadiazole; 5-[1,1-diphenyl-3-(exo-6-acetoxy-2-azabicyclo[2.2.-2]oct-2-yl)-propyl]-2-methyl-1,3,4-oxadiazole; and 5-[1,1-diphenyl-3-(exo-6-hydroxy-2-azabicyclo[2.2.-2]oct-2-yl)-propyl]-2-methyl-1,3,4-oxadiazole.

In other embodiments, the compounds of formula (I) are those having formula (X) (see, e.g., U.S. Pat. No. 4,069,223) or N-oxides thereof and other pharmaceutically acceptable derivatives:

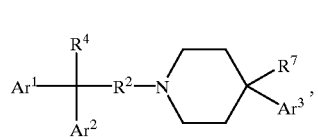

X in which:

$Ar^1$, $Ar^2$ and $Ar^3$ are each independently selected from among phenyl, which is unsubstituted or substituted at one or two positions with halo or lower alkyl, preferably containing 1 to 4 carbons;

$R^2$ is alkylene, in which the alkyl group is a straight or branched chain, preferably is lower alkyl containing from 1 to 6, preferably 1–3 carbons, or is alkylene containing 2–4 carbons, preferably 2 or 3 carbons, and is more preferably is —$(CH_2)_2$— or —$CH_2CH(CH_3)$—, and most preferably —$(CH_2)_2$;

$R^4$ is phenyl, which is unsubstituted or is substituted at one or more positions with halo, halo lower alkyl or lower alkyl, preferably containing 1 to 4 carbons, or is pyridyl; $R^7$ is $CH_2NR^{15}R^{16}$ in which $R^{15}$ is hydrogen, lower alkyl or lower alkanoyl and $R^{16}$ is hydrogen or lower alkyl. In more preferred embodiments of the compounds of formula (X), $Ar^1$, $Ar^2$ and $Ar^3$ are each phenyl and $R^4$ is phenyl or pyridyl.

Included among the preferred compounds of these compounds of formula (X) are: 4-amino-methyl-4-phenyl-1-(3,3,3-triphenylpropyl)piperidine and N-{[4-phenyl-1-(3,3,3-triphenylpropyl)piperidine-4-yl[methyl]acetamide.

In other embodiments, the compounds are those of formula (X) (see, e.g., U.S. Pat. No. 4,066,654) in which $Ar^1$, $Ar^2$ and $Ar^3$ are each independently selected from among phenyl, which is unsubstituted or substituted at one or two positions with halo or lower alkyl or halo lower alkyl, preferably containing 1 to 4 carbons; $R^2$ is alkylene, wherein the alkyl group is a straight or branched chain, preferably is lower alkyl containing from 1 to 6, preferably 1–3 carbons, or is alkylene, preferably a branched chain, containing 2–4 carbons, preferably ethylene, and is more preferably is —$(CH_2)_2$— or —$CH_2CH(CH_3)$—, and most preferably —$(CH_2)_2$; $R^4$ is phenyl, which is unsubstituted or is substituted at one or more positions with halo or lower alkyl, preferably containing 1 to 4 carbons, or is pyridyl; $R^7$ is $C(O)OR^{17}$ in which $R^{17}$ is hydrogen, alkyl containing from 1 to 7 carbons or alkenyl having 3 to 7 carbon atoms, aryl or heteroaryl, particularly pyridyl, phenyl, tolyl, ethylphenyl, butylphenyl, halophenyl, alkenyl containing 3 to 7 carbons and having formula $C_nH_{(2n-1)}$, or is an alkali metal or alkaline earth metal salt, such as sodium, potassium, calcium, and ammonium; and $R^2$ is a straight or branched alkylene containing from 2 to 4 carbons or is lower alkyl, preferably containing from 1 to 3 carbons, more preferably 2 carbons. In preferred embodiments, $Ar^1$ and $Ar^2$ are phenyl and $R^4$ is phenyl or 2-, 3- or 4-pyridyl.

Among the preferred of these compounds of formula (X) are 1-(3,3,3-triphenylpropyl)-4-phenyl-4-piperidinecarboxylic acid hydrochloride; ethyl 1-(3,3,3-triphenylpropyl)-4-phenyl-4-piperidinecarboxylate; potassium 1-(3,3,3-triphenylpropyl)-4-phenyl-4-piperidinecarboxylate; sodium 1-(3,3,3-triphenylpropyl)-4-phenyl-4-piperidinecarboxylate; 1-[3,3-diphenyl-3-(2-pyridyl)propyl]4-phenyl-4-piperidine carboxylic acid hydrochloride; sodium 1-[3,3-diphenyl-3-(2-pyridyl)propyl]-4-phenyl-4-piperidinecarboxylate; ethyl 1-[3,3-diphenyl-3-(2-pyridyl)propyl]-4-phenyl-4-piperidinecarboxylate; potassium 1-[3,3-diphenyl-3-(2-pyridyl)propyl]-4-phenyl-4-piperidinecarboxylate.

In other embodiments, the compounds are those of formula (X) (see, e.g., U.S. Pat. No. 4,072,686) in which $Ar^1$, $Ar^2$ and $Ar^3$ are each independently selected from among phenyl, which is unsubstituted or substituted at one or two positions with halo or lower alkyl or halo lower alkyl, preferably containing 1 to 4 carbons; $R^2$ is alkylene, wherein the alkyl group is a straight or branched chain, preferably is lower alkyl containing from 1 to 6, preferably 1–3 carbons, or alkylene containing 2–4 carbons, preferably ethylene, and is more preferably is —$(CH_2)_2$— or —$CH_2CH(CH_3)$—, and most preferably —$(CH_2)_2$; $R^4$ is phenyl, which is unsubstituted or is substituted at one or more positions with halo or lower alkyl, preferably containing 1 to 4 carbons, or is pyridyl; $R^7$ is —$R^{14}OR^{13}$ in which $R^{13}$ is hydrogen or lower alkyl, preferably containing 1–4 carbons, or is an alkanoyl containing 2 to 5, preferably 2 or 3, carbon atoms, and $R^{14}$ is lower alkyl or lower alkenyl containing 1 to 4 carbons, and is preferably methyl or ethyl, or is lower alkyl containing 1 to 4 carbons, having formula —$(C_nH_{2n})$—, containing preferably 2 or 3 carbons. In preferred embodiments, $Ar^1$ and $Ar^2$ are phenyl and $R^4$ is phenyl or 2-, 3- or 4-pyridyl.

Among the preferred of these compounds of formula (X) are: 1-(3,3,3-triphenylpropyl)-4-phenyl-4-piperidinemethanol; 1-[3,3-diphenyl-3-(2-pyridyl)propyl]-4-phenyl-4-piperidinemethanol; 1-(3,3,3-triphenylpropyl)-

4-phenyl-4-acetoxymethyl-piperidine; 1-(3,3,3-triphenylpropyl)-4-phenyl-4-methoxymethyl-piperidine; 1-(3,3,3-triphenylpropyl)-4-(4-chlorophenyl)-4-piperidinemethanol; 1-[3-ρ-chlorophenyl-3,3-diphenylpropyl]-4-(phenyl}-4-piperidinemethanol; 1-[3-(ρ-tolyl)-3,3-diphenylpropyl]-4-(phenyl)-4-piperidinemethanol; 1-[3-(ρ-bromophenyl)-3,3-diphenylpropyl]-4-(phenyl)-4-piperidinemethanol; 1-[3,3-diphenyl-3-(4-pyridyl)propyl]-4-phenyl-4-piperidinemethanol; 1-[3,3-diphenyl-3-(3-pyridyl)propyl]-4-phenyl-4-piperidinemethanol; 1-(3,3,3-triphenylpropyl)-4-phenyl-4-hexoxymethyl-piperidine; 1-(3,3,3-triphenylpropyl)-4-(ρ-tolyl)-4-piperidinemethanol; 1-(3,3,3-triphenylpropyl)-4-(ρ-trifluoromethyl)-4-piperidinemethanol; 1-(3,3,3-triphenylbutyl)-4-(phenyl)-4-piperidinemethanol; 1-(3,3,3-triphenylpropyl)-4-(phenyl)-4-piperidinemethanol; 1-(3,3,3-triphenylpropyl)-4-phenyl-4-methoxyethylpiperidine; 1-[3,3-diphenyl-3-(2-pyridyl)propyl]-4-phenyl-4-methoxyethylpiperidine; 1-(3,3,3-triphenylpropyl)-4-phenyl-4-piperidinemethanol; 1-[3,3-diphenyl-3-(2-pyridyl)propyl]-4-phenyl-4-piperidinemethanol; 1-(3,3,3-triphenylpropyl)-4-phenyl-4-acetoxymethylpiperidine; 1-(3,3,3-triphenylpropyl)-4-phenyl-4-methoxymethylpiperidine; 1-(3,3,3-triphenylpropyl)-4-(chlorophenyl)-4-piperidinemethanol and acid salts thereof.

In other embodiments, the compounds of formula (I) are those having formula (XI) (see, e.g., U.S. Pat. No. 4,116,963) or N-oxides thereof and other pharmaceutically acceptable derivatives thereof:

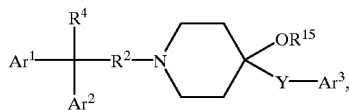

where:

$Ar^1$, $Ar^2$ and $Ar^3$ are each independently selected from among phenyl, which is unsubstituted or substituted at one or two positions with halo, halo lower alkyl or lower alkyl, preferably containing 1 to 4 carbons; $R^2$ is alkylene, wherein the alkyl group is a straight or branched chain, preferably is lower alkyl containing from 1 to 6, preferably 1–3 carbons, or is alkylene containing 2–4 carbons, preferably ethylene, and more preferably is —(CH$_2$)$_2$— or —CH$_2$CH(CH$_3$)—, and most preferably is —(CH$_2$)$_2$; $R^4$ is phenyl, which is unsubstituted or is substituted at one or more positions with halo, halo lower alkyl or lower alkyl, preferably containing 1 to 4 carbons, or is pyridyl; $R^{15}$ is hydrogen, alkyl or alkanoyl containing 1 to carbon atoms, preferably 1 to 8 carbons; and Y is alkyl or alkylene having 1 to 3 carbons, and is preferably —CH$_2$—.

Among the preferred compounds of formula (XI) are 1-(3,3,-triphenylpropyl)4-hydroxy-4-benzylpiperidine and 1-(3,3,3-triphenylpropyl)-4-hydroxy-4-benzylpiperidine; hydrochloride; 1-(3,3,3-triphenylpropyl)-4-hydroxy-4-p-chlorobenzylpiperidine; 1-(3,3,3-triphenylpropyl)-4-hydroxy-4-p-methylbenzylpiperidine; and 1-[3,3-3(2-pyridyl)propyl]-4-benzyl-4-p-hydroxypiperidine.

In other embodiments, the compounds are amidinoureas (see, U.S. Pat. Nos. 4,326,075, 4,203,920, 4,115,564, 4,060,635 and 4,025,652) or are 2-[(aminophenyl and amidophenyl)amino]-1-azacycloalkanes (see, U.S. Pat. No. 4,533,739) that have formula XII or pharmaceutically acceptable derivatives, including the non-toxic acid addition salts thereof:

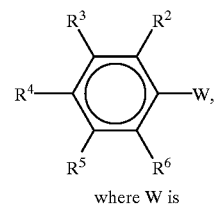

where W is

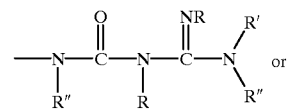

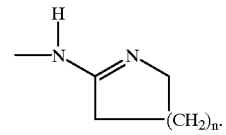

In the compounds of formula (XII) W is XII(a) or W is XII(b).

(i) When, W is XII(a), then $R^2$, $R^3$, $R^4$, $R^5$ and $R^6$, which are the same or different, are each independently selected from: hydrogen, halo, lower alkyl, halo lower alkyl, nitro, lower alkoxy, hydroxy, aryl lower alkoxy, acyloxy, cyano, halo lower alkoxy or lower alkyl sulfonyl; R is hydrogen or lower alkyl; R' and R" are hydrogen alkyl cycloalkyl or aralkyl, or R' and R" together form a 5–7 atom ring that includes 0 to 2 hetero atoms selected from N, O or S; $R_n$ is hydrogen or lower alkyl, provided that at least one of R, R' and R" is other than hydrogen.

When W is XII(a) preferred compounds are those in which: $R^2$, $R^3$, $R^4$, $R^5$ and $R^6$ are hydrogen, halo, lower alkyl, halo lower alkyl, nitro, hydroxy or lower alkoxy; and R and R" are hydrogen or lower alkyl and R' and R" are hydrogen or lower alkyl and R' and R" are hydrogen or alkyl; provided R, R' and R" are not all hydrogen at the same time.

More preferred compounds, when W is XII(a), are those where: $R^2$ is hydrogen or lower alkyl; $R^3$ and $R^5$ are hydrogen, hydroxy or lower alkoxy; $R^4$ is hydrogen, lower alkyl, hydroxy, lower alkoxy or halo, $R^6$ is hydrogen, lower alkyl, nitro, alkoxy or halo; R and R" are hydrogen or lower alkyl; and R' and R" are hydrogen or alkyl; provided R, R' and R" are not all hydrogen at the same time.

The most preferred compounds, when W is XII(a), are those where: $R^2$ is hydrogen, methyl or ethyl; $R^3$ is hydrogen, hydroxy or methoxy; $R^4$ is hydrogen, methyl, ethyl, hydroxy, methoxy, chloro or bromo; $R^5$ is hydrogen, hydroxy or methoxy; $R^6$ is hydrogen, methyl, ethyl, nitro, methoxy, ethoxy, chloro, bromo or fluoro; R and R" are hydrogen, methyl or ethyl; and R' and R" are hydrogen, methyl, ethyl, propyl, i-propyl, butyl, i-butyl, sec-butyl, t-butyl, pentyl, hexyl or; heptyl; provided R, R' and R" are not all hydrogen at the same time.

Other preferred compounds, when W is XII(a) include those in which the compounds have a $R^2$, $R^6$-di-lower alkyl substitution; $R^2$, $R^6$-lower alkyl substitution; $R^2$, $R^6$-lower alkyl, alkoxy substitution; $R^2$, $R^6$-lower alkyl, halo substitution; $R^2$, $R^6$-alkyl, nitro substitution; $R^2$, $R^4$, $R^6$-tri-lower alkyl substitution, or $R^2$, $R^4$, $R^6$-lower alkyl, di-halo substitution. Other preferred compounds have an $R^3$, $R^4$-hydroxy or alkoxy substitution; a $R^3$, $R^4$, $R^5$-hydroxy or alkoxy substitution; $R^2$, $R^5$-di-halo substitution or $R^2$, $R^6$-di-halo substitution.

Other preferred compounds, when W is XII(a) include those in which R, R' and R" are hydrogen or lower alkyl, provided that all are not hydrogen at the same time; or R and R' are hydrogen or lower alkyl and R" is an alkyl group from 3 to 7 carbon atoms.

Preferred compounds include, but are not limited to: m-chlorophenylamidinourea; p-chlorophenylamidinourea; 3,4-dichlorophenylamidinourea; m-bromophenylamidinourea; p-bromophenylamidinourea; 3,4-dibromo-phenylamidinourea; 3-chloro-4-bromophenylamidinourea; 3-bromo-4-chlorophenylamidinourea; 3-chloro-4-fluorophenylamidinourea; 3-bromo-4-fluorophenylamidinourea; 3-fluoro-4-chlorophenylamidinourea; 2,6-dimethylphenylamidinourea; 2,6-diethylphenylamidinourea; 2-methyl-6-ethylphenylamidinourea; 2-methyl-6-methoxyphenylamidinourea; 2-methyl-6-ethoxyphenylamidinourea; 2-ethyl-6-methoxyphenylamidinourea; 2-ethyl-6-ethoxyphenylamidinourea; 3,4-dimethoxyphenylamidinourea; 3,4-dihydroxyphenylamidinourea; 3,4,5-trimethoxyphenylamidinourea; and 3,4,5-trihydroxyphenylamidinourea.

(ii) In the compounds of formula (XII) or the pharmacologically acceptable salts thereof, when W is XII(b), when n is 1 to 3, preferably 1;

$R^2$, $R^6$ and $R^3$, which are independently selected and are the same or different, are selected from among: (a) hydrogen; (b) alkyl or 1 to 6 carbon atoms, inclusive; or (c) halogen; with the proviso that $R^2$ and $R^6$ are not hydrogen at the same time; and one of $R^4$ and $R^5$ is hydrogen, alkyl of 1 to 6 carbon atoms, inclusive, or halogen and the other is of the formula: —$NR^8R^7$ in which $R^8$ and $R^7$, which are the same or different, are selected from among: (a) hydrogen; (b) alkyl of 1 to 6 carbon atoms, inclusive; (c) alkoxycarbonyl of 2 to 7 carbon atoms, inclusive; (d) aryloxycarbonyl of 6 to 12 carbon atoms inclusive; (e) alkylcarbonyl of 2 to 7 carbon atoms inclusive; (f) arylcarbonyl of 6 to 12 carbon atoms, inclusive; (g) hydroxyalkoxycarbonyl of 3 to 7 carbon atoms, inclusive; (h) $R^8$ and $R^7$ are taken together to form (1) —$(CH_2)_p$—; wherein p is 4 or 5; (2) —$(CH_2)_m$CO—, where m is 3 or 4; (i) haloalkylcarbonyl of 2 to 7 carbon atoms, inclusive; wherein n is an integer of from 1 to 3, inclusive.

Preferred among the compounds of formula (XII) in which W is XII(b) are: 2-[(2-methyl-3-aminophenyl)amino]-1-pyrroline, dihydrochloride; 2-[(2-methyl-3-acetamidophenyl)amino]-1-pyrroline, hydrochloride; and 2-[(2-methyl-3-(ethoxycarbonylamino)phenyl-)aminol-1-pyrroline, hydrochloride.

Also among the compounds of formula (I) of interest herein are the 2-substituted-1-azabicyclo[2,2,2]octanes (see, U.S. Pat. No. 4,125,531) of formula XIII:

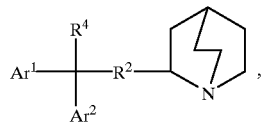

XIII where:

$R^2$ is lower alkyl, preferably containing 1 to 3 carbons;
$Ar^1$ and $Ar^2$ are each independently selected from aryl or heteroaryl containing from 5 to 7 members in the ring, preferably phenyl or pyridyl groups, that is unsubstituted or substituted with up to three substituents, preferably selected from halo, hydroxy, alkyl, alkyloxy, aminosulfonyl, alkylcarbonyl, nitro, haloalkyl, particularly trifluoromethyl, amino, aminocarbonyl, phenylcarbonyl that are unsubstituted or substituted with up to three substituents selected from among halo, haloalkyl, and alkyl, and thienyl that is unsubstituted or substituted with halo, haloalkyl or alkyl, in which the alkyl groups are straight or branched chains and preferably are lower alkyl containing from 1–6 carbons, more preferably 1–3; and $R^4$ is selected from alkyl containing from 1 to 8 carbons, preferably 1 to 6, more preferably 1 to 3, or is alkenyl containing 3 to 6 carbon atoms, or is cycloalkyl containing from 3 to 6 carbons, or is cycloalkyl alkyl in which the first alkyl contains 3 to 6 carbons and the second contains 1 to 3 carbons, or is a cycloalkenyl containing 4 to 7 carbons.

Preferred among compounds of formula XIII are 2-(2,2-diphenylpentyl)-1-azabicylo[2.2.2]octane, 2-(2,2-diphenylhexyl)-1-azabicylo[2.2.2]octane, 2-(2,2-diphenylpropyl)-1-azabicylo[2.2.2]octane, 2-(2,2-diphenyloctyl)-1-azabicylo[2.2.2]octane and 2-(2,2-diphenylheptyl)-1-azabicylo[2.2.2]octane.

Other compounds of interest herein include certain phenylacetamide derivatives (see, U.S. Pat. No. 5,242,944), including, but not limited to N-{(3,4-dimethylphenyl)propyl}-4-(2-aminoethoxy)-3-methoxyphenylacetamide, N-{(3,4-dimethylphenyl)propyl}-4-(2-aminoethoxy)-3-hydroxy-phenylacetamide, N-{(3,4-dimethylphenyl)propyl}-4-(2-aminoethoxy)-3-aminophenylacetamide, N-{(3-methylphenyl)propyl}-4-(2-aminoethoxy)-3-methoxy-phenylacetamide, N-{(3-methylphenyl)propyl}-4-(2-aminoethoxy)-3-hydroxy-phenylacetamide and N-{(3-dimethylphenyl)propyl}-4-(2-aminoethoxy)-3-aminophenylacetamide and other such compounds.

Also of interest are 3-hydroxy-7-oxomorphinans and 3-hydroxy-7-oxoisomorphinans (see, U.S. Pat. No. 4,277,605) including, but not limited to: 3-hydroxy-7-oxomorphinan and 3-hydroxy-7-oxoisomorphinans including d,l-3-hydroxy-7-oxo-N-methylmorphinan, 1-3-hydroxy-7-oxo-N-methylmorphinan, d,l-3-hydroxy-7-oxomorphinan, 1-3-hydroxy-7-oxomorphinan, d,l-3-hydroxy-7-oxo-N-methylisomorphinan, 1-3-hydroxy-7-oxo-N-methylisomorphinan, d,l-3-hydroxy-7-oxoisomorphinan 1-3-hydroxy-7-oxoisomorphinan and other such compounds.

Among other opioid compounds for use herein are enkephalin analogs, such as metkephamid (Tyr-D-Ala-Gly-Phe-N(ME)Met-NH$_2$; see, e.g., U.S. Pat. No. 4,430,327; Burkhart et al. (1982) *Peptides* 3:869–871 ;Frederickson et al. (1991) *Science* 211:603–605), (D-Thr$^2$,$\Delta^3$-Pro$^5$)-enkephalinamide, and other such analogs that have been designed not to pass through the blood-brain barrier or to exhibit minimal CNS effects relative to anti-diarrheal activity, such as synthetic opioid peptides, including H-Tyr-D-Nva-Phe-Orn-NH$_2$, H-Tyr-D-Nle-Phe-Orn-NH$_2$, H-Tyr-D-Arg-Phe-A$_2$bu-NH$_2$, H-Tyr-D-Arg-Phe-Lys-NH$_2$, and H-Lys-Tyr-D-Arg-Phe-Lys-NH$_2$ (see, U.S. Pat. No. 5,312,899; see, also Gesellchen et al. (1981) *Pept.: Synth., Struct., Funct., Proc. Am. Pept. Symp., 7th,;* Rich et al. (Eds), Pierce Chem. Co., Rockford, Ill., pp. 621–62) that do not cross the blood brain barrier.

Of all of the above compounds, those of formulae (I) are presently preferred. Those of formulae (II)-(IV) are more preferred and of those the following compounds or N-oxides or pharmaceutically active acid addition salts thereof are particularly preferred: 2-[4-(4-hydroxy-4-phenylpiperidino)-2,2-diphenylbutyryl]piperidine; 4-{4-[4- hydroxy-4-(3-trifluoromethylphenyl)piperidino]-2,2-diphenylbutyryl}morpholine; 1-{4-[4-hydroxy-4-(3-trifluoromethylphenyl)piperidino]-2,2-diphenylbutyl}piperidine; 4-(ρ-chlorophenyl)-4-hydroxy-N-N-,γ-trimethyl-α,α-diphenylpiperidine-1-butyramide; 4-(ρ-chlorophenyl)-4-hydroxy-N-N-dimethyl-α,α-diphenylpiperidine-1-butyramide (loperamide]; 4-(3,4-dichlorophenyl)-N,N-diethyl-4-hydroxy-α,α-diphenylpiperidine-1-butyramide; 4-(3,4-dichlorophenyl)-4-hydroxy-N,N-dimethyl-α,α-diphenylpiperidine-1-butyramide; 4-(4-chloro-3-trifluoromethylphenyl)-4-hydroxy-N,N-dimethyl-α,α-diphenylpiperidine-1-butyramide; 4-(ρ-fluorophenyl)-4-hydroxy-N-N,γ-trimethyl-α,α-diphenylpiperidine-1-butyramide; 4-(ρ-bromophenyl)-4-hydroxy-N-N-dimethyl-α,α-diphenylpiperidine-1-butyramide; 1-{4-[4-(3,4-dichlorophenyl)-4-hydroxypiperidino]-2,2-diphenylbutyryl}pyrrolidine; and 4-(ρ-chlorophenyl)-N-ethyl-4-hydroxy-N-methyl-α,α-diphenylpiperidine-1-butyramide.

Of these compounds, loperamide, (4-(ρ-chlorophenyl)-4-hydroxy-N-N-dimethyl-α,α-diphenyl-1-piperidinebutyramide monochloride) is presently most preferred:

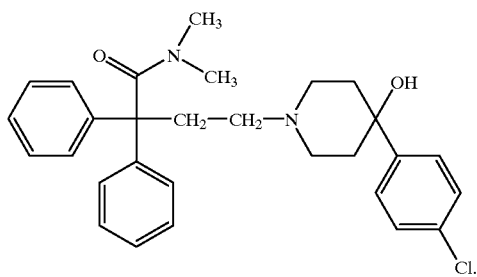

Also preferred are the N-oxides of loperamide HCl (see, e.g., U.S. Pat. No. 4,824,853) having the formula:

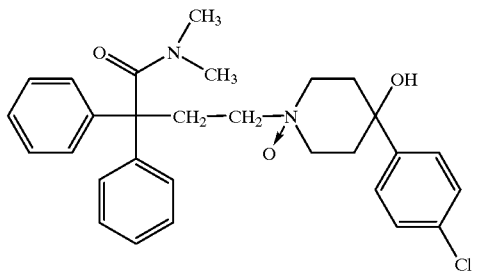

or other derivatives thereof.

Loperamide and its derivatives and analogs and the compounds described above (including those of formulae I–XIII, the other disclosed compounds and any compound that has the requisite hyperalgesic activity and lack of CNS activity as defined herein) will serve as topical or local peripheral anti-hyperalgesics that, by virtue of their inability or substantial inability to cross the blood-brain barrier, are safe and without abuse potential. This finding with respect to loperamide (see, e.g., Jaffe et al. (1980) *Clin. Pharmacol. Ther.* 80:812–819) has been verified by its use over-the-counter for over 10 years as an anti-diarrheal medication.

Other particularly preferred compounds include loperamide analogs, particularly compounds of formula (II) above, that have similar activity to loperamide (see, eg., U.S. Pat. Nos. 3,714,159 and 3,884,916, which set forth data regarding CNS activity (as measured in the tail withdrawal assay) and B/A ratios for the compounds) or better activity (higher B/A ratio than loperamide).

B. Identification of compounds for use as peripheral anti-hyperalgesics

In general the Randall-Selitto methods, described below, and the Exemplified methods are preferred for assessing peripheral anti-hyperalgesic activities of tested compounds.

1. Assessment of ratio (B/A), where B is the $ED_{50}$ value in a test of CNS effects, such as the Tail Withdrawal Test value, and A is the $ED_{50}$ in a test for anti-diarrheal activity, such as the Castor Oil Test The agents intended for use in the methods and compositions can be identified by their activity as anti-diarrheals, and their lack of CNS effects. In particular, the selected compound exhibits anti-hyperalgesic activity in any of the standard models, discussed or exemplified below, and either (a) the ratio of these activities (B/A), as measured in standard assays, is substantially greater (at least about 2-fold) than the ratio of such activities for diphenoxylate; or (b) the activity of the compound in an assay that measures CNS activity is substantially less (at least two-fold, preferably 3-fold or more) than diphenoxylate.

2. Assessment of anti-hyperalgesic activity

The agents for use herein may be identified using standard assays that assess the anti-hyperalgesic properties. The anti-hyperalgesic properties of a particular agent may be evaluated using the clinically relevant models of hyperalgesia, particularly animal models of tissue inflammation (see, e.g., Ferreira et al. (1979) *Prostaglandins* 73:191–200; Abbott et al. (1988) *Eur. J. Pharmacol.* 152:92–100; Levine et al. (1989) *Neuroscience* 32:571–575; Stein et al. (1989) *J. Pharmacol. Exp. Ther.* 248:1269–1275; Porreca et al. (1984) *J. Pharmacol. Exp. Ther.* 230:341–348; Stein et al. (1993) *Anesth. Analg.* 76:182–191). For example, the intraplantar injection of agents, such as prostaglandins into hindpaws of rats produces a localized inflammatory response which exhibits symptoms of hyperalgesia. The intraperitoneal administration of irritants, such as acetic acid, prostaglandins, carrageenan, killed mycobacteria, formalin or bradykinin, also produces an inflammatory reaction in which hyperalgesia is evidenced by writhing. In these models, either the latency of response by the animal to superimposed stimuli, such as pressure exerted on inflamed tissue, are measured, or behavioral alterations, such as the number of abdominal constrictions (writhing), following application of an irritant are measured.

Any in vitro or in vivo test known to those of skill in this art may be used to assess systemic opioid activity. The guinea pig ileum assay, the hot plate and the rat tail withdrawal assay are typical of such assays.

(a) Inflamed knee joint hyperalgesia model and blood pressure response to compression of the inflamed knee joint Inflammation in a joint is often associated with hyperalgesia (pain during normal flexion and extension and during the application of gentle innocuous pressure) and/or persistent pain (resting pain; Schaible et al. (1993) *Pain* 55:5–54). During the course of knee-joint inflammation, a cascade of events has been shown to occur, which includes: (i) synthesis and release of inflammatory mediators in the joint, (ii) release of neuropeptides from afferent fibers in the joint cavity, and (iii) increased primary afferent outflow from group II, III, IV sensory fibers (Schaible et al. (1993) *Pain* 55:5–54. An important result of this cascade is that there is an augmentation in the response of small, lightly myelinated and unmyelinated afferent to low intensity stimuli. In this manner, the peripheral nerve innervating inflamed tissue can evoke an exaggerated behavioral response to otherwise innocuous stimuli, i.e., a state of hyperalgesia. Thus, inflammation of the knee joint will result in increased spontaneous afferent activity, the appearance of an exaggerated discharge with joint flexion and extension (Schaible et al. (1985) *J. Neurophysiol.* 54:1109–1122) and signs of a pain-associated autonomic reaction (Sata et al. (1984) *Neurosci. Lett.* 52:55–60).

Injection of a mixture of kaolin and carrageenan into the knee joint induces an experimental arthritis. As exemplified below, this treatment was characterized by a reliable increase in joint volume and circumference. In the unanesthetized rat, these joint changes were accompanied by a tendency to avoid weight bearing, suggesting an ongoing pain state. According to electrophysiological studies, in the course of the development of this acute arthritis, C and Aδ units normally responding only to extreme joint distortion become activated by slight movement (Schaible et al. (1985) *J. Neurophysiol.* 54:1109–1122). Spinal neurons with knee joint receptive fields in the deep dorsal horn of the spinal cord show clear development of hyperexcitability with the acute inflammation in the joint (Neugebauer et al. (1993) *J. Neurosci.* 70:1365–1377). This sensitization of group III and IV fibers was observed within 2–3 hours after injection of kaolin and carrageenan into the knee joint, a time course that closely matches the time course of the development of hyperalgesia in the rat knee joint compression model. These observations indicate that spinal cord neurons and joint primary afferent fibers became sensitized and may underlie hyperalgesia observed in this arthritic state. Such afferent input may drive autonomic responses that are typically associated with the processing of input from afferents typically activated by stimuli generated by the local inflammatory state. In addition to the above-mentioned inflamed knee joint mechanism, the blood pressure (BP) changes might also be evoked reflexively by afferent neural activity from receptors located in the skeletal muscle (Williamson et al. (1994) *J. Physiol.* 475:351–357). This response is dependent on the changes in intramuscular pressure and the quantity of muscle mass compressed. This particular mechanical reflex, however, appears to operate independently of the pain response and appears to play a minor role in the exemplified experiments, as inflation of the cuff on the left normal knee joint had no effect upon BP. In any case, it is possible that overflow of the carrageenan from the joint capsule may serve to render surrounding tissue inflamed as well. Sensitization of C and Aδ units was observed in the rat gastrocnemius muscle by infiltration with carrageenan (Handwerker et al. (1991) *Pain and inflammation, Proceeding of the VIth World Congress on Pain,* Bond et al. eds, Elsevier Science Publishers BV, pp. 59–70). Based on these considerations, it appears that compression of the inflamed knee joint yields a noxious stimulus and this in turn activates a sympathetic response resulting in an increase in BP.

As described in the Examples below, local inflammation of the knee results in a state where otherwise innocuous stimuli results in a prominent autonomic response, including increased blood pressure (BP) and heart rate (see, e.g., Sata et al.(1984) *Neurosci. Lett.* 52:55–60).

Alternatively, neural outflow from the inflamed knee is recorded (see, e.g., Neugebauer et al. (1993) *J. Neurosci.* 70:1365–1377).

An in vitro test that measures spontaneous discharge in injured skin by topical application may also be used. (see, e.g., Andreev et al. (1994) *Neurosci.* 58:793–798).

(b) Guinea Pig Ileum Assay (in vitro)

Compounds are tested for opioid activity in the isolated guinea pig ileum (see, e.g., Kosterlitz et al. (1968) *Br. J. Pharmacol.* 33:266–276 with modifications set forth in James et al. (1987) *Pharmacol Exp. Ther.* 240:138–144; see, e.g., U.S. Pat. No. 5,387,688). The terminal ileum is removed from male Hartley guinea pigs after sacrifice by cervical dislocation. The isolated ileum is washed and placed in Krebs-Henseleit buffer ((millimolar): NaCl, 118.1; KCl, 4.15; $CaCl_2$, 2.5; $MgSO_4$ 1.2; $KH_2PO_4$, 1.23; $NaHCO_3$, 25.5 and glucose, 11.1) oxygenated with a 95% oxygen and 5% carbon dioxide mixture and maintained at 37° C. The washed ileum is cut into segments (about 2.0–2.5 cm) and mounted on platinum ring electrodes. The ileal segments are then placed in 10 ml temperature-controlled tissue baths containing oxygenated Krebs-Henseleit buffer.

The ileal segments are stimulated at 0.1 Hertz, 0.5 milliseconds duration at a supramaximal voltage to induce contractions. Opioid activity in the test compounds is manifested as inhibition of electrically evoked contractions. A non-cumulative concentration-effect curve for each test compound is performed to assess the ability of the compound to inhibit contraction in the guinea pig ileum.

After the concentration-effect curve is completed, naloxone is added to the tissue baths to determine if the compound-induced inhibition of contraction is reversed. Antagonism of the inhibition by naloxone confirms that the inhibitory effects of the compounds are mediated through opioid receptors. Assay results are expressed as $EC_{50}$ values (the concentration producing fifty percent of the maximal response)

(c) Randall-Selitto Test

Numerous variations and exemplifications of this assay are known to those of skill in this art (see, Randall et al. (1957) *Arch. Int. Pharmacodyn.* 111:409–419; see, also, e.g., U.S. Pat. Nos. 5,434,292, 5,369,131, 5,345,943, 5,242,944, 5,109,135, see Examples, below).

The pain threshold is measured in this method as the amount of pressure in mm Hg required to induce a flight reaction (struggle) when applied to the foot of an experimental animal exhibiting hyperalgesia, typically an inflamed paw, compared to a control, such as the same or equivalent animal in the absence of the inflammation, and/or in the absence of a test compound. Air pressure from an air line is admitted through a needle valve to a syringe into a pressure gauge which is connected by a T-tube. The syringe is mounted with a plunger downward, to which is connected a short bullet-shaped wooden peg. The pressure is applied through the wooden tip to the plantar surface of the rat's foot at a specified rate of mm Hg per second. The end point is said to have been reached when the rat starts struggling.

Typically, rats, such as albino rats (120–170 g) of the Charles River Sprague-Dawley strain, or other laboratory strain are used. Hyperalgesia (inflammation) is produced by the injection of 0.1 ml of a 20% suspension of Brewer's yeast into the plantar surface of the rat's hind foot. Thresholds are can be determined using a modified apparatus described in Winter and Flataker ((1965) *J. Pharm. Exp. Ther.* 148:373). The pain threshold is measured as the pressure in mm Hg required to induce the desired response (a sharp audible squeak and/or struggle) when pressure is applied to the foot. Air pressure from an air line (or other source, such as a vice) is admitted through a needle valve to a 20 ml glass syringe and to a pressure gauge. Pressure is applied to the foot of the rat at selected rate. The agent compound to be tested is administered typically 2 hours after the yeast injection and threshold response is determined. These results are compared with the results obtained from controls, typically a yeast-treated, saline control group. Analgesic activity was determined in terms of the percentage of inhibition of response:

$$\text{Inhibition (\%)} = \frac{\text{Threshold of the treated group} - \text{Threshold of the control group}}{\text{Threshold of the control group}} \times 100$$

(d) Tail-pinch or tail clip test in rats with hyperalgesia induced by Freund's adjuvant Desiccated *Mycobacterium butyricum* (such as that obtainable from Difco Laboratories, Detroit, Mich.) is ground in a mortar, suspended in liquid paraffin, sterilized in an autoclave, and injected (0.5 mg in 0.1 ml, s.c.) in the distal region of the tail of a rat, such as a Sprague-Dawley weighing 120 g to 170. Within a few hours of injection, animals that are so-treated exhibit hypersensitivity (hyperalgesia) to pressure placed on the tail and can be used, typically in 18 to 24 hours after injection as models to test the effectiveness of compounds in alleviating the hyperalgesia (see, e.g., U.S. Pat. No. 5,242,944). The hypersensitivity of the tail can be examined by applying gentle pressure (using one's fingers) to the injected area. This gentle squeeze or "tail pinch" elicited a "squeak" from the animal. Five such stimuli are typically given at 4-second intervals. If the animal emits no more than one squeak in five trials, it is recorded as having hyperalgesia and given a rating of 1. If there is more than one squeak, the rating is assigned a value of 0. This test is administered before and after administration of a test compound to ascertain whether the compound has any activity in relieving the hyperalgesia. This activity can be quantitated dividing the total rating by the number of animals tested (and if a percentage is desired, multiplying by 100) and comparing this number before and about two hours after administration of the test compound.

(e) Thermal Methods—Tail withdrawal assay

Typically thermal models are used to assess analgesia. They, however, can be used to assess hyperalgesia, if inflamed tissues are used. In addition, if the test is administered repeatedly resulting in inflammation, the measured response includes a hyperalgesic component.

The simplest form of these methods is the hot plate technique originally described by Woolfe and McDonalds (see, Woolfe et al. (1944) *J. Pharmacol. Exptl. Therap.* 80:300). Originally, this method used a zinc plate with a lamp placed underneath. In a later modification it uses an electric lamp as the source of heat and a copper plate for the conduction of heat (Eddy et al. (1953) *J. Pharmacol Exptl. Therap.* 107:385). The first sign of discomfort is usually expressed as an attempt to sit up and lick the forepaws by the experimental animal. This is taken to be an indication of a threshold under the predetermined conditions. Dancing and jumping about by an undrugged animal is taken as an indication of unbearable pain; whereas drugged animals more commonly withdraw the hind paws and keep them close to their abdomen.

In the wire technique, heat is applied from a wire coiled inside an asbestos plate. The animal's tail is placed in a channel made in the plate (Davis et al. (1946) *J. Pharmacol.* 1:255). Yet another thermal method uses light from a headlamp focused on the tip of the tail of an animal (D'Amour et al. (1941) *J. Pharmacol. Exptl. Therap.* 72:74). This method measures the time between the application of the heat and the flick of the tail and has therefore been called the "tail flick" method. Another thermal method uses a light bulb focused on the loin of an animal which is protected by a plexiglass shield having a port and a shutter positioned between a lens and the animal. When the shutter is opened the timer starts and when the animal reacts the shutter is closed and the timer stopped (Ercoli et al. (1945) *J. Pharmacol. Exptl. Therap.* 84:301). This method applies an incident light the strength of which can be varied by means of a rheostat.

The preferred tail withdrawal method for use herein is the rat tail withdrawal reflex model (modified from D'Amour et al. (1941) *Pharmacol. Exp. Ther.* 72:74–79; see, e.g., Gamse (1982) *Naunyn-Schmiedeberg's Arch. Pharmacol.* 320:205–216; U.S. Pat. Nos. 5,387,688; 3,714,159; and 5,112,596). Male Sprague-Dawley rats are anesthetized and implanted with femoral vein cannulae and allowed to recover overnight. After recovery, the test compounds are administered intravenously through the cannula and effects of tail withdrawal latency are measured.

Tail withdrawal latency is measured as the time to tail movement by the rat after exposure of the tail to a radiant heat source. The heat source is calibrated to produce a temperature of 62° C. after 15 seconds. Tail withdrawal latency in control animals (the absence of an opioid drug) is six to eight seconds. Test compounds demonstrating opioid activity prolong tail withdrawal latency beyond that seen in the absence of drugs. A maximal latency cut-off of fifteen seconds is imposed to prevent tissue damage. The assay is verified with known opioids as standards. Results of these studies are expressed as $ED_{50}$ concentration values, calculated as the dose producing a tail withdrawal latency equal to half the difference between the maximum latency (15 seconds) and the baseline latency (six to eight seconds). $ED_{50}$ values typically are expressed as milligrams of compound/kilogram of body weight. Duration of action is defined as the time (in minutes) necessary for the tail withdrawal response to return to baseline values after being elevated in response to drug administration. Duration of action is measured at the lowest dose producing a fifteen second (maximum) tail withdrawal latency.

(f) Other Mechanical Methods (see the Randall-Sclitto) method described above)

These methods, other than the Randall-Selitto method, are generally used for the primary screening of analgesics. Surgical blades adapted in various manners are used in the most primitive of these methods to produce a pain reaction. The blade is applied with a graded forceps and the amount of pressure necessary to elicit pain is expressed as the number of steps required in order to produce a squeak in the experimental animal. The pressure exercised by the blades of the forceps has also been measured by placing a dynamometer between the handles of the forceps. Artery clamps or clips have also been used instead of forceps. In humans, mechanical pressure has been applied over bone structures or by eliciting visceral pain such as in the enteric canal or in the esophagus by introducing and inflating balloons therein. The amount of pressure required to produce pain can be measured by means of a manometer but the subject itself is the one to report the degree of pain.

2. Tests for anti-diarrheal activity (a) Castor Oil Test in Rats (see, e.g., Niemegeers et al. (1972) *Arzneim orsch* 22:516–518; U.S. Pat. Nos. 4,867,979; 4,990,521; 4,824,853)

Rats are fasted overnight. Each animal is treated intravenously with the desired dose of the compound to be tested. One hour thereafter, the animal receives 1 ml of castor oil orally. Each animal should be kept in an individual cage and about 2 hours after the castor oil treatment, the presence or absence of diarrhea is noted. The $ED_{50}$ value is determined as that dose in mg/kg body weight, at which no diarrhea is present in 50% of the tested animals.

For example, young female Wistar rats (230–250 g. body weight) are fasted overnight and in the morning each animal is treated orally with a dose level of the compound to be tested. One hour thereafter, the animal receives 1 ml of castor oil orally. Each animal is kept in an individual cage. At different selected time intervals (e.g., 1, 2, 3, 4, 6 and 8 hrs), after the castor oil treatment, the presence or absence of diarrhea is noted. In more than 95% of 500 control animals, severe diarrhea is observed 1 hour after treatment with castor oil. Using this all-or-none criterion, a significant positive effect occurs with the tested compound if no diarrhea is observed 1 hour after the castor oil treatment. A minimum of 5 dose levels are used per drug, each dose level being given to 10 rats on ten different days. The $ED_{50}$ value, i.e., the dose level at which such effect is observed in 50% of the animals, for the compounds, such as the compounds of formula (II), generally ranges from about 0.01 to about 10 mg/kg.

(b) Castor oil test in mice (see, e.g., U.S. Pat. No. 4,326,075

Groups of mice are orally dosed with test compound and half hour later all mice are given 0.3 ml. of castor oil. Three hours after castor oil administration, all mice are checked for diarrhea and the dose of testing compound which protected 50% of mice for diarrhea is the $ED_{50}$ dose.

(c) Ricinus oil test (see, e.g., U.S. Pat. No. 4,990,521)

Rats, such as female Wistar rats or other laboratory strains, are fasted overnight. Each animal is treated orally with a dose level of the test compound. One hour thereafter, the animal is given an amount, typically 1 ml, of ricinus oil orally. Each animal is kept in an individual cage and 1 hour after the ricinus oil treatment, the presence or absence of diarrhea is noted. The $ED_{50}$ value is determined as that dose in mg/kg body weight, at which no diarrhea is present in 50% of the treated animals.

(d) Antagonism of $PGE_2$-induced diarrhea in mice

Anti-diarrheal activity can be determined by assessing the effects of a compound as an antagonist of $PGE_2$-induced diarrhea in mice (see, e.g., Dajani et al. 1975) *European Jour. Pharmacol.* 34:105–113; and Dajani et al. (1977) *J. Pharmacol. Exp. Ther.* 203:512–526; see, e.g., U.S. Pat. No. 4,870,084). This method reliably elicits diarrhea in otherwise untreated mice within 15 minutes. Animals that are pretreated with the test agent in which no diarrhea occurs are considered protected by the test agent. The constipating effects of test agents are measured as an "all or none" response, and diarrhea is defined as watery unformed stools, very different from normal fecal matter, which contains well-formed boluses, firm and relatively dry.

Standard laboratory mice, such as albino mice of the Charles River CD-1 strain, are used. They are typically kept in group cages. The weight range of the animals when tested is between 20–25 g. Pelleted rat chow is available ad libitum until 18 hours prior to testing, at which time food is withdrawn. Animals are weighed and marked for identification. Five animals are normally used in each drug treatment group and compared with controls. Mice weighing 20–25 g are housed in group cages, and fasted overnight prior to testing. Water is available. Animals are challenged with $PGE_2$ (0.32 mg/kg i.p. in 5% ETOH) one hour after test drug treatment, and immediately placed individually, for example, in transparent acrylic boxes. A disposable cardboard sheet on the bottom of the box is checked for diarrhea on an all or nothing basis at the end of 15 minutes.

C. Formulation of compositions for in vivo use and methods of use

Effective concentrations of one or more of antihyperalgesic compounds or pharmaceutically acceptable derivatives thereof are mixed with a suitable pharmaceutical carrier or vehicle for topical or local administration. Compounds are included in an amount effective for reducing the hyperalgesic state for which treatment is contemplated. The concentration of active compound in the composition will depend on absorption, inactivation, excretion rates of the active compound, the dosage schedule, and amount administered as well as other factors known to those of skill in the art. Generally, the dosages are higher, typically at least about 5 to 10 fold, than the amount delivered when administered orally or rectally for diarrhea or when administered as for treatment of respiratory disorders, and, if necessary may be empirically determined.

Pharmaceutical carriers or vehicles suitable for administration of the compounds and for the methods provided herein include any such carriers known to those skilled in the art to be suitable for the particular mode of administration. In addition, the compounds may be formulated as the sole pharmaceutically active ingredient in the composition or may be combined with other active ingredients.

Typically a therapeutically effective dosage is formulated to contain a concentration (by weight) of at least about 0.1% up to about 50% or more, preferably more than 1% of the active compound to the treated tissue. The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the hyperalgesic condition and may be empirically determined.

Compounds are typically included at concentrations 0.001% (by weight) or greater than 1% up to 50% or higher (for purposes herein the concentrations are set forth with reference to loperamide; for other compounds the concentrations may be greater or lesser depending upon their relative potency as anti-hyperalgesics compared to loperamide). The concentration is generally greater than the concentration for systemic administration of the compound as an anti-diarrheal. Preferable concentrations (by weight) are in the range of 0.01% to about 25%, more preferably 1% to 25%, yet more preferably greater than about 1% to about 10%, and most preferably greater than 1% up to about 5%. Aqueous suspensions and compositions contain 1% or more.

The resulting mixture may be a solution, suspension, emulsion or the like and are formulated as creams, gels, ointments, emulsions, solutions, elixirs, lotions, suspensions, tinctures, pastes, foams, aerosols, irrigations, sprays, suppositories, bandages, or any other formulation suitable for topical or local administration.

The intended route of administration herein is topical or local administration, and compositions are formulated in a manner suitable for each route of administration. Preferred modes of administration include topical application to the skin, eyes or mucosa, and local application to the joints, such as by intra-articular injection. Thus, typical vehicles are those suitable for pharmaceutical or cosmetic application to body surfaces or for local injection.

Pharmaceutical and cosmetic carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients. The active compound is included in the carrier in an amount sufficient to exert a therapeutically useful effect in the absence of serious toxic effects on the treated individual. The effective concentration may be determined empirically by testing the compounds using in vitro and in vivo systems, including the animal models described herein.

For topical administration, the compounds may be formulated in compositions in the form of gels, creams, lotions, solids, solutions or suspensions, or aerosols. Compositions for treating human skin are formulated for topical application with an anti-hyperalgesic effective amount of one or more the compounds selected as described herein, preferably one of those of the above-defined formula (I), in an effective concentration range (by weight), between about 0.1% and 80%, preferably 0.1 to 50%, more preferably greater than about 1% up to about 50% or more in a cream, ointment, lotion, gel, solution or solid base or vehicle known in the art to be non-toxic and dermatologically acceptable or suitable for application to the mucosa. Aqueous suspensions are preferably formulated at concentrations greater than about 1%, more preferably 2%.

To formulate a composition, the weight fraction of compound is dissolved, suspended, dispersed, or otherwise mixed in a selected vehicle at an effective concentration such that the hyperalgesic condition is relieved or ameliorated. Generally, emollient or lubricating vehicles that help hydrate the skin are more preferred than volatile vehicles, such as ethanol, that dry the skin. Examples of suitable bases or vehicles for preparing compositions for use with human skin are petrolatum, petrolatum plus volatile silicones, lanolin, cold cream (USP), and hydrophilic ointment (USP).

The choice of an acceptable vehicle is largely determined by the mode of application and tissue to be treated. Suitable pharmaceutically and dermatologically acceptable vehicles for topical application include those suited for use include lotions, creams, solutions, gels, tapes and the like. Generally, the vehicle is either organic in nature or an aqueous emulsion and capable of having the selected compound or compounds, which may be micronized, dispersed, suspended or dissolved therein.

The vehicle may include pharmaceutically-acceptable emollients, skin penetration enhancers, coloring agents, fragrances, emulsifiers, thickening agents, and solvents.

For local internal administration, such as intra-articular administration, the compounds are preferably formulated as a suspension in an aqueous-based medium, such as isotonically buffered saline or are combined with a biocompatible support or bioadhesive intended for internal administration.

1. Lotions

The lotions contain an effective concentration of one or more of the compounds. The effective concentration is preferably effective to deliver an anti-hyperalgesic amount, typically at a concentration of between about 0.1–50% (by weight) or more of one or more of the compounds provided herein. The lotions also contain (by weight) from 1% to 50%, preferably from 3% to 15%, of an emollient and the balance water, a suitable buffer, a $C_2$ or $C_3$ alcohol, or a mixture of water or the buffer and the alcohol. Any emollients known to those of skill in the art as suitable for application to human skin may be used. These include, but are not limited to, the following:

(a) Hydrocarbon oils and waxes, including mineral oil, petrolatum, paraffin, ceresin, ozokerite, microcrystalline wax, polyethylene, and perhydrosqualene.

(b) Silicone oils, including dimethylpolysiloxanes, methylphenylpolysiloxanes, water-soluble and alcohol-soluble silicone-glycol copolymers.

(c) Triglyceride fats and oils, including those derived from vegetable, animal and marine sources. Examples include, but are not limited to, castor oil, safflower oil, cotton seed oil, corn oil, olive oil, cod liver oil, almond oil, avocado oil, palm oil, sesame oil, and soybean oil.

(d) Acetoglyceride esters, such as acetylated monoglycerides.

(e) Ethoxylated glycerides, such as ethoxylated glyceryl monstearate.

(f) Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, isopropyl myristate, decyl oleate, isodecyl oleate, hexadecyl stearate, decyl stearate, isopropyl isostearate, diisopropyl adipate, diisohexyl adipate, dihexyidecyl adipate, diisopropyl sebacate, lauryl lactate, myristyl lactate, and cetyl lactate.

(g) Alkenyl esters of fatty acids having 10 to 20 carbon atoms. Examples thereof include, but are not limited to, oleyl myristate, oleyl stearate, and oleyl oleate.

(h) Fatty acids having 9 to 22 carbon atoms. Suitable examples include, but are not limited to, pelargonic, lauric, myristic, palmitic, stearic, isostearic, hydroxystearic, oleic, linoleic, ricinoleic, arachidonic, behenic, and erucic acids.

(i) Fatty alcohols having 10 to 22 carbon atoms, such as, but not limited to, lauryl, myristyl, cetyl, hexadecyl, stearyl, isostearyl, hydroxystearyl, oleyl, ricinoleyl, behenyl, erucyl, and 2-octyl dodecyl alcohols.

(j) Fatty alcohol ethers, including, but not limited to ethoxylated fatty alcohols of 10 to 20 carbon atoms, such as, but are not limited to, the lauryl, cetyl, stearyl, isostearyl, oleyl, and cholesterol alcohols having attached thereto from 1 to 50 ethylene oxide groups or 1 to 50 propylene oxide groups or mixtures thereof.

(k) Ether-esters, such as fatty acid esters of ethoxylated fatty alcohols.

(l) Lanolin and derivatives, including, but not limited to, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohols-esters, hydrogenolysis of lanolin, ethoxylated hydrogenated lanolin, ethoxylated sorbitol lanolin, and liquid and semisolid lanolin absorption bases.

(m) Polyhydric alcohols and polyether derivatives, including, but not limited to, propylene glycol, dipropylene glycol, polypropylene glycol (M.W.

2000–4000), polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol (M.W. 200–6000), methoxy polyethylene glycols 350, 550, 750, 2000, 5000, poly (ethylene oxide) homopolymers (M.W. 100,000–5,000,000), polyalkylene glycols and derivatives, hexylene glycol (2-methyl-2,4-pentanediol), 1,3-butylene glycol, 1,2,6,-hexanetriol, ethohexadiol USP (2-ethyl-1,3-hexanediol), $C_{15}$–$C_{18}$ vicinal glycol and polyoxypropylene derivatives of trimethylolpropane.

(n) Polyhydric alcohol esters, including, but not limited to, ethylene glycol mono- and di-fatty acid esters, diethylene glycol mono- and di-fatty acid esters, polyethylene glycol (M.W. 200–6000), mono- and di-fatty esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters.

(o) Wax esters, including, but not limited to, beeswax, spermaceti, myristyl myristate, and stearyl stearate and beeswax derivatives, including, but not limited to, polyoxyethylene sorbitol beeswax, which are reaction products of beeswax with ethoxylated sorbitol of varying ethylene oxide content that form a mixture of ether-esters.

(p) Vegetable waxes, including, but not limited to, carnauba and candelilla waxes.

(q) Phospholipids, such as lecithin and derivatives.

(r) Sterols, including, but not limited to, cholesterol and cholesterol fatty acid esters.

(s) Amides, such as fatty acid amides, ethoxylated fatty acid amides, and solid fatty acid alkanolamides.

The lotions further preferably contain (by weight) from 1% to 10%, more preferably from 2% to 5%, of an emulsifier. The emulsifiers can be nonionic, anionic or cationic. Examples of satisfactory nonionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol wherein the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers includ, but are not limited to, the fatty acid soaps, e.g. sodium, potassium and triethanolamine soaps, wherein the fatty acid moiety contains from 10 to 20 carbon atoms. Other suitable anionic emulsifiers include, but are not limited to, the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Among satisfactory cationic emulsifiers are quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably the compound, such as loperamide, is dissolved, suspended or otherwise uniformly dispersed in the mixture.

Other conventional components of such lotions may be included. One such additive is a thickening agent at a level from 1% to 10% by weight of the composition. Examples of suitable thickening agents include, but are not limited to: cross-linked carboxypolymethylene polymers, ethyl cellulose, polyethylene glycols, gum tragacanth, gum kharaya, xanthan gums and bentonite, hydroxyethyl cellulose, and hydroxypropyl cellulose.

2. Creams

The creams are formulated to contain concentration effective to deliver an anti-hyperalgesic effective amount of the compound to the treated tissue, typically at between about 0.1%, preferably at greater than 1% up to and greater than 50%, preferably between about 3% and 50%, more preferably between about 5% and 15% of one or more the compounds provided herein. The creams also contain from 5% to 50%, preferably from 10% to 25%, of an emollient and the remainder is water or other suitable non-toxic carrier, such as an isotonic buffer. The emollients, as described above for the lotions, can also be used in the cream compositions. The cream may also contain a suitable emulsifier, as described above. The emulsifier is included is in the composition at a level from 3% to 50%, preferably from 5% to 20%.

3. Solutions and suspensions for topical and local administration

The solutions are formulated to contain an amount of one or more compounds effective to deliver a an anti-hyperalgesic amount, typically at a concentration (by weight) of between about 0.1–50%, preferably at least more than 1%, more preferably more than 2%, of one or more of the compounds provided herein. The balance is water, a suitable organic solvent or other suitable solvent or buffer. Suitable organic materials useful as the solvent or a part of a solvent system are as follows: propylene glycol, polyethylene glycol (M.W. 200–600), polypropylene glycol (M.W. 425–2025), glycerine, sorbitol esters, 1,2,6-hexanetriol, ethanol, isopropanol, diethyl tartrate, butanediol, and mixtures thereof. Such solvent systems can also contain water.

Solutions or suspensions used for local application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediamine-tetraacetic acid (EDTA); buffers, such as acetates, citrates and phosphates; and agents for the adjustment of tonicity such as sodium chloride or dextrose. Liquid preparations can be enclosed in ampules, disposable syringes or multiple dose vials made of glass, plastic or other suitable material. Suitable carriers may include physiological saline or phosphate buffered saline (PBS), and the suspensions and solutions may contain thickening and solubilizing agents, such as glucose, polyethylene glycol, and polypropylene glycol and mixtures thereof. Liposomal suspensions, may also be suitable as pharmaceutically acceptable carriers. These may be prepared according to methods known to those skilled in the art.

These compositions that are formulated as solutions or suspensions may be applied to the skin, or, may be formulated as an aerosol or foam and applied to the skin as a spray-on. The aerosol compositions typically contain (by weight) from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used as understood in the art in a quantity and under a pressure suitable to expel the contents of the container.

Suitably prepared solutions and suspensions may also be topically applied to the eyes and mucosa. Solutions, particularly those intended for ophthalmic use, may be formulated as 0.01%–10% isotonic solutions, pH about 5–7, with appropriate salts, and preferably containing one or more of the compounds herein at a concentration of about 0.1%, preferably greater than 1%, up to 50% or more. Suitable ophthalmic solutions are known (see, e.g., U.S. Pat. No. 5,116,868, which describes typical compositions of ophthalmic irrigation solutions and solutions for topical application). Such solutions, which have a pH adjusted to about 7.4, contain, for example, 90–100 mM sodium chloride, 4–6 mM dibasic potassium phosphate, 4–6 mM dibasic sodium phosphate, 8–12 mM sodium citrate, 0.5–1.5 mM magnesium chloride, 1.5–2.5 mM calcium chloride, 15–25 mM sodium acetate, 10–20 mM D.L.-sodium, β-hydroxybutyrate and 5–5.5 mM glucose.

The active materials can also be mixed with other active materials, that do not impair the desired action, or with materials that supplement the desired action, including viscoelastic materials, such as hyaluronic acid, which is sold under the trademark HEALON (solution of a high molecular weight (MW of about 3 millions) fraction of sodium hyaluronate; manufactured by Pharmacia, Inc. see, e.g., U.S. Pat. Nos. 255,292,362, 5,282,851, 5,273,056, 5,229,127, 4,517, 295 and 4,328,803), VISCOAT (fluorine-containing (meth) acrylates, such as, 1H,1H,2H,2H-heptadecafluorodecylmethacrylate; see, e.g., U.S. Pat. Nos. 5,278,126, 5,273,751 and 5,214,080; commercially available from Alcon Surgical, Inc.), ORCOLON (see, e.g., U.S. Pat. No. 5,273,056; commercially available from Optical Radiation Corporation), methylcellulose, methyl hyaluronate, polyacrylamide and polymethacrylamide (see, eg., U.S. Pat. No. 5,273,751). The viscoelastic materials are present generally in amounts ranging from about 0.5 to 5.0%, preferably 1 to 3% by weight of the conjugate material and serve to coat and protect the treated tissues. The compositions may also include a dye, such as methylene blue or other inert dye, so that the composition can be seen when injected into the eye or contacted with the surgical site during surgery.

4. Gels

Gel compositions can be formulated by simply admixing a suitable thickening agent to the previously described solution or suspension compositions. Examples of suitable thickening agents have been previously described with respect to the lotions.

The gelled compositions contain an effective amount of one or more an anti-hyperalgesic amount, typically at a concentration of between about 0.1–50% by weight or more of one or more of the compounds provided herein.; from 5% to 75%, preferably from 10% to 50%, of an organic solvent as previously described; from 0.5% to 20%, preferably from 1% to 10% of the thickening agent; the balance being water or other aqueous carrier.

5. Solids

Compositions of solid forms may be formulated as stick-type compositions intended for application to the lips or other parts of the body. Such compositions contain an effective amount of one or more of the compounds provided herein. The amount is typically an amount effective to deliver an anti-hyperyperalgesic amount, typically at a concentration of between about 0.1–50% or more of one or more of the compounds provided herein. The solids also contain from about 40% to 98%, preferably from about 50% to 90%, of the previously described emollients. This composition can further contain from 1% to 20%, preferably from 5% to 15%, of a suitable thickening agent, and, if desired or needed, emulsifiers and water or buffers. Thickening agents previously described with respect to lotions are suitably employed in the compositions in solid form.

Other ingredients, such as preservatives, including methyl-paraben or ethyl-paraben, perfumes, dyes or the like, that are known in the art to provide desirable stability, fragrance or color, or other desirable properties, such as shielding from actinic rays from the sun, to compositions for application to the skin may also be employed in a composition for such topical application.

6. Additional ingredients

Other active ingredients, include, but are not limited to antibiotics, antivirals, antifungals, anti-inflammatories, including steroidal and non-steroidal anti-inflammatories, anesthetics and mixtures thereof. Such additional ingredietns include any of the following:

a. Antibacterial agents

Aminoglycosides, such as Amikacin, Apramycin, Arbekacin, Bambermycins, Butirosin, Dibekacin, Dihdrostreptomycin, Fortimicin(s), Fradiomycin, Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid, and Tobramycin;

Amphenicols, such as Azidamfenicol, Chloramphenicol, Chloramphenicol Palmirate, Chloramphenicol Pantothenate, Florfenicol, Thiamphenicol;

Ansamycins, such as Rifamide, Rifampin, Rifamycin, and Rifaximin;

β-Lactams;

Carbapenems, such as Imipenem;

Cephalosporins, such as 1-Carba (dethia) Cephalosporin, Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefmetazole, Cefminox, Cefetan and Cefoxitin;

Monobactams such as Aztreonam, Carumonam and Tigemonam;

Oxacephems such as Flomoxef and Moxolactam;

Penicillins such as Amidinocillin, Amdinocillin Pivoxil, Amoxicillin, Ampicillan, Apalcillin, Aspoxicillin, Azidocillan, Azlocillan, Bacampicillin, Benzylpenicillinic Acid, Benzylpenicillin, Carbenicillin, Carfecillin, Carindacillin, Clometocillin, Cloxacillin, Cyclacillin, Dicloxacillin, Diphenicillin, Epicillin, Fenbenicillin, Floxicillin, Hetacillin, Lenampicillin, Metampicillin, Methicillin, Mezlocillin, Nafcillin, Oxacillin, Penamecillin, Penethamate Hydriodide, Penicillin G Benethamine, Penicillin G Benzathine, Penicillin G Benzhydrylamine, Penicillin G Calcium, Penicillin G Hydrabamine, Penicillin G Potassium, Penicillin G Procaine, Penicillin N, Penicillin O, Penicillin V, Penicillin V Benzathine, Penicillin V Hydrabamine, Penimepicycline, Phenethicillin, Piperacillin, Pivapicillin, Propicillin, Quinacillin, Sulbenicillin, Talampicillin, Temocillin and Ticarcillin;

Lincosamides such as Clindamycin and Lincomycin;

Macrolides such as Azithromycin, Carbomycin, Clarithromycin, Erythromycin(s) and Derivatives, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin β-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin and Zinc Bacitracin;

Tetracyclines such as Apicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and others such as Cycloserine, Mupirocin, Tuberin.

b. Synthetic antibacterials 2,4-Diaminopyrimidines such as Brodimoprim, Tetroxoprim and Trimethoprim;

Nitrofurans such as Furaltadone, Furazolium, Nifuradene, Nifuratel, Nifurfoline, Nifurpirinol, Nifurprazine, Nifurtoinol and Nitrofurantoin;

Quinolones and analogs thereof, such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Pefloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-B, Chloramine-T, Dichloramine T,Formosulfathiazole, $N^2$-Formyl-sulfisomidine, $N^4$-β-D-Glucosylsulfanilamide, Mafenide, 4'-(Methyl-sulfamoyl) sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, Sulfamidochrysoidine, Sulfamoxole, Sulfanilamide, Sulfanilamidomethanesulfonic Acid Triethanolamine Salt, 4-Sulfanilamidosalicylic Acid, $N^4$-Sulfanilylsulfanilamide, Sulfanilylurea, N-Sulfanilyl-3,4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones, such as Acedapsone, Acediasulfone, Acetosuffone, Dapsone, Diathymosulfone, Glucosulfone, Solasulfone, Succisulfone, Sulfanilic Acid,p-Sulfanilylbenzylamine, p,p'-Sulfonyldianiline-N,N' digalactoside, Sulfoxone and Thiazolsulfone;

Others such as Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine, and Xibornol.

c. Antifungal (antibiotics)

Polyenes such as Amphotericin-B, Candicidin, Dermostatin, Filipin, Fungichromin, Hachimycin, Hamycin, Lucensomycin, Mepartricin, Natamycin, Nystatin, Pecilocin, Perimycin; and others, such as Azaserine, Griseofulvin, Oligomycins, Pyrrolnitrin, Siccanin, Tubercidin and Viridin.

d. Antifungal (synthetic)

Allylamines such as Naftifine and Terbinafine;

Imidazoles such as Bifonazole, Butoconazole, Chlordantoin, Chlormidazole, Cloconazole, Clotrimazole, Econazole, Enilconazole, Fenticonazole, Isoconazole, Ketoconazole, Miconazole, Omoconazole, Oxiconazole Nitrate, Sulconazole and Tioconazole;

Triazoles such as Fluconazole, Itraconazole, Terconazole

Others such as Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionates, Propionic Acid, Pyrithione, Salicylanilide, Sulbentine, Tenonitrozole, Tolciclate, Tolindate, Tolnaftate, Tricetin, Ujothion, and Undecylenic Acid.

e. Antiglaucoma agents

Antiglaucoma agents, such as Dapiprazoke, Dichlorphenamide, Dipivefrin and Pilocarpine.

f. Anti-inflammatory agents

Corticosteriods, Aminoarylcarboxylic Acid Derivatives such as Etofenamate, Meclofenamic Acid, Mefanamic Acid, Niflumic Acid;

Arylacetic Acid Derivatives such as Acemetacin, Amfenac, Cinmetacin, Clopirac, Diclofenac, Fenclofenac, Fenclorac, Fenclozic Acid, Fentiazac, Glucametacin, Isoxepac, Lonazolac, Metiazinic Acid, Oxametacine, Proglumetacin, Sulindac, Tiaramide and Tolmetin;

Arylbutyric Acid Derivatives such as Butibufen and Fenbufen;

Arylcarboxylic Acids such as Clidanac, Ketorolac and Tinoridine.

Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen, Protizinic Acid and Tiaprofenic Acid;

Pyrazoles such as Mepirizole;

Pyrazolones such as Clofezone, Feprazone, Mofebutazone, Oxyphenbutazone, Phenylbutazone, Phenyl Pyrazolidininones, Suxibuzone and Thiazolinobutazone;

Salicylic Acid Derivatives such as Bromosaligenin, Fendosal, Glycol Salicylate, Mesalamine, 1-Naphthyl Salicylate, Olsalazine and Sulfasalazine;

Thiazinecarboxamides such as Droxicam, Isoxicam and Piroxicam

Others such as ε-Acetamidocaproic Acid, S-Adenosylmethionine, 3-Amino-4-hydroxybutyric Acid, Amixetrine, Bendazac, Bucolome, Carbazones, Difenpiramide, Ditazol, Guaiazulene, Heterocylic Aminoalkyl Esters of Mycophenolic Acid and Derivatives, Nabumetone, Nimesulide, Orgotein, Oxaceprol, Oxazole Derivatives, Paranyline, Pifoxime, 2-substituted-4, 6-di-tertiary-butyl-s-hydroxy-1,3-pyrimidines, Proquazone and Tenidap.

g. Antiseptics

Guanidines such as Alexidine, Ambazone, Chlorhexidine and Picloxydine;

Halogens/Halogen Compounds such as Bornyl Chloride, Calcium Iodate, Iodine,Iodine Monochloride, Iodine Trichloride, Iodoform, Povidone-Iodine, Sodium Hypochlorite, Sodium Iodate, Symclosene, Thymol Iodide, Triclocarban, Triclosan and Troclosene Potassium;

Nitrofurans such as Furazolidone, 2-(Methoxymethyl)-5-Nitrofuran, Nidroxyzone, Nifuroxime, Nifurzide and Nitrofurazone;

Phenols such as Acetomeroctol, Chloroxylenol, Hexachlorophene, 1-Napthyl Salicylate, 2,4,6-Tribromo-m-cresol and 3',4',5-Trichlorosalicylanilide;

Quinolines such as Aminoquinuride, Chloroxine, Chlorquinaldol, Cloxyquin, Ethylhydrocupreine, Halquinol, Hydrastine, 8-Hydroxquinoline and Sulfate; and others, such as Boric Acid, Chloroazodin, m-Cresyl Acetate, Cupric Sulfate and Ichthammol.

h. Antivirals

Purines/Pyrimidinones, such as 2-Acetyl-pyridine 5-((2-pyridylamino)thiocarbonyl) Thiocarbonohydrazone, Acyclovir, Dideoxyadenosine, Dideoxycytidine, Dideoxyinosine, Edoxudine, Floxuridine, Ganciclovir, Idoxuridine, MADU, Pyridinone, Trifluridine, Vidrarbine and Zidovudiine;

Others such as Acetylleucine Monoethanolamine, Acridinamine, Alkylisooxazoles, Amantadine, Amidinomycin, Cuminaldehyde Thiosemicarbzone, Foscarnet Sodium, Kethoxal, Lysozyme, Methisazone, Moroxydine, Podophyllotoxin, Ribavirin, Rimantadine, Stallimycin, Statolon, Thymosins, Tromantadine and Xenazoic Acid.

Exemplary compositions are set forth in the Examples herein.

D. Combinations and kits

The compounds or compositions containing the compounds may also be coated on bandages, mixed with bioadhesives or included in dressings. Thus, combinations of bandages, bioadhesives, dressings and other such materials and the compositions formulated as described herein are provided. Kits containing these combinations, which may also include compositions containing the above listed agents, are also provided.

E. Articles of manufacture

The compounds and compositions provided herein may be packaged as articles of manufacture containing packaging material, one or more of the compounds provided herein, which is effective for ameliorating peripheral hyperalgesia, within the packaging material, and a label that indicates that the compound, N-oxide, acid, salt or other derivative thereof is used for treating hyperalgesic conditions.

F. Methods of treatment

Compositions for use with human skin preferably may be applied at least once per day or, if necessary to achieve the desired result, more often, to the areas of the skin for which treatment is sought. It is understood that the precise treatment regimen depends upon the individual treated and may be ascertained empirically depending upon the formulation and, particularly, the age of the treated individual. Any regimen is acceptable as long as the desired anti-hyperalgesic effects are achieved without substantial deleterious or sustained undesirable side effects.

The methods for treating human skin are practiced by applying to the skin, preferably at least daily, a composition suitable for human skin treatment or treatment of mucosal membranes and other body surface tissues, including the vagina, rectum, mouth, eyes and other such tissues. The compositions may be injected into joints or other inflamed areas.

Compositions may be combined with bandages, bioadhesives and other dressings and applied to the body in combination therewith.

The following examples are included for illustrative purposes only and are not intended to limit the scope of the invention.

EXAMPLE 1

Peripherally-mediated antinociceptive effects observed during inflammation appear to be mediated by $\mu$ and $\kappa$ opioids A. Materials and methods This study was performed with approval from the Institutional Animal Care and Use Committee of the University of California, San Diego.

1. Preparation

To induce inflammation, each rat (male Sprague-Dawley, 300–340 g) was anesthetized in a Plexiglas acrylic plastic induction chamber with 2% halothane in oxygen-enriched room air. During halothane anesthesia, 0.2 ml of a mixture of 4% kaolin and 4% carrageenan (Sigma Chemical Co.) was slowly injected into the right knee joint cavity through the patellar ligament using a 21 gauge needle. After induction of the inflammation, the rat was allowed to recover from anesthesia. Three and one-half hours after induction of the inflammation, the rat was anesthetized again with halothane (2.0%) in a 50% $O_2$/air mixture delivered through a face mask. The tail artery was cannulated for monitoring BP. When surgical preparation was completed, halothane anesthesia was continued at 1.0% inspired halothane. BP was recorded continuously (Grass model 7 polygraph). Body temperature (rectal) was monitored and maintained at 37° C. by a servo-controlled heating blanket. For intrathecal (IT) injection, rats were prepared with chronic lumbar intrathecal catheters (Yaksh et al. (1976) *Physiol. Behav.* 17:1031–1036). After 5–7 days, they were entered into the study.

To produce a reliable compression of the knee joint, a pediatric blood pressure cuff was placed around the inflamed knee. For stimulation, the cuff was rapidly elevated to 200 mm Hg by a syringe pump. Each inflation was sustained for 2 minutes. Typically, testing was carried out at −5 minutes, and 15, 30, 60, 90 and 120 minutes.

2. Measure of joint volume and circumference

To assure a standard state of inflammation, at three and one-half hours after kaolin and carrageenan injection, the volume and circumference of the inflamed and non-inflamed knee joint were measured. Volume was assessed by displacement of fluid after the hindquarter of the rat was immersed to the groin. Circumference was measured by a flexible cord placed around the knee joint at the level of the knee joint flexure. After the first 85 rats, it was found that the inflammation was sufficiently reliable so that further screening in this fashion was not required.

3. Drug delivery

The route of drug injection was intramuscularly (IM) into the left hamstring muscle, intrathecally (IT) through the chronic catheter, or intraarticularly (IA) into the right knee joint using a 30 gauge needle. It was also found that simple IA injection of saline (vehicle) into the already inflamed knee joint at 4 hours would result in an additional facilitated response. Thus, to compare the potency of the IT and IM routes of delivery with the IA route, all IT and IM treatments employed a concurrent IA injection of saline, in addition to the IT or IM injection. IT and IM vehicle injection had no effect upon the response and, thus, it was not necessary to give parallel IT or IM vehicle injection with IA drugs. The volume of all IM and IA drug injections was 0.2 ml, except for IM injection of U50488H 10 mg, which was in 0.6 ml.

All IT administered drugs were injected in a volume of 10 μl followed by 10 μl of physiologic saline to clear the catheter.

4. Drugs

The drugs used for injection were:

mu (μ) agonists: morphine sulfate (MW: 334; Merck, Sharpe and Dohme, West Point, Pa.); Sufentanil citrate, (MW: 571 Janssen Pharmaceutical, Belgium);

kappa (κ) agonists: PD 11 7302 ((+/−)trans-N-methyl-N [2-(1-pyrrolidinyl)-cyclohexyl-]benzo-[b]-thiophene-4-acetamide] [MW–412; Park Davis] and U50488H (trans-3,4-dichloro-N-methyl-N-[2-(1-pyrrolidinyl)-cyclohexyl]-benzeneacetamide) (MW: 465; Upjohn, Kalamazoo, Mich.); Spiradoline mesylate (MW: 522; Research Biochemicals Inc.);

delta (δ) agonists: DADL (D-ala$^2$D-leu$^5$-enkephalin; MW: 556; courtesy Dr. Murray Goodman, UCSD); DPDPE: (D-Pen2, D-Pen$^5$)enkephalin (MW: 646, courtesy Dr. Victor Hruby, University of Arizona Health Science Center, Tucson, Ariz.); and naloxone HCl (MW=364; Endo Labs, Garden City, N.J.).

5. Naloxone antagonism

To define the potency of naloxone to reverse the effects of IA morphine and U50488H, rats received an injection of naloxone (intraperitoneal injection, mg/kg) given at −10 minutes before IA morphine (1 mg) IA U50488H (1 mg). This time interval was based on preliminary observations. If the naloxone dose completely reversed the effects of the agonist, it was scored as an antagonism. In sequential rats, the naloxone dose was increased or decreased by a factor of 3 (approximately one-half log unit: 0.01, 0.03, 0.1, 0.3, 1.0, 3.0 or 10.0 mg/kg) if the preceding naloxone dose was either ineffective or effective (e.g., the Dixon up-down method) for potency determination (Dixon, W J (1965) *Am. Stat. Ass. J.* 60:67–978).

6. Statistics:

BP was evaluated as the mean BP: ((systolic BP−diastolic BP)/3+diastolic BP). The response to a compression stimulus was expressed as Δ mean BP ((maximum mean blood pressure response observed during knee joing compression)−(mean blood pressure response observed immediately prior to knee joint compression)). For dose response analysis, data are presented as the % ΔBP (maximum Δ mean BP measured after drug)/maximum Δ mean BP measured before drug))×100. Statistical comparisons were carried out using a Student's t-test, paired or unpaired as required. For statistical analysis and graphical presentation, BP dose response curves were generated using the maximum reduction in the evoked response (% Δ.BP) observed within 60 minutes after drug injection. These dose response data were analyzed by calculation of a least-squares linear regression. ED$_{50}$ and slopes with 95% confidence interval (CI) were calculated (Tallarida et al.(1986) *Manual of Pharmacologic calculations with computer programs,* 2nd ed., New York, Springer-Verlag).

B. Results

1. General observations

In all experiments, the injection of kaolin and carrageenan induced inflammation, with swelling and edematous deformation of the joint. The volume of the right injected hindlimb was measured in the first 85 rats and found to be 6.6±0.1 versus 14.6±0.5 ml, respectively, before and after kaolin and carrageenan injection (n=85; Δ=+1.8±0.1 ml, p<0.01, paired t-test). Injection of saline alone resulted in a small, but not statistically significant, increase in the circumference of the injected knee joint. The left, uninjected knee, was not different from the right knee prior to kaolin and carrageenan and did not change during the study (p>0.10, paired t-test data, not shown). Prior to blood pressure response testing, it was observed that all rats displayed a tendency to keep the injected limb from weight bearing. Unstimulated rats (n=193), maintained in an anesthetic state with inspired 1.0% halothane, displayed a stable resting BP (121±6 mm Hg). Inflation of the cuff on the inflamed knee joint resulted in a reliable stimulation-dependent increase in BP during the 2 minute interval of inflation (Δ=14.6±0.2 mmHg). With knee joint compression, the time course of the increasing BP evoked by compression was uniform, reaching the maximum response approximately 20–30 seconds after the onset of stimulation. The BP changes persisted throughout 2 minutes of stimulation and gradually returned to the control level within 1–2 minutes after the end of the stimulus.

In the absence of drug treatment, the response to compression was stable over the 2 hour interval of testing.

2. Intrathecal opioid agonists

The IT administration of μ, δ and κ agonists at the doses employed had no statistically significant effect upon resting blood pressure, but resulted in an early blockade of the cuff-evoked increase in BP. The antinociceptive effects were dose dependent. The order of drug activity on the cuff-evoked BP responses was sufentanil>PD117302, Spiradoline, morphine>DADL, DPDPE>U-50,488H=naloxone=0.

3. Intramuscular opioid agonist-cardiovascular response

To determine if the IA effects could be similarly achieved by a "systemic" route of delivery, the intramuscular (IM) administration of these agents was also examined. IM μ opioid agonists resulted in a blockade of the compression-evoked increase in BP. The ordering of activity was sufentanil >PD117302, Spiradoline, morphine>DADL, DPDPE>U-50,488H=naloxone=0.

4. Naloxone antagonism

The effects of IM naloxone on the depressive effects of IA morphine (1 mg) and IA U50488H were determined. Naloxone alone was without effect upon a compression-evoked change in BP. To determine if the effects of naloxone were local, within the articular space, naloxone (30 μg) was co-administered with morphine in 4 rats. This injection was adequate to attenuate the anti-hyperalgesic effects of morphine otherwise observed at 30 minutes after agonist injection.

C. Discussion

1. Spinal opioid agonists and antinociception

The compression evoked increase in BP was effectively blocked by the intrathecal delivery of morphine sufentanil (μ) and DPDPE/DADL (δ), PD117304, spiradoline and U50488 (κ). Spinally delivered opioid μ and δ agonists have been shown to depress the behavioral and electrophysiological responses evoked by noxious stimulation. In contrast, κ agonists frequently appear to have modest effects in behavioral models of acute nociception (such as the tail flick or hot plate models), but typically appear to be more efficacious in models of protracted pain (typically induced by inflammatory stimuli as in the present model). Given the lack of significant changes in resting blood pressure with the spinal agent, it appears that these agents are blocking the response by a blockade of small afferent input generated by the compression of the inflamed knee.

2. Intra-articular opioid agonists and antinociception

The experiments demonstrated that IA administered μ and κ, but not δ, preferring agonists result in a dose dependent blockade of the hyperalgesia produced by the inflammation of the knee. Importantly, as defined by the dose response curves, the effects produced by injection at the site is more robust and potent than when the respective agent is delivered intramuscularly. This observation indicates that the effect of IA μ and κ agonists are appear to be mediated by a local action at the site of injection. This local action is further supported by the observation that local naloxone was able at a very low dose to attenuate the effects of IA morphine. The local dose required to induce this blockade considerably exceeds that dose required after spinal delivery. This difference in potency by the two "local" routes may reflect the accessibility of the joint to the drug. Alternately, the high dose may reflect upon the fact that a high level of occupancy is required to block the transduction.

Antagonism of the effect of IA morphine and U50488H is consistent with the known lower affinity of naloxone for the κ receptor than for the μ receptor and indicates that both classes of receptors appear to be involved in this action. The failure of DPDPE and DADL to induce a comparable action may be due to the absence of delta receptors at this site or to a difference in bio-availability.

EXAMPLE 2

The effects of intra-articular loperamide were compared with those of orphine delivered into the inflamed knee joints of rats A. Model In joint inflammation, the peripheral nerve innervating inflamed issue evokes an exaggerated behavior response to otherwise innocuous stimuli (i.e. a state of hyperalgesia). This scenario has been well-documented in the knee joint. It has been shown that inflammation of the knee joint results in, among other responses, signs of a pain-associated autonomic reaction, including increased BP.

B. Methods

1. Induction of inflammation

Male rats (Sprague-Dawley, 300–340 g) were anesthetized with 2% halothane in oxygen-enriched room air. To induce inflammation, during halothane anesthesia 0.2 ml of a mixture of 4% kaolin and 4% carrageenan (Sigma Chemical Co.) was injected into the right knee joint cavity through the patellar ligament using a 21 gauge needle. This induces an experimental arthritis and model of hyperalgesia.

After induction of the inflammation, the rat was allowed to recover from anesthesia. Three and half hours after induction of the inflammation, the rat was anesthetized again with halothane (2.0%) in oxygen-enriched air. The tail artery was cannulated for monitoring BP. When surgical preparation was completed, halothane anesthesia was continued at 1.0% inspired halothane. BP was recorded continuously (Grass model 7 polygraph). Body temperature (rectal) was monitored and maintained at 37° C. by a servo-controlled heating blanket. To produce a reliable compression of the knee joint, a pediatric blood pressure cuff was placed around the inflamed knee. For stimulation, the cuff was rapidly elevated to 22 mm Hg by a syringe pump. Each inflation was sustained for 2 minutes. It has been demonstrated that such compression results in a reliable stimulus dependent hypertension (Δ≈13 mm Hg).

2. Drugs and drug delivery

Drugs were delivered either intramuscularly (IM) into the left hamstring muscle, or intra-articularly (IA) into the right knee joint using a 30 gauge needle. The volume of all IM and IA drug injections was 0.2 ml. Drugs used for injection were: morphine sulfate (Merck, Sharpe and Dohme, West Point, Pa.), and loperamide HCl (Research Biochemicals, Natick, Mass.). All drugs were dissolved in dimethylsulfoxide (DMS, spectral grade) and diluted with 5% methylcellulose (Sigma). Naloxone HCl (Dupont) was prepared in saline for intraparenteral (IP) delivery.

C. Results

The following reflects experiments targeted to define i) the effect of the IM versus IA loperamide and morphine in blocking the compression evoked change in blood pressure in the inflamed knee joint, and ii) the supra spinal effects.

1. Effects upon resting and compression evoked blood pressure

The IA administration of morphine (3 mg), and loperamide (0.3 mg) had no effect upon resting blood pressure. IA morphine and IA loperamide, however, resulted in a dose dependent blockage of the cuff-evoked increase in BP (Table below). In contrast to the effects of IA injection, the injection of the same doses in the contralateral leg had minimal suppressive effect upon the compression evoked response. The effects of IA loperamide were reversed by pretreatment with naloxone. IA morphine is similarly reversed in this model (data not shown).

TABLE

Summary of effect of intra-articular (IA) and intramuscular (IM) loperamide or morphine on the resting blood pressure and the pressure change evoked by compression of the inflamed knee joint.

| | Resting BP (mm Hg) | | Compression evoked BP |
|---|---|---|---|
| | Pre Drug | Post Drug | (ΔPost drug/%ΔPre Drug) × 100* |
| | IA Vehicle (control) | | |
| Rat 1 | 121 | 113 | 110 |
| Rat 2 | 110 | 121 | 98 |
| Rat 3 | 109 | 109 | 89 |
| Rat 4 | 89 | 91 | 114 |
| μ ± SE | 107 ± 13 | 109 ± 13 | 103 ± 11 |
| | IA Morphine† | | |
| Rat 5 | 86 | 91 | 3 |
| Rat 6 | 112 | 102 | 12 |
| Rat 7 | 92 | 105 | 15 |
| Rat 8 | 86 | 92 | 7 |
| μ ± SE | 94 ± 12 | 98 ± 7 | 9 ± 5 |
| | IA Loperamide† | | |
| Rat 9 | 69 | 73 | 18 |
| Rat 10 | 103 | 109 | 21 |
| Rat 11 | 115 | 109 | 26 |
| Rat 12 | 102 | 115 | 29 |
| μ ± SE | 97 ± 19 | 102 ± 19 | 24 ± 5 |
| | IM Morphine† | | |
| Rat 13 | 115 | 119 | 63 |
| Rat 14 | 93 | 103 | 79 |
| Rat 15 | 89 | 111 | 58 |
| Rat 16 | 101 | 89 | 67 |
| μ ± SE | 100 ± 11 | 106 ± 13 | 67 ± 9 |
| | IM Loperamide†† | | |
| Rat 17 | 112 | 119 | 110 |
| Rat 18 | 128 | 106 | 101 |
| Rat 19 | 121 | 112 | 89 |
| Rat 20 | 105 | 100 | 91 |
| μ ± SE | 117 ± 10 | 109 ± 8 | 98 ± 10 |
| | IA Loperamide + Naloxone††† | | |
| Rat 21 | 89 | 110 | 115 |
| Rat 22 | 93 | 121 | 121 |
| Rat 23 | 119 | 123 | 118 |
| Rat 24 | 107 | 110 | 92 |
| μ ± SE | 102 ± 14 | 116 ± 7 | 112 ± 13 |

*%ΔPost drug: Percent change in blood pressure evoked by knee joint compression ((Post knee joint compression − pre knee joint precompression) × 100) measured after delivery
%ΔPre Drug: Percent change in blood pressure evoked by knee joint compression before drug delivery ((Post knee joint compression − pre knee joint compression) × 100) measured before drug delivery.
†3 mg
††0.3 mg
†††(1 mg/kg, IP)

2. Side effects of IM loperamide and morphine

Separate groups of unanesthetized rats were injected with IM morphine (3 mg) and/or loperamide (0.5 mg). The time the animal would stand poised in front of a 4 cm high bar was measured and defined as catalepsy. As shown in the Table below, morphine, but not loperamide treated rats, were significantly more cataleptic. Loperamide animals showed no sign of catalepsy.

TABLE

Incidence of catalepsy after IM Loperamide and Morphine

| | Time to Dismount from Bar (sec) | |
|---|---|---|
| | Before Drug | After Drug Treatment (15 min) |
| IM Morphine (3 mg) | | |
| Rat A | 1 | 29 |
| Rat B | 2 | 52 |
| Rat C | 1 | 37 |
| Rat D | 1 | 31 |
| $\mu \pm SE$ | 1 ± 1 | 37 ± 11 |
| IM Loperamide (0.5 mg) | | |
| Rat E | 1 | 1 |
| Rat F | 1 | 1 |
| Rat G | 1 | 3 |
| Rat H | 1 | 2 |
| $\mu \pm SE$ | 1 ± 0 | 2 ± 1 |

D. Conclusions

These data indicate the following:

i) Loperamide and morphine given into the inflamed knee joint will reduce the pain response evoked by knee joint compression.

ii) The effects are mediated by a local action as the same injection into the contralateral leg had no effect (e.g., the effects were not mediated by drug levels that were achieved by parenteral delivery).

iii) The effects of loperamide even at the maximal systemic concentration (achieved by the IM injection in the unanesthetized rat) was without effects on centrally mediated behavior (catalepsy).

iv) The effects of loperamide at this dose were reversed by the opiate receptor antagonist naloxone suggesting that loperamide was acting via an opiate receptor.

EXAMPLE 3

Preparation of petrolatum based water-washable ointment

A petrolatum based water-washable ointment is prepared by melting inert ingredients together, adding loperamide hydrochloride and mixing well until the resulting ointment congeals.

| | Weight (%) |
|---|---|
| Loperamide hydrochloride | 0.5 |
| Lanolin alcohol | 0.1 |
| Emulsifying wax NF | 7.5 |
| Peg-20 corn glycerides | 5.0 |
| Petrolatum | 86.0 |

EXAMPLE 4

Preparation of an oil-in-water creams

A. An oil-in-water cream is prepared from components (1) by heating water, propylene glycol, and Tween 20 (polysorbate) to 70–80° C., and then dissolving methylparaben and loperamide hydrochloride. The ingredients in (2) are then melted together at 70–80° C., and mixture (1) is added to mixture (2). The resulting composition is mixed until the cream congeals.

| | Weight (%) |
|---|---|
| (1) | |
| Loperamide hydrochloride | 1.75 |
| Propylene glycol | 38.5 |
| Methyl paraben | 0.30 |
| Tween 20 (Polysorbate) | 3.50 |
| Water | 29.95 |
| (2) | |
| White petrolatum | 18.20 |
| Stearyl alcohol | 5.00 |
| Isopropyl myristate | 2.50 |
| Liposorb S (sorbitan stearate) | 1.20 |
| Liposorb S 20 (polysorbate 60) | 3.10 |

B. Alternatively, oil-in-water creams are prepared by heating water, propylene glycol and polyethylene glycol 400 to 70–80° C. and adding a mixture of white petrolatum, stearyl alcohol and surfactant (also mixed at 70–80° C.). Then loperamide hydrochloride in benzyl alcohol is added and finally hydroxyethyl cellulose (optional) is added and the pH is adjusted to 7.5 with an appropriate buffer.

| | Weight % |
|---|---|
| (1) | |
| Loperamide hydrochloride | 5.0 |
| Benzyl alcohol | 2.0 |
| Propylene glycol | 5.0 |
| Polyethylene glycol 400 | 5.0 |
| White Petrolatum | 10.0 |
| Stearyl alcohol | 5.0 |
| Hydroxyethyl cellulose | — |
| Surfactant* | 5.0 |
| Water | qs 100 |
| Buffer to pH | 7.5 |
| (2) | |
| Loperamide hydrochloride | 5.0 |
| Benzyl alcohol | 2.0 |
| Propylene glycol | 5.0 |
| Polyethylene glycol 400 | 5.0 |
| White Petrolatum | 10.0 |
| Stearyl alcohol | 5.0 |
| Hydroxyethyl cellulose | — |
| Surfactant* | 5.0 |
| Water | qs 100 |
| Buffer to adjust pH | 7.5 |

*Surfactant may be selected from, but not limited to, the following three systems: Steareth 2 plus steareth 21, or sorbitan monooleate plus polyoxyl 40 stearate, or poloxamer.

EXAMPLE 5

Preparation of water washable gels

A water-washable gel is prepared by adding Transcutol (diethylene glycol monoethyl ether) to propylene glycol, then dissolving the parabens and loperamide hydrochloride. Then water and Natrosol are added and mixed well until the mixture gels.

|                                               | Weight % |
|-----------------------------------------------|----------|
| Loperamide hydrochloride                      | 4.00     |
| Propylene glycol                              | 55.00    |
| Transcutol (diethylene glycol monoethyl ether)| 5.00     |
| Natrosol 250 HHX (hydroxyethyl cellulose)     | 2.00     |
| Methyl paraben                                | 0.18     |
| Propyl paraben                                | 0.02     |
| Water                                         | 33.80    |

EXAMPLE 6
Preparation of aqueous gels

Aqueous gels are prepared by mixing loperamide hydrochloride, benzyl alcohol (and optionally propylene glycol and polyethylene glycol 400 as indicated in the ingredients list), adding to buffered water, and then adding hydroxyethyl cellulose with stirring until the mixture gels.

|                           | Weight % |
|---------------------------|----------|
| A.                        |          |
| Loperamide hydrochloride  | 5.0      |
| Benzyl alcohol            | 2.0      |
| Propylene glycol          | —        |
| Polyethylene glycol 400   | —        |
| Hydroxyethyl cellulose    | 1.5      |
| Water                     | qs 100   |
| Buffer to pH              | 6.5      |
| B.                        |          |
| Loperamide hydrochloride  | 5.0      |
| Benzyl alcohol            | 2.0      |
| Propylene glycol          | —        |
| Polyethylene glycol 400   | —        |
| Hydroxyethyl cellulose    | 1.5      |
| Water                     | qs 100   |
| Buffer to pH              | 7.5      |
| C.                        |          |
| Loperamide hydrochloride  | 5.0      |
| Benzyl alcohol            | 2.0      |
| Propylene glycol          | —        |
| Polyethylene glycol 400   | —        |
| Hydroxyethyl cellulose    | 1.5      |
| Water                     | qs 100   |
| Buffer to pH              | 8.5      |
| D.                        |          |
| Loperamide hydrochloride  | 5.0      |
| Benzyl alcohol            | 2.0      |
| Propylene glycol          | 5.0      |
| Polyethylene glycol 400   | —        |
| Hydroxyethyl cellulose    | 1.5      |
| Water                     | qs 100   |
| Buffer to pH              | 7.5      |
| E.                        |          |
| Loperamide hydrochloride  | 5.0      |
| Benzyl alcohol            | 2.0      |
| Propylene glycol          | 5.0      |
| Polyethylene glycol 400   | 5.0      |
| Hydroxyethyl cellulose    | 1.5      |
| Water                     | qs 100   |
| Buffer to pH              | 7.5      |

EXAMPLE 7
Preparation of polyethylene glycol water-washable ointments

Polyethylene glycol water-washable ointments are prepared by mixing loperamide hydrochloride in benzyl alcohol and propylene glycol, adding polyethylene glycol 400 and 3350 and adjusting to pH 7.5 with buffer.

|                           | Weight % |
|---------------------------|----------|
| A.                        |          |
| Loperamide hydrochloride  | 5.0      |
| Benzyl alcohol            | 5.0      |
| Propylene glycol          | 5.0      |
| Polyethylene glycol 3350  | 40.0     |
| Polyethylene glycol 400   | qs 100   |
| Buffer to pH              | 7.5      |
| B.                        |          |
| Loperamide hydrochloride  | 2.5      |
| Benzyl alcohol            | 5.0      |
| Propylene glycol          | 5.0      |
| Polyethylene glycol 3350  | 40.0     |
| Polyethylene glycol 400   | qs 100   |
| Buffer to pH              | 7.5      |
| C.                        |          |
| Loperamide hydrochloride  | 1.0      |
| Benzyl alcohol            | 5.0      |
| Propylene glycol          | 5.0      |
| Polyethylene glycol 3350  | 40.0     |
| Polyethylene glycol 400   | qs 100   |
| Buffer to pH              | 7.5      |

EXAMPLE 8
Yeast-Induced Inflammation

A Randall-Selitto assay (see, Randall et al. (1957) *Arch. Int. Pharmacodyn.* 111:409–419) was performed to determine the effect of loperamide upon the pain threshold of the yeast-injected left hind paw of male Sprague-Dawley rats.

Each rat was injected with 100 $\mu$l of a 20% yeast solution into the plantar surface of the left hind paw. Four hours later loperamide was administered at 10, 50 or 250 $\mu$l/100 $\mu$l/rat in a vehicle of 10% DMSO (n=10/dose group). Control rats were treated with 10% DMSO alone (n=20). The pain thresholds of the inflamed and non-inflamed paws were measured by application of a pressure stimulus to the paw and the paw pressure threshold in gram (g) was recorded.

As shown in the following table, loperamide produced a dose-dependent increase in the paw pressure threshold.

| Dose, $\mu$g | Paw Pressure Threshold, g |
|--------------|---------------------------|
| 10           | 66 ± 15                   |
| 50           | 124 ± 29                  |
| 250          | 153 ± 25                  |

EXAMPLE 9
Assessment of the effect of loperamide administered into the paw on formalin-induced nociception A. Model Administration of formalin into the paw results in a localized inflammation and in spontaneous flinching behavior. This response is indicative of pain. Flinching responses include paw lifting and paw shaking, and are characterized by a rapid vibration of the paw after drawing it under the body. The flinching response can be reliably quantitated and exhibits two peaks of activity which are indicative of acute and tonic pain. The early or acute phase lasts from 0–5 minutes post-formalin and is followed by a quiescent period lasting approximately 15 minutes. The tonic phase occurs form 20–35 minutes following formalin injection and is the interval where the number of flinching responses is maximal. This model has been characterized in several species and is sensitive to the analgesic effects of opiates administered by a variety of routes, including local administration directly into the paw.

B. Methods

1. Induction of inflammation

Male Sprague-Dawley rats weighing 70–90 g were used. Inflammation was induced by subcutaneous injection of 50 μl of a 5% formalin solution into the dorsal surface of the right hind paw.

Flinching behavior was quantitated by counting the number of responses that occurred during the tonic phase of pain, lasting from 20–35 minutes after formalin injection. Results are expressed as the mean percent antagonism of formalin-induced flinching calculated for individual drug-treated, formalin-injected rats using the following formula:

$$\frac{(\text{mean formalin response} - \text{mean saline response}) - \text{individual response}}{\text{mean formalin response} - \text{mean saline response}} \times 100$$

in which the mean formalin response is the mean behavioral score of vehicle-treated and formalin-injected rats. The mean saline response is the pooled behavior score from rats injected with 50 μl of saline into the paw.

2. Drugs and drug delivery

Loperamide (Research Biochemicals Inc., Natick, Mass.) was administered at doses of 3, 10, 30, 100 or 300 μg/50 μl of a 20% cremophor EF vehicle (BASF, Rahway, N.J.) to groups of rats (7–9 per dose group). Injections of drug were given into the dorsal surface of the paw at 10 minutes prior to formalin injection, and were counterbalanced across treatment groups.

C. Results

As shown in the following table, when inflammation-induced tonic pain was produced by formalin injection into the paw, loperamide produced a dose-dependent antinociception, as measured by a decrease in flinching behaviors. At the highest dose of 300 μg, practically no flinching behavior was observed.

| Summary of the effect of loperamide or formalin-induced inflammation | |
|---|---|
| Dose, μg | % Antagonism of Late Phase Flinching |
| 3 | 53 ± 10 |
| 10 | 55 ± 15 |
| 30 | 73 ± 10 |
| 100 | 74 ± 11 |
| 300 | 97 ± 2 |

Data are the mean ± SEM

D. Conclusions

These data indicate the following:

1) Loperamide administered directly into the paw reduces the pain associated with formalin-induced inflammation.

2) The effect of loperamide is dose-dependent, with greater antinociception occurring at higher doses.

Since modifications will be apparent to those of skill in this art, it is intended that this invention be limited only by the scope of the appended claims.

What is claimed:

1. A method of treating peripheral hyperalgesia, comprising topically or locally administering to a mammal in need of such treatment an effective amount of a composition, comprising an anti-hyperalgesically effective amount of one or more compound(s) in a vehicle formulated for topical or local administration, wherein the compound is an anti-diarrheal compound that exerts anti-hyperalgesic activity via peripheral opiate receptors without causing central nervous system (CNS) opiate receptor-mediated side effects.

2. The method of claim 1, wherein the composition is applied to the eye.

3. The method of claim 1, wherein the composition is applied to the cornea.

4. The method of claim 1, wherein the concentration of the compound in the composition is greater than about 2% by weight.

5. A method of treating peripheral hyperalgesia in the eye, comprising:

topically applying or locally administering to the eye of a mammal in need of such treatment an effective amount of a composition comprising an anti-hyperalgesically effective amount of one or more compound(s) in a vehicle formulated for topical application or local administration to the eye, wherein the compound is an anti-diarrheal compound that:

(a) has activity as a peripheral anti-hyperalgesic; and (b) a B/A ratio greater than diphenoxylate, wherein:

B is the $ED_{50}$ of the compound in an assay that measures central nervous system (CNS) activity of the compound;

A is the $ED_{50}$ of the compound in an assay that measures anti-diarrheal activity of the compound;

the relative activities of the compound are compared to the activities of diphenoxylate in the same assays.

6. The method of claim 5, wherein the assay in which B is determined is a tail clip or hot plate analgesic assay.

7. The method of claim 5, wherein the assay in which anti-diarrheal activity is measured is a Castor oil test or an assay that measures antagonism by the compound of prostaglandin $E_2$ ($PGE_2$)-induced diarrhea.

8. The method of claim 7, wherein the assay in which B is determined is a tail clip or hot plate analgesic assay.

9. The method of claim 8, wherein both assays are performed by administering the compound by the same route.

10. The method of claim 5, wherein the compound is loperamide or an N-oxide thereof.

11. The method of claim 5, wherein the compound is applied to the cornea.

12. A method of treating peripheral hyperalgesia, comprising topically applying or locally administering to a mammal in need of such treatment an effective amount of a composition, comprising an anti-hyperalgesically effective amount of one or more compound(s) in a vehicle formulated for topical application or local administration, wherein:

at least one of the compounds has formula (I) or is an N-oxide thereof or is a pharmaceutically acceptable salt or acid thereof:

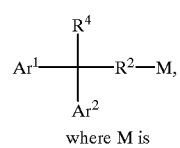

where M is

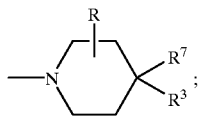

Ar¹ and Ar² are each independently selected from aryl groups containing from 5 to 7 members in the ring, each is unsubstituted or substituted with one or more substituents selected from halo, haloalkyl, hydroxy, alkyl, alkyloxy, aminosulfonyl, alkylcarbonyl, nitro, haloalkyl, trifluoromethyl, amino, aminocarbonyl, phenylcarbonyl or thienyl, where the alkyl groups are straight or branched chains lower alkyl containing from 1 to 6 carbon atoms;

$R^2$ is a direct bond, straight or branched chain alkylene of 1 to 12 carbon atoms, or is alkenylene or alkynylene of 2 to 6 carbon atoms and one or two double bonds or triple bonds;

$R^3$ is $Ar^3$ or $Y-Ar^3$, where Y is alkylene or alkyl having 1 to 3 carbon atoms;

$Ar^3$ is aryl containing from 5 to 7 members in the ring, which is unsubstituted or substituted with one or more substituents selected from halo, halo lower alkyl or lower alkyl;

R is hydrogen, alkyl, halo, haloalkyl or $OR^9$;

$R^9$ is selected from alkyl, arylalkyl, alkylcarbonyl, aminoalkyl, alkylaminoalkyl or dialkylaminoalkyl, in which the alkyl groups are straight or branched chains containing 1 to 12 carbon atoms;

$R^4$ is selected from among:
(i) 5- to 7-membered aryl groups, which are unsubstituted or substituted with lower alkyl, halo lower alkyl or halo, or
(ii) 3- to 5-membered heterocyclic rings, containing one to three heteroatoms, that are unsubstituted or substituted with halo, halo lower alkyl or lower alkyl, or
(iii) alkyl containing from 1 to 8 carbon atoms, alkenyl containing 3 to 6 carbon atoms, cycloalkyl containing from 3 to 6 carbon atoms, cycloalkyl alkyl in which the first alkyl contains 3 to 6 carbons and the second contains 1 to 3 carbons, or cycloalkenyl containing 4 to 7 carbons, or

(iv)

where $R^5$ and $R^6$ are either:
(i) independently selected from hydrogen, alkyl, which is a straight or branched chain containing 1 to 12 carbon atoms, alkenyl, which is straight or branched chain, containing 1 to 12, carbon atoms and one or two double bonds, or aryl, which contains 5 to 7 carbon atoms, or
(ii) $R^5$ and $R^6$ are selected from carbon chains, and carbon chains containing one or more heteroatoms, so that with the nitrogen atom to which each is attached they form a 3- to 6-membered heterocyclic ring containing one to three heteroatoms; wherein each group of (i) or (ii) is optionally unsubstituted or substituted with halo, halo lower alkyl or lower alkyl; and $R^7$ is selected from among:
H; OH; $R^{14}OR^{13}$ in which $R^{13}$ is hydrogen or lower alkyl, alkanoyl containing 2 to 5 carbon atoms, and $R^{14}$ is lower alkenyl or lower alkyl; $CH_2NR^{15}R^{16}$ in which $R^{15}$ is hydrogen, lower alkyl or lower alkanoyl and $R^{16}$ is hydrogen or lower alkyl; $OR^{15}$; $R^{22}OR^{13}$, in which $R^{22}$ is lower alkyl; $C(O)OR^{17}$ in which $R^{17}$ is hydrogen, alkyl containing from 1 to 7 carbons or alkenyl having 3–7 carbon atoms, aryl or 3- to 6-membered heteroaryl containing 1–2 heteroatoms; and wherein the compound is an anti-diarrheal compound that exerts anti-hyperalgesic activity via peripheral opiate receptors, and:
(a) has activity as a peripheral anti-hyperalgesic; and
(b) a B/A ratio greater than diphenoxylate, wherein:
B is the $ED_{50}$ of the compound in an assay that measures central nervous system (CNS) activity of the compound;
the assay in which B is determined is a tail clip or hot plate assay;
A is the $ED_{50}$ of the compound in an assay the measures anti-diarrheal activity of the compound;
the assay in which anti-diarrheal activity is measured is a Castor oil test or an assay that measures antagonism by the compound of prostaglandin $E_2$ ($PGE_2$)-induced diarrhea; and
the relative activities of the compound are compared to the activities of diphenoxylate in the same assays.

13. The method of claim 12, wherein:
$R^2$ is a direct bond, straight or branched chain alkylene of 1 to 3 carbon atoms;
$Ar^1$, $Ar^2$ and $Ar^3$ are each independently phenyl that is unsubstituted or substituted with up to three substituents selected from halo, halo lower alkyl or lower alkyl;
$R^2$ is CH=CH, $(CH_2)_2$ or $CH_2CH(CH_3)$;
R is hydrogen, lower alkyl, halo, halo lower alkyl, or $OR^9$, and is at the 3-position so that the piperidinyl ring has the formula:

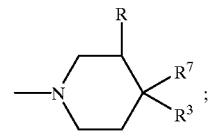

$R^9$ is selected from alkyl, arylalkyl, alkylcarbonyl, aminoalkyl, alkylaminoalkyl, dialkylaminoalkyl, in which the alkyl groups are straight or branched chains and contain 1–6 carbons in the chain;

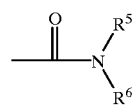

where $R^5$ and $R^6$ are independently selected from hydrogen, lower alkyl, lower alkenyl, and aryl, which are each unsubstituted or substituted with halo, halo lower alkyl or lower alkyl; and $R^7$ is selected from:

H;

OH;

$OR^{15}$ in which $R^{15}$ is hydrogen, lower alkyl or lower alkanoyl.

14. The method of claim 12, wherein:

$R^3$ is $Ar^3$ $Ar^3$ is aryl containing from 5 to 7 members in the ring, which is unsubstituted or substituted with up to three substituents selected from halo, halo lower alkyl or lower alkyl;

$R^2$ is a direct bond, straight or branched chain alkylene of 1 to 12 carbon atoms;

R is hydrogen, alkyl or $OR^9$;

$R^9$ is selected from alkyl, arylalkyl, alkylcarbonyl, aminoalkyl, alkylaminoalkyl or dialkylaminoalkyl, in which the alkyl groups are straight or branched chains and containing 1 to 6 carbon atoms;

$R^4$ is:

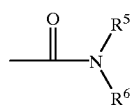

where $R^5$ and $R^6$ are either:
(i) independently selected from hydrogen, alkyl that is a straight or branched chain 1 to 3 carbons, alkenyl that is straight or branched chain, containing 1 to 4 carbons and 1 double bond; or
(ii) $R^5$ and $R^6$, with the nitrogen atom to which each is attached form a heterocycle selected from pyrrolidinyl, piperidinyl, alkylpiperidinyl, morpholinyl, oxadiazolyl or triazolyl radicals, each of which is unsubstituted or substituted with one or more substituents selected from halo, halo lower alkyl or lower alkyl; and $R^7$ is H, OH, C(O)OH, C(O)H or —$R^{14}OR^{13}$ in which $R^{13}$ is hydrogen or lower alkyl, containing 1–4 carbons, or is an alkanoyl containing 2 or 3 carbon atoms, and $R^{14}$ is methyl or ethyl.

15. The method of claim 14, wherein:

$Ar^1$ and $Ar^2$ are phenyl,

R is hydrogen or methyl, $R^2$ is $(CH_2)_2$ or $CH_2CHCH_3$, $R^5$ and $R^6$ are independently methyl or ethyl or with the nitrogen to which each is linked form pyrrolidine, piperidinyl and $R^3$ is unsubstituted phenyl, 4-chlorophenyl, 4-bromophenyl, 4-fluorophenyl, 3,4,-di-halophenyl or 3-trifluoromethylphenyl; and $R^7$ is OH.

16. The method of claim 15, wherein the compound is selected from compounds in which:
(i) $Ar^1$ and $Ar^2$ are phenyl, R is hydrogen, $R^2$ is $(CH_2)_2$, $R^5$ and $R^6$, with the nitrogen to which each is linked form pyrrolidine and $R^3$ is 4-chlorophenyl or 3,4,-dichlorophenyl:
(ii) $Ar^1$ and $Ar^2$ are phenyl, R is hydrogen, $R^2$ is $(CH_2)_2$, $R^5$ and $R^6$, with the nitrogen to which each is linked form piperidinyl and $R^3$ is phenyl;
(iii) $Ar^1$ and $Ar^2$ are phenyl, $R^2$ is $(CH_2)_2$, R is hydrogen, $R^5$ and $R^6$ are each methyl and $R^3$ is 4-bromophenyl;
(iv) $Ar^1$ and $Ar^2$ are phenyl, $R^2$ is $(CH_2)_2$, R is hydrogen, $R^5$ and $R^6$ are methyl and ethyl, respectively, and $R^3$ is 4-chlorophenyl;
(v) $Ar^1$ and $Ar^2$ are phenyl, $R^2$ is $CH_2CHCH_3$, R is hydrogen, $R^5$ and $R^6$ are each methyl and $R^3$ is 4-fluorophenyl; and
(vi) $Ar^1$ and $Ar^2$ are phenyl, $R^2$ is $CH_2CH_2$, R is 4-methyl, $R^5$ and $R^6$ are each methyl and $R^3$ is 3-trifluoromethylphenyl or phenyl.

17. The method of claim 12, wherein:

$R^4$ is

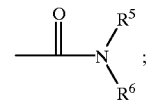

$R^5$ and $R^6$ are either:
(i) independently selected from hydrogen, lower alkyl, phenyl or lower alkenyl, or
(ii) $R^5$ and $R^6$, with the nitrogen atom to which each is attached are form a heterocycle selected from a 1,3,4-oxadiazolyl, 4-morpholinyl, or di($C_1$–$C_6$ alkyl)-morpholinyl radical;

$R^2$ is $(CH_2)_2$ or $CH_2CH(CH_3)$;

$R^7$ is OH, C(O)OH or C(O)H; and

R is hydrogen, lower alkyl, C(O)H, or C(O)OH and R is at the 3-position so that the piperidinyl ring has the formula:

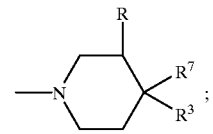

and $R^3$ is phenyl or halo-substituted phenyl.

18. The method of claim 17, wherein:

$R^7$ is OH;

$R^3$ is phenyl that is unsubstituted or substituted with halo;

R is H or alkyl containing 1 to 3 carbon atoms;

$R^2$ is lower alkyl;

$R^4$ is phenyl or pyridyl or is:

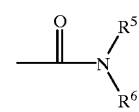

where $R^5$ and $R^6$ are either:
(i) independently selected from H, alkyl, phenyl, phenylalkyl or 2-propenyl, in which the alkyl groups are lower alkyl; or
(ii) $R^5$ and $R^6$, with the nitrogen to which each is attached form pyrrolidinyl, piperidinyl, $C_1$–$C_6$ alkylpiperidinyl, 4-morpholinyl or 2,6-di($C_1$–$C_6$ alkyl) morpholinyl radicals; and $Ar^1$ and $Ar^2$ are independently selected from substituted or unsubstituted phenyl.

19. The method of claim 18, wherein

R is H or methyl;

R³ is phenyl or substituted phenyl in which the substituents are selected from the group consisting of alkyl, alkoxyalkyl, halo and trifluoroalkyl;

R² is a direct bond, straight or branched chain alkylene of 1 to 4 carbons;

Ar¹ and Ar² are independently phenyl, which is unsubstituted or substituted with lower alkyl, alkoxy lower alkyl, halo or halo lower alkyl;

R⁴ is:

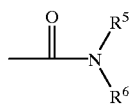

where R⁵ and R⁶ are either:
(i) independently selected from H, lower alkyl, phenyl, phenyl lower alkyl or 2-propenyl; or
(ii) R⁵ and R⁶, with the nitrogen atom to which each is attached, form a pyrrolidinyl, piperidinyl, $C_1$–$C_6$ alkylpiperidinyl, 4-morpholinyl or 2,6-di($C_1$–$C_6$ alkyl) morpholinyl radical.

20. The method of claim 12, wherein the composition comprises a compound selected from 2-[4-(4-hydroxy-4-phenylpiperidino)-2,2-diphenylbutyryl]piperidine; 4-{4-[4-hydroxy-4-(3-trifluoromethylphenyl)piperidino]-2,2-diphenylbutyryl}morpholine; 1-{4–14-hydroxy-4-(3-trifluoromethylphenyl)piperidino]-2,2-diphenylbutyl}piperidine; 4-(p-chlorophenyl)-4-hydroxy-N-N-,γ-trimethyl-α,α-diphenylpiperidine-1-butyramide;4-(3,4-dichlorophenyl)-N,N-diethyl-4-hydroxy-αα-diphenylpiperidine-1-butyramide; 4-(3,4-dichlorophenyl)-4-hydroxy-N,N-dimethyl-α,α-diphenylpiperidine-1-butyramide; 4-(3,4-dichlorophenyl)-4-hydroxy-N,N-dimethyl-α,α-diphenylpiperidine-1-butyramide; 4-(4-chloro-3trifluoromethylphenyl-4-hydroxy-N,N-dimethyl-α,α-diphenylpiperidine-1-butyramide; 4-(p-fluorophenyl)-4-hydroxy-N,N,γ-trimethyl-α,α-diphenylpiperidine-1-butyramide; 4-(p-bromophenyl)-4-hydroxy-N,N-dimethyl-α,α-diphenylpiperidine-1-butyramide; 1-{4-[4-(3,4-dichlorophenyl-4-hydroxypiperidino]-2,2-diphenylbutyryl}pyrrolidine; or 4-(p-chlorophenyl)-N-ethyl-4-hydroxy-N-methyl-α,α-diphenylpiperidine-1-butyramide.

21. A method of treating peripheral hyperalgesia, comprising topically applying or locally administering to a mammal in need of such treatment an effective amount of a composition comprising an anti-hyperalgesically effective amount of one or more compound(s) in a vehicle formulated for topical application or local administration, wherein:

at least one of the compounds has formula (III):

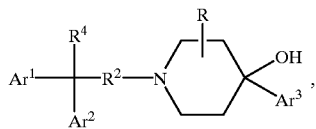

III or is a pharmaceutically acceptable salt or acid thereof, wherein:

Ar¹ and Ar² are each independently selected from aryl containing from 5 to 7 members in the ring;

R² is a direct bond, straight or branched chain alkylene of 1 to 12 carbon atoms or is alkenylene of 2 to 6 carbon atoms and one or two double bond;

R is hydrogen, alkyl, halo lower alkyl or halo;

R⁴ is:

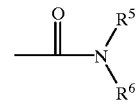

where R⁵ and R⁶ are either:
(i) independently selected from hydrogen or alkyl or alkenyl, in which the carbon chains are straight or branched chains, or
(ii) R⁵ and R⁶, with the nitrogen atom to which each is attached, form a 5- to 6-membered heterocyclic ring containing one or two heteroatoms;

Ar³ is aryl containing from 5 to 7 members in the ring; and wherein the compound is an anti-diarrheal compound that exerts anti-hyperalgesic activity via peripheral opiate receptors, and:
(a) has activity as a peripheral anti-hyperalgesic; and
(b) a B/A ratio greater than diphenoxylate, wherein:
B is the $ED_{50}$ of the compound in an assay that measures central nervous system (CNS) activity of the compound;
the assay in which B is determined is a tail clip or hot plate assay;
A is the $ED_{50}$ of the compound in an assay the measures anti-diarrheal activity of the compound;
the assay in which anti-diarrheal activity is measured is a Castor oil test or an assay that measures antagonism by the compound of prostaglandin $E_2$ ($PGE_2$)-induced diarrhea; and
the relative activities of the compound are compared to the activities of diphenoxylate in the same assays.

22. The method of claim 21, wherein:

Ar¹ and Ar² are each phenyl unsubstituted or substituted with up to three substituents selected from halo, halo lower alkyl or alkyl in which the alkyl groups are straight or branched chains and are lower alkyl containing from 1 to 6 carbons;

R² is a direct bond, straight or branched chain alkylene of 1 to 4 carbons;

R is hydrogen, lower alkyl, halo lower alkyl, or halo, and is in the 3-position;

R⁴ is:

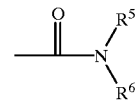

where

R⁵ and R⁶ are either:
(i) independently selected from hydrogen or alkyl or alkenyl, in which the carbon chains are a straight or branched chain and contain 1 to 6 carbons, or
(ii) R⁵ and R⁶, with the nitrogen atom to which each is attached, form a 5- to 6-member heterocyclic ring selected from pyrrolidinyl, piperidinyl, alkylpiperidinyl, and morpholinyl radicals; and Ar³ is aryl containing from 5 to 7 members in the ring, which is unsubstituted or substituted with up to three substituents selected from halo, halo lower alkyl or lower alkyl.

* * * * *

UNITED STATES PATENT AND TRADEMARK OFFICE
CERTIFICATE OF CORRECTION

PATENT NO. : 6,166,039
DATED : December 26, 2000
INVENTOR(S) : Yaksh

It is certified that error appears in the above-identified patent and that said Letters Patent is hereby corrected as shown below:

References Cited,
Item [56], please add the following in the Foreign Patent Documents:
-- 9527510      10/19/95      PCT --

Column 5,
Line 17, please replace "4 (aroylamino)piperidine-butanimide" with -- 4-(aroylamino) piperidine-butanamide --;

Column 7,
Line 63, please replace "arlyalkyloxy" with -- arylalkyloxy --;

Column 18,
Line 38 and 39, replace "heterocyles" with -- heterocycles --;

Column 24,
Line 59, please replace "phenylmethyoxy" with -- phenylmethoxy --;

Column 38,
Line 37, please replace "Selitto]" with -- Selitto --;

Please replace claims 13 and 20 with the following claims:
13.    The method of claim 133, wherein:
$R^2$ is a direct bond, straight or branched chain alkylene of 1 to 3 carbon atoms;
$Ar^1$, $Ar^2$ and $Ar^3$ are each independently phenyl that is unsubstituted or substituted with up To three substituents selected from halo, halo lower alkyl or lower alkyl;
$R^2$ is CH = CH, $(CH_2)_2$ or $CH_2CH(CH_3)$;
R is hydrogen, lower alkyl, halo, halo lower alkyl, or $OR^9$, and is at the 3-position so that the piperidinyl ring has the formula:

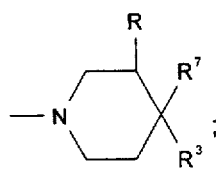

$R^9$ is selected from alkyl, arylalkyl, alkylcarbonyl, aminoalkyl, alkylaminoalkyl, diallkylaminoalkyl, in which the alkyl groups are straight or branched chains and contain 1-6 carbons in the chain;

UNITED STATES PATENT AND TRADEMARK OFFICE
CERTIFICATE OF CORRECTION

PATENT NO.    : 6,166,039
DATED         : December 26, 2000
INVENTOR(S)   : Yaksh It is certified that error appears in the above-identified patent and that said Letters Patent is hereby corrected as shown below:

$R^4$ is

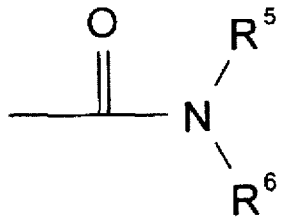

where $R^5$ and $R^6$ are independently selected from hydrogen, lower alkyl, lower alkenyl, and aryl, which are each unsubstituted or substituted with halo, halo lower alkyl or lower alkyl; and
$R^7$ is selected from:
    H;
    OH;
    $OR^{15}$ in which $R^{15}$ is hydrogen, lower alkyl or lower alkanoyl.

20.    The method of claim 133, wherein the composition comprises a compound selected from 2-[4-(4-hydroxy-4-phenylpiperidino)-2,2-diphenylbutyryl]piperidine; 4-{4-[4-hydroxy-4-(3-trifluoromethylphenyl)piperidino]-2,2-diphenylbutyryl}morpholine; 1-{4-[4-hydroxy-4-(3-trifluoromethylphenyl)piperidino]-2,2-diphenylbutyl}piperidine;4-(p-chlorophenyl)-4-hydroxy-N-N-,y-trimethyl-*a,a*-diphenylpiperidine-1-butyramide;4-(3,4-dichlorophenyl)-N,N-diethyl-4-hydroxy-*a,a*-diphenylpiperidine-1-butyramide; 4-(3,4-dichlorophenyl)-4-hydroxy-N,N-dimethyl-*a,a*-diphenyl-piperidine-1-butyramide; 4-(4-chloro-3-trifluoromethylphenyl)-4-hydroxy-N,N-dimethyl-*a,a*-diphenylpiperidine-1-butyramide; 4-(p-fluorophenyl)-4-hydroxy-N-N,y-trimethyl-a,a-diphenylpiperidine-1-butyramide; 4-(p-bromophenyl)-4-hydroxy-N-N-dimethyl-a,a-diphenylpiperidine-1-butyramide; 1-{4 [4-(3,4-dichlorophenyl)-4-hydroxypiperidino]-2,2-diphenylbutyryl}pyrrolidine;or 4-(p-chlorophenyl)-N-ethyl-4-hydroxy-N-methyl-*a,a*-diphenylpiperidine-1-butyramide.

Signed and Sealed this

Fourth Day of December, 2001

*Attest:*

*Attesting Officer*

NICHOLAS P. GODICI
*Acting Director of the United States Patent and Trademark Office*

UNITED STATES PATENT AND TRADEMARK OFFICE
CERTIFICATE OF CORRECTION

PATENT NO.   : 6,166,039
DATED        : December 26, 2000
INVENTOR(S)  : Yaksh

It is certified that error appears in the above-identified patent and that said Letters Patent is hereby corrected as shown below:

References Cited,
Item [56], please add the following in the FOREIGN PATENT DOCUMENTS:
-- 9527510    10/19/95    PCT --

Column 5,
Line 17, please replace "4 (aroylamino)piperidine-butanimide" with -- 4-(aroylamino) piperidine-butanamide --;

Column 7,
Line 63, please replace "arlyalkyloxy" with -- arylalkyloxy --;

Column 18,
Line 38 and 39, replace "heterocyles" with -- heterocycles --;

Column 24,
Line 59, please replace "phenylmethoxy" with -- phenylmethoxy --;

Column 38,
Line 37, please replace "selitto]" with -- Selitto --;

Please replace claims 13 and 20 with the following claims:
13. The method of claim 13, wherein:
$R^2$ is a direct bond, straight or branched chain alkylene of 1 to 3 carbon atoms;
$Ar^1$, $Ar^2$ and $Ar^3$ are each independently phenyl that is unsubstituted or substituted with up to three substituents selected from halo, halo lower alkyl or lower alkyl;
$R^2$ is $CH = CH$, $(CH_2)_2$ or $CH_2CH(CH_3)$;
R is hydrogen, lower alkyl, halo, halo lower alkyl, or $OR^9$, and is at the 3-position so that the piperidinyl ring has the formula:

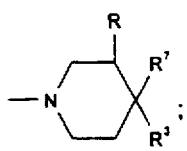

$R^9$ is selected from alkyl, arylalkyl, alkylcarbonyl, aminoalkyl, alkylaminoalkyl, diallkylaminoalkyl, in which the alkyl groups are straight or branched chains and contain 1-6 carbons in the chain;

UNITED STATES PATENT AND TRADEMARK OFFICE
CERTIFICATE OF CORRECTION

PATENT NO. : 6,166,039
DATED : December 26, 2000
INVENTOR(S) : Yaksh

It is certified that error appears in the above-identified patent and that said Letters Patent is hereby corrected as shown below:

$R^4$ is

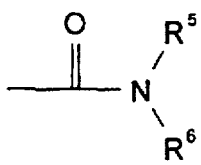

where $R^5$ and $R^6$ are independently selected from hydrogen, lower alkyl, lower alkenyl, and aryl, which are each unsubstituted or substituted with halo, halo lower alkyl or lower alkyl; and
$R^7$ is selected from:
H;
OH;
$OR^{15}$ in which $R^{15}$ is hydrogen, lower alkyl or lower alkanoyl.

20. The method of claim 133, wherein the composition comprises a compound selected from 2-[4-(4-hydroxy-4-phenylpiperidino)-2,2-diphenylbutyryl]piperidine; 4-{4-[4-hydroxy-4-(3-trifluoromethylphenyl)piperidino]-2,2-diphenylbutyryl}morpholine; 1-{4-[4-hydroxy-4-(3-trifluoromethylphenyl)piperidino]-2,2-diphenylbutyl}piperidine;4-(p-chlorophenyl)-4-hydroxy-N-N-,y-trimethyl-a,a-diphenylpiperidine-1 -butyramide;4-(3,4-dichlorophenyl)-N,N-diethyl-4-hydroxy-a,a-diphenylpiperidine-1-butyramide; 4-(3,4-dichlorophenyl)-4-hydroxy-N,N-dimethyl-a,a-diphenylpiperidine-1-butyramide; 4-(4-chloro-3-trifluoromethylphenyl)-4-hydroxy-N,N-dimethyl-a,a-diphenylpiperidine-1-butyramide; 4-(p-fluorophenyl)-4-hydroxy-N-N,y-trimethyl-a,a-diphenylpiperidine 1-butyramide; 4-(p-bromophenyl)-4-hydroxy-N-N-dimethyl-a,a-diphenylpiperidine-1-butyramide; 1-{4 [4-(3,4-dichlorophenyl)-4-hydroxypiperidino]-2,2-diphenylbutyryl}pyrrolidine;or 4-(p-chlorophenyl)-N-ethyl-4-hydroxy-N-methyl-a,a-diphenylpiperidine-1-butyramide.

This Certificate supercedes Certificate of Correction issued December 4, 2001.

Signed and Sealed this

Eighth Day of January, 2002

Attest:

JAMES E. ROGAN
Director of the United States Patent and Trademark Office

Attesting Officer